US012128018B2

(12) United States Patent
Holson et al.

(10) Patent No.: US 12,128,018 B2
(45) Date of Patent: Oct. 29, 2024

(54) COMBINATION OF A SELECTIVE HISTONE DEACETYLASE 3 (HDAC3) INHIBITOR AND AN IMMUNOTHERAPY AGENT FOR THE TREATMENT OF CANCER

(71) Applicant: KDAc Therapeutics, Inc., Cambridge, MA (US)

(72) Inventors: Edward Holson, Newton, MA (US); Mariana Nacht, Belmont, MA (US)

(73) Assignee: KDAc Therapeutics, Inc., Cambridge, MA (US)

(*) Notice: Subject to any disclaimer, the term of this patent is extended or adjusted under 35 U.S.C. 154(b) by 77 days.

(21) Appl. No.: 16/246,320

(22) Filed: Jan. 11, 2019

(65) Prior Publication Data

US 2019/0216754 A1 Jul. 18, 2019
US 2021/0177781 A9 Jun. 17, 2021

Related U.S. Application Data

(60) Provisional application No. 62/616,831, filed on Jan. 12, 2018.

(51) Int. Cl.
| | |
|---|---|
| *A01N 43/00* | (2006.01) |
| *A01N 43/46* | (2006.01) |
| *A61K 31/167* | (2006.01) |
| *A61K 31/403* | (2006.01) |
| *A61K 31/415* | (2006.01) |
| *A61K 31/55* | (2006.01) |
| *A61K 39/395* | (2006.01) |
| *A61K 45/06* | (2006.01) |
| *A61P 35/00* | (2006.01) |
| *C07K 16/28* | (2006.01) |
| *A61K 39/00* | (2006.01) |

(52) U.S. Cl.
CPC .......... *A61K 31/167* (2013.01); *A61K 31/403* (2013.01); *A61K 31/415* (2013.01); *A61K 39/3955* (2013.01); *A61K 45/06* (2013.01); *A61P 35/00* (2018.01); *C07K 16/2818* (2013.01); *A61K 2039/545* (2013.01); *C07K 2317/73* (2013.01)

(58) Field of Classification Search
None
See application file for complete search history.

(56) References Cited

U.S. PATENT DOCUMENTS

| | | |
|---|---|---|
| 3,689,550 A | 9/1972 | Schellenbaum et al. |
| 3,850,931 A | 11/1974 | Kim et al. |
| 4,404,356 A | 9/1983 | Andrews |
| 5,135,949 A | 8/1992 | von der Saal et al. |
| 5,137,918 A | 8/1992 | Weiershausen et al. |
| 5,284,656 A | 2/1994 | Platz et al. |
| 5,451,569 A | 9/1995 | Wong et al. |
| 5,525,727 A | 6/1996 | Bodor |
| 5,618,803 A | 4/1997 | Bodor |
| 5,635,503 A | 6/1997 | Poindexter et al. |
| 5,783,522 A | 7/1998 | Schaefer et al. |
| 5,811,097 A | 9/1998 | Allison et al. |
| 5,855,887 A | 1/1999 | Allison et al. |
| 5,886,044 A | 3/1999 | Widdowson et al. |
| 6,051,227 A | 4/2000 | Allison et al. |
| 6,313,122 B1 | 11/2001 | Beight et al. |
| 6,407,137 B2 | 6/2002 | Shashoua |
| 6,645,990 B2 | 11/2003 | Askew et al. |
| 6,653,309 B1 | 11/2003 | Saunders et al. |
| 6,869,953 B2 | 3/2005 | Haag et al. |
| 6,946,462 B2 | 9/2005 | Haag et al. |
| 6,976,462 B2 * | 12/2005 | Jesel ........................ F01L 1/185 123/90.44 |
| 6,984,720 B1 | 1/2006 | Korman et al. |
| 7,034,121 B2 | 4/2006 | Carreno et al. |
| 7,119,074 B2 | 10/2006 | Ekwuribe et al. |
| 7,550,490 B2 | 6/2009 | Lu et al. |
| 7,824,679 B2 | 11/2010 | Hanson et al. |
| 8,017,114 B2 | 9/2011 | Korman et al. |
| 8,138,168 B1 | 3/2012 | Jones |
| 8,158,825 B2 | 4/2012 | Grimm et al. |
| 8,211,901 B2 | 7/2012 | Lu et al. |
| 8,318,916 B2 | 11/2012 | Korman et al. |
| 8,450,525 B2 | 5/2013 | Rajagopal et al. |
| 8,475,790 B2 | 7/2013 | Jure-Kunkel |

(Continued)

FOREIGN PATENT DOCUMENTS

| | | |
|---|---|---|
| BE | 891537 | 4/1982 |
| CN | 105120860 B | 1/2021 |

(Continued)

OTHER PUBLICATIONS

Eden et al. ("MP65-07 Treatment With the Histone Deacetylase Inhibitor, CI-994, in Combination With PD-1 Blockade Leads to Regression of Intravesical Murine Tumors." The Journal of Urology 197.4S (2017): e854-e855.).*

Berger et al. (Phase I Safety and Pharmacokinetic Study of CT-011, a Humanized Antibody Interacting with PD-1, in Patients with Advanced Hematologic Malignancies. Clin Cancer Res 2008; 14(10) May 15, 2008).*

International Preliminary Report on Patentability for Application No. PCT/US2019/013375, mailed Jul. 23, 2020.

(Continued)

*Primary Examiner* — Layla Soroush

(74) *Attorney, Agent, or Firm* — Wolf, Greenfield & Sacks, P.C.

(57) ABSTRACT

Aspects of the disclosure relate to compositions, kits, and methods for the treatment of cancer that utilize a selective histone deacetylase 3 (HDAC3) inhibitor. In some aspects, the compositions, kits, and methods relate to use of a selective HDAC3 inhibitor in combination with an immunotherapy agent (e.g., an immune checkpoint inhibitor).

34 Claims, 14 Drawing Sheets

(56) References Cited

U.S. PATENT DOCUMENTS

| | | |
|---|---|---|
| 8,598,168 B2 | 12/2013 | Moradei et al. |
| 8,685,394 B2 | 4/2014 | Jure-Kunkel |
| 8,957,066 B2 | 2/2015 | Jacques et al. |
| 9,265,734 B2 | 2/2016 | Rusche et al. |
| 9,365,498 B2 | 6/2016 | Holson et al. |
| 9,447,030 B2 | 9/2016 | Holson et al. |
| 9,512,143 B2 | 12/2016 | Jacques et al. |
| 9,540,395 B2 | 1/2017 | Jacques et al. |
| 9,790,184 B2 | 10/2017 | Holson et al. |
| 9,796,664 B2 | 10/2017 | Rusche et al. |
| 9,890,172 B2 | 2/2018 | Holson et al. |
| 9,914,717 B2 | 3/2018 | Holson et al. |
| 9,970,184 B2 | 5/2018 | Green |
| 9,988,343 B2 | 6/2018 | Mazitschek et al. |
| 10,662,199 B2 | 5/2020 | Holson et al. |
| 10,793,538 B2 | 10/2020 | Holson et al. |
| 11,377,423 B2 | 7/2022 | Holson et al. |
| 11,572,368 B2 | 2/2023 | Holson et al. |
| 2002/0039581 A1 | 4/2002 | Carreno et al. |
| 2002/0173507 A1 | 11/2002 | Santora et al. |
| 2002/0193367 A1 | 12/2002 | Adam et al. |
| 2003/0027862 A1 | 2/2003 | Haning et al. |
| 2003/0064330 A1 | 4/2003 | Kyota et al. |
| 2003/0159221 A1 | 8/2003 | Lang |
| 2003/0166639 A1 | 9/2003 | Adam et al. |
| 2005/0201994 A1 | 9/2005 | Korman et al. |
| 2006/0008517 A1 | 1/2006 | Lynch et al. |
| 2007/0054904 A1 | 3/2007 | Knolle et al. |
| 2008/0070954 A1 | 3/2008 | Lim et al. |
| 2008/0132503 A1 | 6/2008 | Moradei et al. |
| 2009/0055944 A1 | 2/2009 | Korman et al. |
| 2009/0117037 A1 | 5/2009 | Davis et al. |
| 2009/0118303 A1 | 5/2009 | Jikyo et al. |
| 2010/0009990 A1 | 1/2010 | Venkataramani et al. |
| 2010/0029615 A1 | 2/2010 | Munchhof et al. |
| 2010/0048414 A1 | 2/2010 | Weaver et al. |
| 2010/0093788 A1 | 4/2010 | Player et al. |
| 2010/0144732 A1 | 6/2010 | Krueger et al. |
| 2010/0203056 A1 | 8/2010 | Irving et al. |
| 2010/0216806 A1 | 8/2010 | Liang et al. |
| 2010/0298290 A1 | 11/2010 | Anand et al. |
| 2010/0298358 A1 | 11/2010 | Lu et al. |
| 2010/0324046 A1 | 12/2010 | Harrington et al. |
| 2011/0271358 A1 | 11/2011 | Freeman et al. |
| 2011/0305691 A1 | 12/2011 | Chafen et al. |
| 2012/0039906 A1 | 2/2012 | Olive |
| 2012/0094971 A1 | 4/2012 | Rusche et al. |
| 2012/0251537 A1 | 10/2012 | Ahmed et al. |
| 2013/0017199 A1 | 1/2013 | Langermann |
| 2013/0045202 A1 | 2/2013 | Irving et al. |
| 2013/0108651 A1 | 5/2013 | Carven et al. |
| 2013/0109843 A1 | 5/2013 | Carven et al. |
| 2013/0230514 A1 | 9/2013 | Langermann et al. |
| 2013/0237580 A1 | 9/2013 | Sasikumar et al. |
| 2013/0280265 A1 | 10/2013 | Rolland et al. |
| 2013/0309250 A1 | 11/2013 | Cogswell et al. |
| 2014/0051680 A1 | 2/2014 | Jacques et al. |
| 2014/0080800 A1 | 3/2014 | Holson et al. |
| 2014/0080802 A1 | 3/2014 | Holson et al. |
| 2014/0335550 A1 | 11/2014 | Zhang et al. |
| 2015/0191427 A1 | 7/2015 | Holson et al. |
| 2015/0368221 A1 | 12/2015 | Holson et al. |
| 2016/0108123 A1 | 4/2016 | Freeman et al. |
| 2016/0251351 A1 | 9/2016 | Holson et al. |
| 2016/0272579 A1 | 9/2016 | Mazitschek et al. |
| 2016/0346240 A1 | 12/2016 | Jandeleit et al. |
| 2016/0347761 A1 | 12/2016 | Holson et al. |
| 2018/0016282 A9 | 1/2018 | Holson et al. |
| 2018/0072671 A1 | 3/2018 | Holson et al. |
| 2018/0099977 A1 | 4/2018 | Holson et al. |
| 2018/0215726 A1 | 8/2018 | Holson et al. |
| 2019/0216754 A1 | 7/2019 | Holson et al. |

FOREIGN PATENT DOCUMENTS

| | | |
|---|---|---|
| DE | 670 584 | 1/1939 |
| DE | 1108213 C | 6/1961 |
| DE | 2163381 | 7/1972 |
| EP | 0 196 005 A1 | 10/1986 |
| EP | 0 199 393 A1 | 10/1986 |
| EP | 0 309 423 | 3/1989 |
| EP | 1 402 888 A1 | 3/2004 |
| EP | 1212422 B1 | 2/2007 |
| EP | 2170959 B1 | 10/2013 |
| GB | 2 079 480 A | 1/1982 |
| GB | 2 086 905 A | 5/1982 |
| JP | S58-53916 A | 3/1983 |
| JP | 3-232868 A | 10/1991 |
| JP | H06-122669 A | 5/1994 |
| JP | 9-503748 A | 4/1997 |
| JP | 9-227495 A | 9/1997 |
| JP | 2000-302765 | 10/2000 |
| JP | 2002-296728 A | 10/2002 |
| JP | 2004-521072 A | 7/2004 |
| JP | 2005-508311 A | 3/2005 |
| JP | 2005-522440 A | 7/2005 |
| JP | 2007-506785 | 3/2007 |
| JP | 2008-502719 | 1/2008 |
| JP | 2008-509075 A | 3/2008 |
| JP | 2008-094847 A | 4/2008 |
| JP | 2009-523726 A | 6/2009 |
| JP | 2009-536615 A | 10/2009 |
| JP | 2010-531359 A | 9/2010 |
| JP | 2011-528039 | 11/2011 |
| JP | 2012-510512 A | 5/2012 |
| JP | 2012-518612 A | 8/2012 |
| JP | 2014-514261 A | 6/2014 |
| JP | 2014-523857 A | 9/2014 |
| JP | 2015-528812 A | 10/2015 |
| TW | 201740943 A | 12/2017 |
| WO | WO 2001/014424 A2 | 3/2001 |
| WO | WO 01/070675 | 9/2001 |
| WO | WO 2002/14311 A2 | 2/2002 |
| WO | WO 02/46181 A2 | 6/2002 |
| WO | WO 03/013484 | 2/2003 |
| WO | WO 2003/066623 A1 | 8/2003 |
| WO | WO 2003/087057 A1 | 10/2003 |
| WO | WO 2004/073599 A2 | 9/2004 |
| WO | WO 2005/025557 | 3/2005 |
| WO | WO 2005/030705 A1 | 4/2005 |
| WO | WO 2005/034880 A2 | 4/2005 |
| WO | WO 2005/066151 A2 | 7/2005 |
| WO | WO 2006/001918 | 1/2006 |
| WO | WO 2006/016680 A1 | 2/2006 |
| WO | WO 2007/087130 A2 | 8/2007 |
| WO | WO 2007/118137 A1 | 10/2007 |
| WO | WO 2008/113255 | 9/2008 |
| WO | WO 2009/002534 A1 | 12/2008 |
| WO | WO 2009/055917 A1 | 5/2009 |
| WO | WO 2009/076234 A2 | 6/2009 |
| WO | WO 2009/104819 A1 | 8/2009 |
| WO | WO 2010/014054 A1 | 2/2010 |
| WO | WO 2010/028192 | 3/2010 |
| WO | WO 2010/065117 A1 | 6/2010 |
| WO | WO 2010/094678 A1 | 8/2010 |
| WO | WO 2010/142426 A1 | 12/2010 |
| WO | WO 2011/009084 A2 | 1/2011 |
| WO | WO 2011/053876 | 5/2011 |
| WO | WO 2012/112447 A2 | 8/2012 |
| WO | WO 2012/118750 A2 | 9/2012 |
| WO | WO 2012/118782 A1 | 9/2012 |
| WO | WO 2012/149540 | 11/2012 |
| WO | WO 2012/155806 A1 | 11/2012 |
| WO | WO 2013/059582 A2 | 4/2013 |
| WO | WO 2013/067391 A1 | 5/2013 |
| WO | 2014/152444 A1 | 9/2014 |
| WO | WO 2015/134973 A1 | 9/2015 |
| WO | 2017/029514 A1 | 2/2017 |

(56) References Cited

FOREIGN PATENT DOCUMENTS

| WO | WO 2017/197140 A1 | 11/2017 |
| --- | --- | --- |
| WO | WO 2018/132391 A1 | 7/2018 |

OTHER PUBLICATIONS

Burger, Isosterism and bioisosterism in drug design. Prog Drug Res. 1991;37:287-371. doi: 10.1007/978-3-0348-7139-6_7.
Canadian Office Action dated Apr. 17, 2018 for Application No. 2,834,548.
Canadian Office Action dated Nov. 19, 2018 for Application No. 2,834,548.
Canadian Office Action for Application No. 2834548 mailed Jul. 15, 2019.
Canadian Office Action for Application No. 2834548 mailed Apr. 8, 2020.
Supplementary European Search Report mailed Apr. 13, 2015 for Application No. EP 12775936.3.
Office Communication mailed May 30, 2016 for Application No. EP 12775936.3.
European Search Report mailed Mar. 4, 2014 for Application No. EP 13194971.1.
Office Communication mailed Jul. 15, 2015 for Application No. EP 13194971.1.
European Communication Pursuant to Article 94(3) EPC dated Nov. 20, 2017 for Application No. 13194971.1.
European Communication mailed Jul. 17, 2018 Application No. 13194971.1.
Japanese Office Action mailed Oct. 14, 2015 for Application No. JP 2014-508179.
Japanese Decision of Rejection dated Jun. 10, 2019 for Application No. JP 2017-212845.
Japanese Pre-appeal Exam Report dated Dec. 25, 2019 for Application No. JP 2017-013512.
International Search Report and Written Opinion mailed Jul. 20, 2012 for Application No. PCT/US2012/035814.
International Preliminary Report on Patentability mailed Nov. 7, 2013 for Application No. PCT/US2012/035814.
Canadian Examination Report mailed Jul. 30, 2019 for Application No. 2,880,117.
Canadian Office Action for Application No. 2880117 mailed Apr. 17, 2020.
European Office Communication for European Application No. 13745773.5 mailed Dec. 21, 2016.
European Communication Pursuant to Article 94(3) EPC dated Mar. 27, 2018, with Office Action Annex for Application No. 13745773.5.
European Communication Pursuant to Article 94(3) EPC dated Feb. 12, 2019, with Office Action Annex for Application No. 13745773.5.
International Search Report and Written Opinion mailed Oct. 22, 2013 for Application No. PCT/US2013/052572.
International Preliminary Report on Patentability mailed Feb. 5, 2015 for Application No. PCT/US2013/052572.
International Search Report and Written Opinion mailed Mar. 13, 2014 for Application No. PCT/US2013/076618.
International Preliminary Report on Patentability mailed Jul. 2, 2015 for Application No. PCT/US2013/076618.
[No Author Listed] Chemical Abstracts STN Database Record for RN 1016518-65-2. Apr. 23, 2008. 1 page.
[No Author Listed] Chemical Abstracts STN Database Record for RN 1039887-48-3. Aug. 20, 2008.
[No Author Listed] Chemical Abstracts STN Database Record for RN 1082133-39-8. Dec. 9, 2008. 3 pages.
[No Author Listed] Chemical Abstracts STN Database Record for RN 1218208-54-8. Apr. 11, 2010. 1 page.
[No Author Listed] Chemical Abstracts STN Database Record for RN 695166-87-1. Jun. 18, 2004. 1 page.
[No Author Listed] Chemical Abstracts STN Database Record for RN 926190-69-4 and 926236-00-2. Mar. 13, 2007.
[No Author Listed] Chemical Abstracts STN Database Record for RN 926217-21-2. Mar. 13, 2007. 1 page.
[No Author Listed] Chemical Abstracts STN Database Record for RN 926231-00-7. Mar. 13, 2007. 1 page.
[No Author Listed] Chemical Abstracts STN Database Record for RN 926250-54-6. Mar. 13, 2007. 1 page.
[No Author Listed] Chemical Abstracts STN Database Record for RN 92659-80-5. Mar. 13, 2007. 1 page.
[No Author Listed] Caplus Accession No. 1914:9447. Document No. 8:9447. Bredt et al., 1-Epicamphor (1-B-camphor). J Chem Soc. 1914;103:2182-2225. 2 pages.
[No Author Listed] Caplus Accession No. 1992:426229. Document No. 117:26229. Lozanova et al., Synthesis and biological activity of 1-(2-hydroxyaryl)-3-benzyl-and 1-(2-hydroxyaryl)-3-pyrrolidinylureas. retrieved on Nov. 19, 2020. 2 pages.
[No Author Listed] Chemical Abstracts STN Database Record for 1218056-74-6. Apr. 11, 2010. 1 page.
[No Author Listed] Chemical Abstracts STN Database Record for RN 1153257-67-0. Jun. 7, 2009. 1 page.
[No Author Listed] Chemical Abstracts STN Database Record for RN 11812848-11-2. Sep. 8, 2009. 1 page.
[No Author Listed] Chemical Abstracts STN Database Record for RN 1257264-39-3. retrieved on Dec. 21, 2020. 3 pages.
[No Author Listed] Chemical Abstracts STN Database Record for RN 644970-51-4. retrieved on Nov. 19, 2020. 2 pages.
[No Author Listed] Chemical Abstracts STN Database Record for RN 737809-68-6 Sep. 2, 2004. 1 page.
[No Author Listed] Chemical Abstracts STN Database Record for RN 926248-07-9. Entered on Mar. 13, 2007.
[No Author Listed], Benzoxazole derivatives. Caplus Accession No. 1983:179360 of JP 58004778; Jan. 11, 1983. 1page.
[No Author Listed], Database Accession No. 341032-95-9. Database Registry Chemical Abstracts Service. Jun. 14, 2001. STN File Casreact: XP002720214. 2 pages.
Abramson et al., Blocking the effects of IL-1 in rheumatoid arthritis protects bone and cartilage. Rheumatology (Oxford). Sep. 2002;41(9):972-80. Review.
Abuchowski et al., Soluble Polymer-Enzyme Adducts. In: Enzymes as Drugs. 1981. Hocenberg et al., Eds. 367-83.
Acharya et al., Rational development of histone deacetylase inhibitors as anticancer agents: a review. Mol Pharmacol. Oct. 2005;68(4):917-32. Epub Jun. 14, 2005. Review.
Adjei et al., Bioavailability of leuprolide following intratracheal administration to beagle dogs. Int J Pharm. Jun. 11, 1990;61:135-44.
Adjei et al., Pulmonary delivery of peptide drugs: effect of particle size on bioavailability of leuprolide acetate in healthy male volunteers. Pharm Res. Jun. 1990;7(6):565-9.
Alberini, Transcription factors in long-term memory and synaptic plasticity. Physiol Rev. Jan. 2009;89(1):121-45. doi: 10.1152/physrev.00017.2008. Review.
Alenghat et al., Nuclear receptor corepressor and histone deacetylase 3 govern circadian metabolic physiology. Nature. Dec. 18, 2008;456(7224):997-1000. doi: 10.1038/nature07541. Epub Nov. 26, 2008.
Antonov et al., Aminolysis of 2(3H)-Benzothiazolone and its derivatives. Fakultet. 1992;80:189-201.
Arts et al., Histone deacetylase inhibitors: from chromatin remodeling to experimental cancer therapeutics. Curr Med Chem. Nov. 2003;10(22):2343-50. Review.
Bannister et al., Regulation of chromatin by histone modifications. Cell Res. Mar. 2011;21(3):381-95. doi: 10.1038/cr.2011.22. Epub Feb. 15, 2011. Review.
Bantscheff et al., Chemoproteomics profiling of HDAC inhibitors reveals selective targeting of HDAC complexes. Nat Biotechnol. Mar. 2011;29(3):255-65. doi: 10.1038/nbt.1759. Epub Jan. 23, 2011.
Barrett et al., Beyond transcription factors: the role of chromatin modifying enzymes in regulating transcription required for memory. Learn Mem. Jun. 26, 2008;15(7):460-7. doi: 10.1101/lm.917508. Print Jul. 2008. Review.
Blanchard et al., Histone deacetylase inhibitors: new drugs for the treatment of inflammatory diseases? Drug Discov Today. Feb. 1, 2005;10(3):197-204. Review.

(56) References Cited

OTHER PUBLICATIONS

Bradner et al., Chemical genetic strategy identifies histone deacetylase 1 (HDAC1) and HDAC2 as therapeutic targets in sickle cell disease. Proc Natl Acad Sci U S A. Jul. 13, 2010;107(28):12617-22. doi: 10.1073/pnas.1006774107. Epub Jun. 28, 2010.
Bradner et al., Chemical phylogenetics of histone deacetylases. Nat Chem Biol. Mar. 2010;6(3):238-243. Epub Sep. 1, 2010. 14 pages.
Braquet et al., Effect of endothelin-1 on blood pressure and bronchopulmonary system of the guinea pig. J Cardiovasc Pharmacol. 1989;13 Suppl 5:S143-6.
Bredt et al., 1-Epicamphor (1-β-camphor). Chemical Abstracts STN Database Record for RN 1914:9447. Oxford and Manchester. J. Chem. Soc. 1914;103:2182-25. Abstract Only.
Bredt et al., 1-Epicamphor (1-β-camphor). J Chem Soc Trans. 1913;103:2182-225.
Broide et al., Distribution of histone deacetylases 1-11 in the rat brain. J Mol Neurosci. 2007;31(1):47-58.
Brukshtus et al., Synthesis of N-acetyl derivatives of 5-and 6-ethoxy-2-methylthiobenzimidazole and their cardiotonic activity. Chem Heterocyclic Compounds. Jun. 1, 1997;33(6):665-71.
Bunn, Pathogenesis and treatment of sickle cell disease. N Engl J Med. Sep. 11, 1997;337(11):762-9. Review.
Burger et al., Is IL-1 a good therapeutic target in the treatment of arthritis? Best Pract Res Clin Rheumatol. Oct. 2006;20(5):879-96. Review.
Capkova et al., Synthesis and structure-activity relationships of second-generation hydroxamate botulinum neurotoxin A protease inhibitors. Bioorganic & Medicinal Chemistry Letters. 2007;10:6463-6466.
Caplus Accession No. 1962:60453. DE 1108213. Feb. 28, 1959. 1 page.
Caplus Accession No. 1982:492321. BE 891537. Apr. 16, 1982. 2 pages.
Cargin et al., Mild memory impairment in healthy older adults is distinct from normal aging. Brain Cogn. 2006;60(2):146-55.
Chang et al., Differential response of cancer cells to HDAC inhibitors trichostatin A and depsipeptide. Br J Cancer. Jan. 3, 2012;106(1):116-25. doi: 10.1038/bjc.2011.532. Epub Dec. 8, 2011.
Chang et al., Synthesis and bioevaluation of novel 3,4,5-trimethoxybenzylbenzimidazole derivatives that inhibit Helicobacter pylori-induced pathogenesis in human gastric epithelial cells. European Journal of Medicinal Chemistry. Feb. 2012;48:244-54.
Charache et al., Effect of hydroxyurea on the frequency of painful crises in sickle cell anemia. Investigators of the Multicenter Study of Hydroxyurea in Sickle Cell Anemia. N Engl J Med. May 18, 1995;332(20):1317-22.
Charton et al., Synthesis and biological evaluation of benzimidazole derivatives as potent AMP-activated protein kinase activators. Bioorg Med Chem. Jul. 1, 2006;14(13):4490-518. Epub Mar. 2, 2006.
Chemical Abstracts STN Database Record for RN 1019377-02-6. May 6, 2008. 1 page.
Chemical Abstracts STN Database Record for RN 1038237-56-7. Aug. 3, 2008. 1 page.
Chemical Abstracts STN Database Record for RN 1095240-42-8. Jan. 22, 2009. 1 page.
Chemical Abstracts STN Database Record for RN 1152996-49-0. Jun. 7, 2009. 1 page.
Chemical Abstracts STN Database Record for RN 1153085-77-8. Jun. 7, 2009. 1 page.
Chemical Abstracts STN Database Record for RN 1154691-98-1. Jun. 9, 2009. 1 page.
Chemical Abstracts STN Database Record for RN 1156303-71-7. Jun. 12, 2009. 1 page.
Chemical Abstracts STN Database Record for RN 1182778-35-3. Sep. 11, 2009. 1 page.
Chemical Abstracts STN Database Record for RN 1262320-49-9. Feb. 8, 2011. 1 page.
Chemical Abstracts STN Database Record for RN 128691-95-2. Aug. 10, 1990. 1 page.
Chemical Abstracts STN Database Record for RN 1350126-66-7. Dec. 7, 2011. 1 page.
Chemical Abstracts STN Database Record for RN 157026-22-7. Aug. 16, 1994. 1 page.
Chemical Abstracts STN Database Record for RN 169604-52-8. Nov. 3, 1995. 1 page.
Chemical Abstracts STN Database Record for RN 22380-13-8. Nov. 16, 1984. 1 page.
Chemical Abstracts STN Database Record for RN 76280-05-2. Nov. 16, 1984. 1 page.
Chemical Abstracts STN Database Record for RN 865837-30-5. Oct. 24, 2005. 1 page.
Chemical Abstracts STN Database Record for RN 926186-52-9. Mar. 13, 2007.
Chemical Abstracts STN Database Record for RN 926189-39-1. Mar. 13, 2007.
Chemical Abstracts STN Database Record for RN 926194-42-5. Mar. 13, 2007. 1 page.
Chemical Abstracts STN Database Record for RN 926196-62-5. Mar. 13, 2007. 1 page.
Chemical Abstracts STN Database Record for RN 926204-50-4. Mar. 13, 2007.
Chemical Abstracts STN Database Record for RN 926206-09-9. Mar. 13, 2007. 1 page.
Chemical Abstracts STN Database Record for RN 926214-21-3. Mar. 13, 2007.
Chemical Abstracts STN Database Record for RN 926217-10-9. Mar. 13, 2007. 1 page.
Chemical Abstracts STN Database Record for RN 926219-65-0. Mar. 13, 2007.
Chemical Abstracts STN Database Record for RN 926219-90-1. Mar. 13, 2007. 1 page.
Chemical Abstracts STN Database Record for RN 926233-05-8. Mar. 13, 2007. 1 page.
Chemical Abstracts STN Database Record for RN 926246-05-1. Mar. 13, 2007. 1 page.
Chemical Abstracts STN Database Record for RN 926247-11-2. Mar. 13, 2007.
Chemical Abstracts STN Database Record for RN 926260-48-2. Mar. 13, 2007.
Chemical Abstracts STN Database Record for RN 926260-89-1. Mar. 13, 2007.
Chemical Abstracts STN Database Record for RN 926264-98-4. Mar. 13, 2007. 1 page.
Chemical Abstracts STN Database Record for RN 926272-49-3. Mar. 13, 2007.
Chemical Abstracts STN Database Record for RN 937607-77-7. Jun. 17, 2007. 1 page.
Chemical Abstracts STN Database Record for RN 937619-64-2. Jun. 17, 2007. 1 page.
Chemical Abstracts STN Database Record for RN 937624-40-3. Jun. 17, 2007. 1 page.
Chemical Abstracts STN Database Record for RN 953731-76-5 Nov. 15, 2007. 1 page.
Chemical Abstracts STN Database Record for RN 953741-80-5. Nov. 15, 2007. 1 page.
Chemical Abstracts STN Database Record for RN 953747-99-4. Nov. 15, 2007. 1 page.
Chou et al., Pimelic diphenylamide 106 is a slow, tight-binding inhibitor of class I histone deacetylases. J Biol Chem. Dec. 19, 2008;283(51):35402-9. doi: 10.1074/jbc.M807045200.
Citrome, Schizophrenia and valproate. Psychopharmacol Bull. 2003;37 Suppl 2:74-88. Review.
Conti et al., Design and synthesis of novel isoxazole-based HDAC inhibitors. Eur J Med Chem. Sep. 2010;45(9):4331-8. doi: 10.1016/j.ejmech.2010.06.035. Epub Jun. 30, 2010.
Dayer et al., Anti-interleukin-1 therapy in rheumatic diseases. Curr Opin Rheumatol. May 2001;13(3):170-6. Review.
Debs et al., Lung-specific delivery of cytokines induces sustained pulmonary and systemic immunomodulation in rats. J Immunol. May 15, 1988;140(10):3482-8.
Dehaene et al., Reward-dependent learning in neuronal networks for planning and decision making. Brain Res. 2000;126:217-29.

(56) References Cited

OTHER PUBLICATIONS

Diao et al., Assembly of substituted 1H-benzimidazoles and 1,3-dihydrobenzimidazol-2-ones via CuI/L-proline catalyzed coupling of aqueous ammonia with 2-iodoacetanilides and 2-iodophenylcarbamates. J Org Chem. Oct. 16, 2009;74(20):7974-7. doi: 10.1021/jo9017183.

Dobrota et al., Expedient access to fused quinoxalines via Dess-Martin periodinane-mediated cyclization of unsymmetrical phenylenediamide derivatives. Tetrahedron Letters 51(9):1262-1264.

D'ydewalle et al., Charcot-Marie-Tooth disease: emerging mechanisms and therapies. Int J Biochem Cell Biol. Aug. 2012;44(8):1299-304. doi: 10.1016/j.biocel.2012.04.020. Epub Apr. 30, 2012. Review.

D'ydewalle et al., HDAC6 at the Intersection of Neuroprotection and Neurodegeneration. Traffic. Jun. 2012;13(6):771-9. doi: 10.1111/j.1600-0854.2012.01347.x. Epub Mar. 26, 2012. Review.

El-Sayed, Reactions of 2-Ethoxycarbonyl-1,3-indandione with Aromatic Amines, Diazonium Salts, and Phenols. Bulletin of the Chemical Society of Japan. 1979(52)3092-3095.

Fischer et al., Cyclin-dependent kinase 5 is required for associative learning. J Neurosci. May 1, 2002;22(9):3700-7.

Fischer et al., Recovery of learning and memory is associated with chromatin remodelling. Nature. May 10, 2007;447(7141):178-82. Epub Apr. 29, 2007.

Fischle et al., Enzymatic activity associated with class II HDACs is dependent on a multiprotein complex containing HDAC3 and SMRT/N-CoR. Mol Cell. Jan. 2002;9(1):45-57.

Frear et al., Metabolism of Cisonilide (cis-2,5-Dimethyl-l Pyrrolidinecarboxanilide) by Excised Leaves and Cell Suspension Cultures of Carrot and Cotton. Pesticide Biochemistry and Physiology. 1975; 5(1): 73-80.

Gante et al., Peptidsynethese, I. Über eine neue Carbonsäureamid-Synthese. Chemiker-Zeitung. 1985; 109(4): 155-156.

Glaser et al., Differential protein acetylation induced by novel histone deacetylase inhibitors. Biochem Biophys Res Commun. Dec. 17, 2004;325(3):683-90.

Govindarajan et al., Reducing HDAC6 ameliorates cognitive deficits in a mouse model for Alzheimer's disease. EMBO Mol Med. Jan. 2013;5(1):52-63. Doi: 10.1002/emmm.201201923. Epub Nov. 26, 2012.

Grundmann et al., Nitrile Oxides. XII. Cycloaliphatic and Alipathic Stable Nitrile Oxides. J Org Chem. Jan. 1, 1969;34(6):2016-8.

Guan et al., HDAC2 negatively regulates memory formation and synaptic plasticity. Nature. May 7, 2009;459(7243):55-60. doi: 10.1038/nature07925.

Guenther et al., A core SMRT corepressor complex containing HDAC3 and TBL1, a WD40-repeat protein linked to deafness. Genes Dev. May 1, 2000;14(9):1048-57.

Hancock et al., HDAC inhibitor therapy in autoimmunity and transplantation. Ann Rheum Dis. Apr. 2012;71 Suppl 2:146-54. doi: 10.1136/annrheumdis-2011-200593. Review.

Hnilicová et al., Histone deacetylase activity modulates alternative splicing. PloS One. Feb. 2, 2011;6(2):e16727. Doi: 10.1371/journal.pone.0016727. 11 pages.

Hubbard et al., Anti-neutrophil-elastase defenses of the lower respiratory tract in alpha 1-antitrypsin deficiency directly augmented with an aerosol of alpha 1-antitrypsin. Ann Intern Med. Aug. 1, 1989;111(3):206-12.

Jochems et al., Antidepressant-like properties of novel HDAC6-selective inhibitors with improved brain bioavailability. Neuropsychopharmacology. Jan. 2014;39(2):389-400. doi: 10.1038/npp.2013.207. Epub Aug. 19, 2013.

Johannessen et al., Valproate: past, present, and future. CNS Drug Rev. 2003 Summer;9(2):199-216. Review.

Kalin et al., Development and therapeutic implications of selective histone deacetylase 6 inhibitors. J Med Chem. Aug. 22, 2013;56(16):6297-313. doi: 10.1021/jm4001659. Epub May 15, 2013. Review.

Karagianni et al., HDAC3: taking the SMRT-N-CoRrect road to repression. Oncogene. Aug. 13, 2007;26(37):5439-49. Review.

Katragadda et al., Hydrophobic effect and hydrogen bonds account for the improved activity of a complement inhibitor, compstatin. J Med Chem. Jul. 27, 2006;49(15):4616-22.

Katsura et al., Studies on antiulcer drugs. II. Synthesis and antiulcer activities of imidazo[1,2-alpha]pyridinyl-2-alkylaminobenzoxazoles and 5,6,7,8-tetrahydroimidazo[1,2-alpha]pyridinyl derivatives. Chem Pharm Bull (Tokyo). Feb. 1992;40(2):371-80.

Kilgore et al., Inhibitors of class 1 histone deacetylases reverse contextual memory deficits in a mouse model of Alzheimer's disease. Neuropsychopharmacology. Mar. 2010;35(4):870-80. doi: 10.1038/npp.2009.197. Epub Dec. 9, 2009.

Kouzarides, Chromatin modifications and their function. Cell. Feb. 23, 2007;128(4):693-705. Review.

Kreutzberger et al., Antiinflammatory Agents, VII: Aroylation of 5-Chlorobenzotriazole [Published in German as Entzündungshemmende Wirkstoffe, 7. Mitt. Aroylierung von 5-Chlorbenzotriazol]. Arch. Pharm. 1980;313(3): 255-259. doi: 10.1002/ardp.19803130311.

Kuhn et al., Stalling of spliceosome assembly at distinct stages by small-molecule inhibitors of protein acetylation and deacetylation. RNA. Jan. 2009;15(1):153-75. doi: 10.1261/rna.1332609. Epub Nov. 24, 2008.

Lane et al., Histone deacetylase inhibitors in cancer therapy. J Clin Oncol. Nov. 10, 2009;27(32):5459-68. doi: 10.1200/JCO.2009.22.1291. Epub Oct. 13, 2009.

Langley et al., Remodeling chromatin and stress resistance in the central nervous system: histone deacetylase inhibitors as novel and broadly effective neuroprotective agents. Curr Drug Targets CNS Neurol Disord. Feb. 2005;4(1):41-50. Review.

Lattal et al., Systemic or intrahippocampal delivery of histone deacetylase inhibitors facilitates fear extinction. Behav Neurosci. Oct. 2007;121(5):1125-31.

Leoni et al., The antitumor histone deacetylase inhibitor suberoylanilide hydroxamic acid exhibits antiinflammatory properties via suppression of cytokines. Proc Natl Acad Sci U S A. Mar. 5, 2002;99(5):2995-3000. Epub Feb. 26, 2002.

Lettre et al., DNA polymorphisms at the BCL11A, HBS1L-MYB, and beta-globin loci associate with fetal hemoglobin levels and pain crises in sickle cell disease. Proc Natl Acad Sci USA. Aug. 19, 2008;105(33):11869-74. doi: 10.1073/pnas.0804799105. Epub Jul. 30, 2008.

Letvin et al., Augmentation of fetal-hemoglobin production in anemic monkeys by hydroxyurea. N Engl J Med. Apr. 5, 1984;310(14):869-73.

Levenson et al., Regulation of histone acetylation during memory formation in the hippocampus. J Biol Chem. Sep. 24, 2004;279(39):40545-59. Epub Jul. 23, 2004.

Li et al., Both corepressor proteins SMRT and N-CoR exist in large protein complexes containing HDAC3. EMBO J. Aug. 15, 2000;19(16):4342-50.

Locock et al., γ-aminobutyric acid(C) (GABA$_C$) selective antagonists derived from the bioisosteric modification of 4-aminocyclopent-1-enecarboxylic acid: amides and hydroxamates. J Med Chem. Jul. 11, 2013;56(13):5626-30. doi: 10.1021/jm4006548. Epub Jun. 27, 2013.

Malvaez et al., Modulation of chromatin modification facilitates extinction of cocaine-induced conditioned place preference. Biol Psychiatry. Jan. 1, 2010;67(1):36-43. doi: 10.1016/j.biopsych.2009.07.032. Epub.

Marks et al., Histone deacetylase inhibitors. Adv Cancer Res. 2004;91:137-68. Review.

Marks et al., Histone deacetylases and cancer: causes and therapies. Nat Rev Cancer. Dec. 2001;1(3):194-202. Review.

Matsushita et al., Smart cleavage reactions: the synthesis of benzimidazoles and benzothiazoles from polymer-bound esters. Tetrahedron Lett. 2004;45(2):313-6.

McKay et al., A bird's-eye view of post-translational modifications in the spliceosome and their roles in spliceosome dynamics. Mol Biosyst. Nov. 2010;6(11):2093-102. doi: 10.1039/c002828b. Epub Jun. 22, 2014. 20 pages.

McQuown et al., HDAC3 is a critical negative regulator of long-term memory formation. J Neurosci. Jan. 12, 2011;31(2):764-74. doi: 10.1523/JNEUROSCI.5052-10.2011.

(56) References Cited

OTHER PUBLICATIONS

Menzel et al., A QTL influencing F cell production maps to a gene encoding a zinc-finger protein on chromosome 2p15. Nat Genet. Oct. 2007;39(10):1197-9. Epub Sep. 2, 2007.

Methot et al., Exploration of the internal cavity of histone deacetylase (HDAC) with selective HDAC1/HDAC2 inhibitors (SHI-1:2). Bioorg Med Chem Lett. Feb. 1, 2008;18(3):973-8. doi: 10.1016/j.bmcl. 2007.12.031. Epub Jan. 7, 2008.

Miller et al., Histone deacetylase inhibitors. J Med Chem. Nov. 20, 2003;46(24):5097-116. Review.

Monfils et al., Extinction-reconsolidation boundaries: key to persistent attenuation of fear memories. Science. May 15, 2009;324(5929):951-5. doi: 10.1126/science.1167975. Epub Apr. 2, 2009.

Namdar et al., Selective inhibition of histone deacetylase 6 (HDAC6) induces DNA damage and sensitizes transformed cells to anticancer agents. Proc Natl Acad Sci U S A. Nov. 16, 2010;107(46):20003-8. doi: 10.1073/pnas.1013754107. Epub Oct. 29, 2010.

Newmark et al., Preparation and properties of adducts of streptokinase-plasmin complex with polyethylene glycol and pluronic polyol F 38. J Appl Biochem. 1982;4:185-9.

O'Malley et al., Virtual medicinal chemistry: in silico pre-docking functional group transformation for discovery of novel inhibitors of botulinum toxin serotype A light chain. Bioorg Med Chem Lett. May 1, 2013;23(9):2505-11. doi: 10.1016/j.bmcl.2013.03.030. Epub Mar. 18, 2013.

Oehme et al., Histone deacetylase 8 in neuroblastoma tumorigenesis. Clin Cancer Res. Jan. 1, 2009;15(1):91-9. doi: 10.1158/1078-0432. CCR-08-0684.

Ogino et al., Syntheses and structure-activity relationships of novel, potent, and selective trans-2-[3-oxospiro[isobenzofuran-1(3H),1'-cyclohexan]-4'-yl]benzimidazole NPY Y5 receptor antagonists. Bioorg Med Chem Lett. Sep. 15, 2008;18(18):4997-5001. doi: 10.1016/j. bmcl.2008.08.021.

Olson et al., Discovery of the first histone deacetylase 6/8 dual inhibitors. J Med Chem. Jun. 13, 2013;56(11):4816-20. doi: 10.1021/ jm400390r. Epub May 29, 2013. Supplementary Information. S1-20.

Park et al., Histone deacetylases 1, 6 and 8 are critical for invasion in breast cancer. Oncol Rep. Jun. 2011;25(6):1677-81. doi: 10.3892/ or.2011.1236. Epub Mar. 28, 2011.

Platt et al., Hydroxyurea enhances fetal hemoglobin production in sickle cell anemia. J Clin Invest. Aug. 1984;74(2):652-6.

Rai et al., Two new pimelic diphenylamide HDAC inhibitors induce sustained frataxin upregulation in cells from Friedreich's ataxia patients and in a mouse model. PLoS One. Jan. 21, 2010;5(1):e8825. doi: 10.1371/journal.pone.0008825.

Rivieccio et al., HDAC6 is a target for protection and regeneration following injury in the nervous system. Proc Natl Acad Sci U S A. Nov. 17, 2009;106(46):19599-604. doi: 10.1073/pnas.0907935106. Epub Nov. 2, 2009.

Roozendaal et al., Membrane-associated glucocorticoid activity is necessary for modulation of long-term memory via chromatin modification. J Neurosci. Apr. 7, 2010;30(14):5037-46. doi: 10.1523/ JNEUROSCI.5717-09.2010.

Sam et al., Reaction of 3-(chloroalkyl)-2-benzoxazolinones with amines: formation of 3-(aminoalkyl)-2-benzoxazolinones and 5-substituted-2,3,4,5-tetrahydro-1,5-benzoxazepines. J Pharm Sci. Sep. 1971;60(9):1370-5. doi: 10.1002/jps.2600600918.

Sankaran et al., Developmental and species-divergent globin switching are driven by BCL11A. Nature. Aug. 27, 2009;460(7259):1093-7. doi: 10.1038/nature08243. Epub Aug. 5, 2009.

Sankaran et al., Human fetal hemoglobin expression is regulated by the developmental stage-specific repressor BCL11A. Science. Dec. 19, 2008;322(5909):1839-42. doi: 10.1126/science.1165409. Epub Dec. 4, 2008.

Schultz et al., Kinetics and comparative reactivity of human class I and class IIb histone deacetylases. Biochemistry. Aug. 31, 2004;43(34):11083-91.

Smith et al., Pulmonary deposition and clearance of aerosolized alpha-1-proteinase inhibitor administered to dogs and to sheep. J Clin Invest. Oct. 1989;84(4):1145-54.

Song et al., Synthesis of New Crown Ethers Containing Appended Pyridine, 10-hydroxybenzoquinoline, 8-hydroxyquinoline and 2-amino-1-hydroxybiphenyl Sidearms. Supramolecular Chemistry. 2002;14(2-3):263-269.

Stefanko et al., Modulation of long-term memory for object recognition via HDAC inhibition. Proc Natl Acad Sci U S A. Jun. 9, 2009;106(23):9447-52. doi: 10.1073/pnas.0903964106. Epub May 26, 2009.

Steinberg et al., Effect of hydroxyurea on mortality and morbidity in adult sickle cell anemia: risks and benefits up to 9 years of treatment. JAMA. Apr. 2, 2003;289(13):1645-51. Erratum in: JAMA. Aug. 13, 2003;290(6):756.

Steinberg et al., Management of sickle cell disease. N Engl J Med. Apr. 1, 1999;340(13):1021-30. Review.

Stohandl et al., Study of Solvolysis Mechanism of Some Ureas Derived From 2-Benxoxazolone. Collection of Czechoslovak Chemical Communications. 1979; 44(6):1790-1798.

Suuronen et al., Regulation of microglial inflammatory response by histone deacetylase inhibitors. J Neurochem. Oct. 2003;87(2):407-16.

Tsankova et al., Sustained hippocampal chromatin regulation in a mouse model of depression and antidepressant action. Nat Neurosci. Apr. 2006;9(4):519-25. Epub Feb. 26, 2006.

Turconi et al., Synthesis of a New Class of 2,3-Dihydro-2-oxo-1H-benzimidazole-1-carboxylic Acid Derivatives as Highly Potent 5-HT3 Receptor Antagonists. J Med Chem. 1990;33:2101-8.

Uda et al., Genome-wide association study shows BCL11A associated with persistent fetal hemoglobin and amelioration of the phenotype of beta-thalassemia. Proc Natl Acad Sci U S A. Feb. 5, 2008;105(5):1620-5. doi: 10.1073/pnas.0711566105. Epub Feb. 1, 2008.

Vecsey et al., Histone deacetylase inhibitors enhance memory and synaptic plasticity via CREB:CBP-dependent transcriptional activation. J Neurosci. Jun. 6, 2007;27(23):6128-40.

Wagner et al., An Isochemogenic Set of Inhibitors To Define the Therapeutic Potential of Histone Deacetylases in β-Cell Protection. ACS Chem Biol. Feb. 19, 2016;11(2):363-74. doi: 10.1021/acschembio. 5b00640.

Wagner et al., Potent and selective inhibition of histone deacetylase 6 (HDAC6) does not require a surface-binding motif. J Med Chem. Feb. 28, 2013;56(4):1772-6. doi: 10.1021/jm301355j. Epub Feb. 18, 2013.

Wagner et al., Small molecule inhibitors of zinc-dependent histone deacetylases. Neurotherapeutics. Oct. 2013;10(4):589-604. doi: 10.1007/ s13311-013-0226-1.

Weïwer et al., Therapeutic potential of isoform selective HDAC inhibitors for the treatment of schizophrenia. Future Med Chem. Sep. 2013;5(13):1491-508. doi: 10.4155/fmc.13.141.

Xiong et al., HDAC6 mutations rescue human tau-induced microtubule defects in *Drosophila*. Proc Natl Acad Sci U S A. Mar. 19, 2013;110(12):4604-9. doi: 10.1073/pnas.1207586110. Epub Mar. 4, 2013. 6 pages.

International Search Report and Written Opinion mailed Jun. 21, 2019 for Application No. PCT/US2019/013375.

Chen et al., Combined deletion of Xrcc4 and Trp53 in mouse germinal center B cells leads to novel B cell lymphomas with clonal heterogeneity. J Hematol Oncol. Jan. 7, 2016;9:2. doi: 10.1186/ s13045-015-0230-5.

Coleman et al., Cytogenetic analysis of the bipotential murine pre-B cell lymphoma, P388, and its derivative macrophage-like tumor, P388D1, using SKY and CGH. Leukemia. Oct. 1999;13(10):1592-600.

Deng et al., HDAC3 Inhibition Upregulates PD-L1 Expression in B-Cell Lymphomas and Augments the Efficacy of Anti-PD-L1 Therapy. Mol Cancer Ther. May 2019;18(5):900-908. doi: 10.1158/ 1535-7163.MCT-18-1068. Epub Mar. 1, 2019.

Dunn et al., Epigenetics and immunotherapy: The current state of play. Mol Immunol. Jul. 2017;87:227-239. doi: 10.1016/j.molimm. 2017.04.012. Epub May 14, 2017.

(56) References Cited

OTHER PUBLICATIONS

Jiang et al., CREBBP Inactivation Promotes the Development of HDAC3-Dependent Lymphomas. Cancer Discov. Jan. 2017;7(1):38-53. doi: 10.1158/2159-8290.CD-16-0975. Epub Oct. 12, 2016.
Mondello et al., Selective inhibition of HDAC3 targets synthetic vulnerabilities and activates immune surveillance in lymphoma. Cancer Discov. Jan. 8, 2020. pii: CD-19-0116. doi: 10.1158/2159-8290.CD-19-0116, [Epub ahead of print], 52 pages.
Wrangle et al., Alterations of immune response of Non-Small Cell Lung Cancer with Azacytidine. Oncotarget. Nov. 2013;4(11):2067-79. doi: 10.18632/oncotarget.1542.
Khushalani et al., A phase I trial of panobinostat with ipilimumab in advanced melanoma. Journal of Clinical Oncology. May 2017; 35(15): 9547-9547. DOI: 10.1200/JCO.2017.35.15_suppl.9547. Accessed: https://ascopubs.org/doi/abs/10.1200/JCO.2017.35.15_suppl.9547.
Bobrowicz et al., HDAC Inhibitors as Potential New Agents Improving the Efficacy of Monoclonal Antibodies. Blood. 2014; 124 (21): 3641-44. https://doi.org/10.1182/blood.V124.21.3641.3641.
Chen et al., Research Progress in Histone Deacetylase Inhibitors and Tumor Therapy. Chongqing Medicine. 2017; 46(30): 4280-4283.
Skyjing, Epigenetic Principles, Technology and Practice. Shanghai Science and Technology Press, eds. Published Dec. 31, 2006. p. 207.

\* cited by examiner

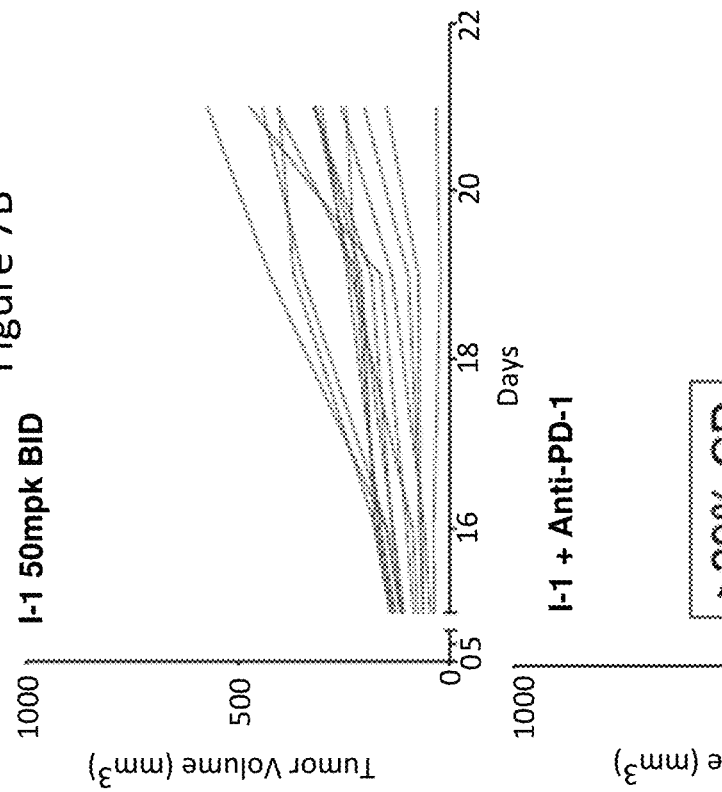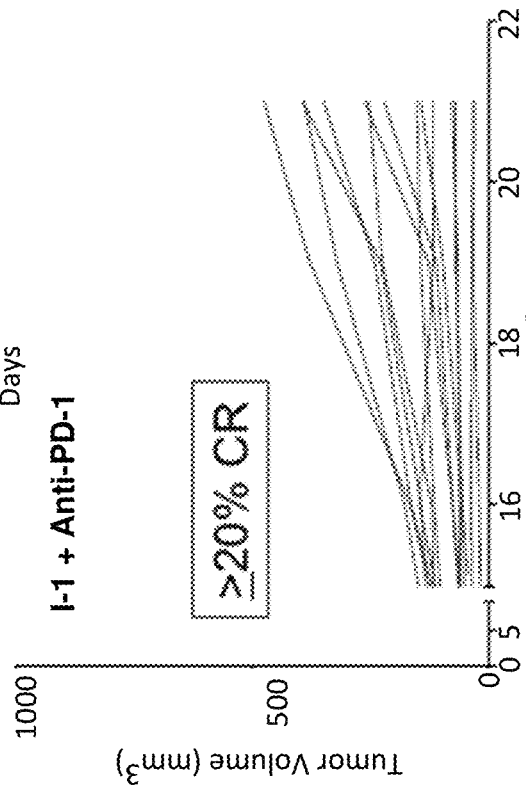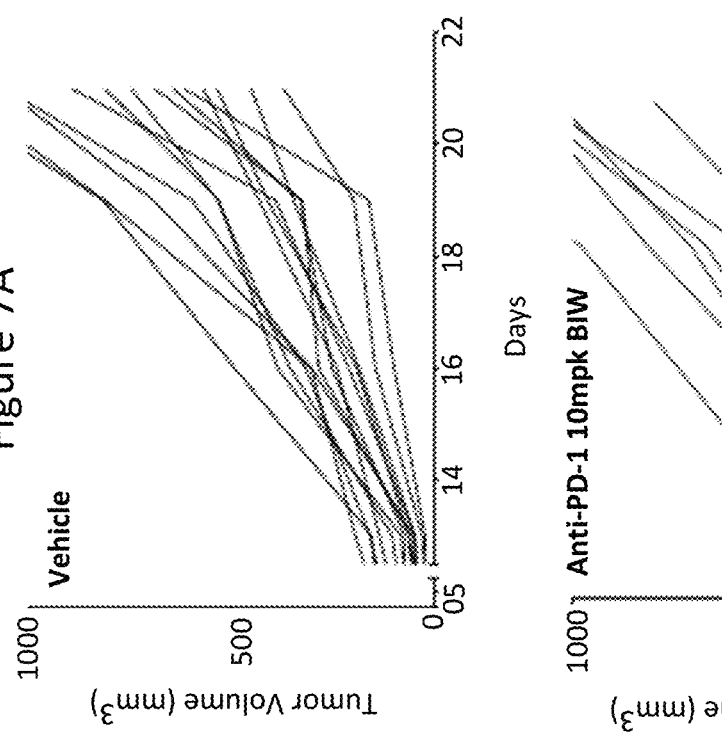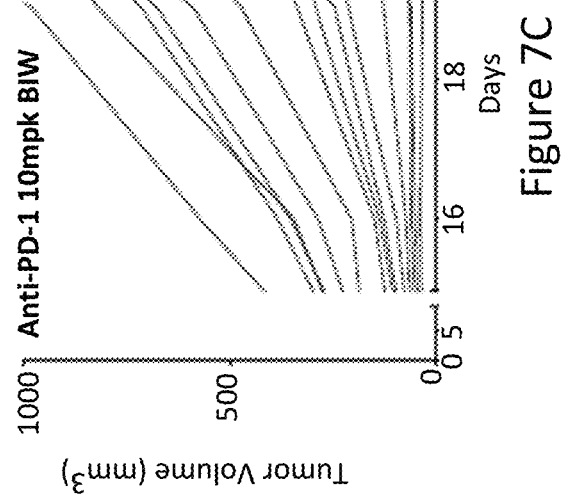

COMBINATION OF A SELECTIVE HISTONE DEACETYLASE 3 (HDAC3) INHIBITOR AND AN IMMUNOTHERAPY AGENT FOR THE TREATMENT OF CANCER

RELATED APPLICATION

The present application claims priority under 35 U.S.C. § 119(e) to U.S. provisional application, U.S. Ser. No. 62/616,831, filed Jan. 12, 2018, which is incorporated herein by reference.

BACKGROUND OF INVENTION

While treatment of cancer has improved in the last 30 years, effective treatment remains challenging for many cancers, especially those cancers that induce immune suppression which may limit or inhibit effective treatment. There remains a need to develop cancer treatments that are more effective, such as combination therapies that harness the immune system of a patient to attack the cancer.

SUMMARY OF THE INVENTION

Aspects of the disclosure relate to methods and compositions (e.g., pharmaceutical compositions) for treatment of cancer. As described herein, selective histone deacetylase 3 (HDAC3) inhibitors were shown to be effective at increasing major histocompatibility complex (MHC) class II expression levels. Additionally, combinations of selective HDAC3 inhibitors and immune checkpoint inhibitors were shown to be more effective than either inhibitor used alone to treat certain types of cancers. Without wishing to be bound by theory, in some embodiments, the selective HDAC3 inhibitors may increase MHC II antigen presentation, and the immune checkpoint inhibitor effectiveness may depend on the level of MHC II antigen presentation such that increased antigen presentation from the selective HDAC3 inhibitor increases the effectiveness of the immune checkpoint inhibitor. Accordingly, in some embodiments, a combination of a selective HDAC3 inhibitor that increases MHC class II expression levels and an immunotherapy agent that increases an immune response to an MHC class II antigen are useful to treat cancer.

In one aspect, provided herein are pharmaceutical compositions for use in treating cancer in a subject in need thereof comprising:
a selective histone deacetylase 3 (HDAC3) inhibitor, wherein the selective HDAC3 inhibitor is more active for inhibiting HDAC3 than for inhibiting a histone deacetylase that is not HDAC3; and
optionally a pharmaceutically acceptable excipient;
wherein:
the amount of the selective HDAC3 inhibitor is effective for increasing expression of a major histocompatibility complex (MHC) class II protein in at least one of the cancer cells;
the subject in need thereof has been administered an immunotherapy agent; and
the combined amount of the selective HDAC3 inhibitor and the immunotherapy agent is effective for treating the cancer.

In another aspect, provided herein are pharmaceutical compositions for use in treating cancer in a subject in need thereof comprising:
an immunotherapy agent; and
optionally a pharmaceutically acceptable excipient;
wherein:
the subject in need thereof has been administered with a selective histone deacetylase 3 (HDAC3) inhibitor, wherein the selective HDAC3 inhibitor is more active for inhibiting HDAC3 than for inhibiting a histone deacetylase that is not HDAC3;
the amount of the selective HDAC3 inhibitor is effective for increasing expression of an MHC class II protein in at least one of the cancer cells;
and
the combined amount of the selective HDAC3 inhibitor and the immunotherapy agent is effective for treating the cancer.

In another aspect, provided herein are kits comprising:
a first container comprising a selective histone deacetylase 3 (HDAC3) inhibitor, wherein the selective HDAC3 inhibitor is more active for inhibiting HDAC3 than for inhibiting a histone deacetylase that is not HDAC3, and wherein the amount of the selective HDAC3 inhibitor is effective for increasing expression of an MHC class II protein in at least one of cancer cells;
a second container comprising an immunotherapy agent; and
instructions for using the selective HDAC3 inhibitor and the immunotherapy agent.

In another aspect, provided herein are methods of treating cancer in a subject in need thereof comprising:
administering a selective histone deacetylase 3 (HDAC3) inhibitor to the subject in need thereof, wherein the selective HDAC3 inhibitor is more active for inhibiting HDAC3 than for inhibiting a histone deacetylase that is not HDAC3; and
administering an immunotherapy agent to the subject in need thereof;
wherein:
the amount of the selective HDAC3 inhibitor is effective for increasing expression of an MHC class II protein in at least one of the cancer cells;
the step of administering the selective HDAC3 inhibitor is prior to, concurrently with, or subsequent to the step of administering the immunotherapy agent; and
the combined amount of the selective HDAC3 inhibitor and the immunotherapy agent is effective for treating the cancer.

In another aspect, provided herein are methods of treating cancer in a subject in need thereof comprising administering a selective histone deacetylase 3 (HDAC3) inhibitor to the subject in need thereof, wherein the selective HDAC3 inhibitor is more active for inhibiting HDAC3 than for inhibiting a histone deacetylase that is not HDAC3;
wherein:
the subject in need thereof has been administered with an immunotherapy agent;
the amount of the selective HDAC3 inhibitor is effective for increasing expression of an MHC class II protein in at least one of the cancer cells;
and
the combined amount of the selective HDAC3 inhibitor and the immunotherapy agent is effective for treating the cancer.

In another aspect, provided herein are methods of treating cancer in a subject in need thereof comprising administering an immunotherapy agent to the subject in need thereof, wherein:
the subject in need thereof has been administered with a selective histone deacetylase 3 (HDAC3) inhibitor, wherein the selective HDAC3 inhibitor is more active for inhibiting HDAC3 than for inhibiting a histone deacetylase that is not HDAC3;

the amount of the selective HDAC3 inhibitor is effective for increasing expression of an MHC class II protein in at least one of the cancer cells; and the combined amount of the selective HDAC3 inhibitor and the immunotherapy agent is effective for treating the cancer.

In another aspect, provided herein are methods of inhibiting proliferation of cancer cells or inducing death of cancer cells in a subject in need thereof comprising:

administering a selective histone deacetylase 3 (HDAC3) inhibitor to the subject in need thereof, wherein the selective HDAC3 inhibitor is more active for inhibiting HDAC3 than for inhibiting a histone deacetylase that is not HDAC3; and administering an immunotherapy agent to the subject in need thereof;

wherein:

the amount of the selective HDAC3 inhibitor is effective for increasing expression of an MHC class II protein in at least one of the cancer cells;

the step of administering the selective HDAC3 inhibitor is prior to, concurrently with, or subsequent to the step of administering the immunotherapy agent; and the combined amount of the selective HDAC3 inhibitor and the immunotherapy agent is effective for inhibiting proliferation of the cancer cells or inducing death of the cancer cells.

In another aspect, provided herein are methods of inhibiting proliferation of cancer cells or inducing death of cancer cells in a subject in need thereof comprising administering a selective histone deacetylase 3 (HDAC3) inhibitor to the subject in need thereof, wherein the selective HDAC3 inhibitor is more active for inhibiting HDAC3 than for inhibiting a histone deacetylase that is not HDAC3;

wherein:

the subject in need thereof has been administered with an immunotherapy agent;

the amount of the selective HDAC3 inhibitor is effective for increasing expression of an MHC class II protein in at least one of the cancer cells; and the combined amount of the selective HDAC3 inhibitor and the immunotherapy agent is effective for inhibiting proliferation of the cancer cells or inducing death of the cancer cells.

In another aspect, provided herein are methods of inhibiting proliferation of cancer cells or inducing death of cancer cells in a subject in need thereof comprising administering an immunotherapy agent to the subject in need thereof;

wherein:

the subject in need thereof has been administered with a selective histone deacetylase 3 (HDAC3) inhibitor, wherein the selective HDAC3 inhibitor is more active for inhibiting HDAC3 than for inhibiting a histone deacetylase that is not HDAC3;

the amount of the selective HDAC3 inhibitor is effective for increasing expression of an MHC class II protein in at least one of the cancer cells; and the combined amount of the selective HDAC3 inhibitor and the immunotherapy agent is effective for inhibiting proliferation of the cancer cells or inducing death of the cancer cells.

In certain embodiments, the cancer is kidney cancer, melanoma, breast cancer, non-small cell lung cancer, non-Hodgkin lymphoma, head and neck cancer, Hodgkin's lymphoma, or bladder cancer.

In certain embodiments, the selective HDAC3 inhibitor is at least 5-fold more active in an in vitro enzymatic inhibition assay for inhibiting HDAC3 than for inhibiting a histone deacetylase that is not HDAC3.

In certain embodiments, the amount of the immunotherapy agent is effective for increasing an immune response to an MHC class II antigen in the subject in need thereof. In certain embodiments, the immunotherapy agent is an immune checkpoint inhibitor.

Definitions

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

In certain embodiments, a compound described herein is a chemotherapeutic agent. In certain embodiments, a compound described herein is a mutagenic agent. In certain embodiments, a compound described herein is an immune checkpoint inhibitor. Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, IN 1972). The invention additionally encompasses compounds as individual isomers substantially free of other isomers, and alternatively, as mixtures of various isomers.

In a formula, the bond ⌇ is a single bond, the dashed line - - - is a single bond or absent, and the bond ═ or ═ is a single or double bond.

Unless otherwise provided, a formula depicted herein includes compounds that do not include isotopically enriched atoms and also compounds that include isotopically enriched atoms. Compounds that include isotopically enriched atoms may be useful as, for example, analytical tools, and/or probes in biological assays.

When a range of values is listed, it is intended to encompass each value and subrange within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-12}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu or s-Bu), unsubstituted isobutyl (i-Bu)). In certain embodiments, the alkyl group is a substituted $C_{1-12}$ alkyl (such as substituted $C_{1-6}$ alkyl, e.g., —$CH_2F$, —$CHF_2$, —$CF_3$, —$CH_2CH_2F$, —$CH_2CHF_2$, —$CH_2CF_3$, or benzyl (Bn)).

The term "haloalkyl" is a substituted alkyl group, wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —$CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C=C double bond for which the stereochemistry is not specified (e.g., —CH=CHCH$_3$,

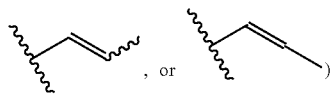

, or

)

may be in the (E)- or (Z)-configuration.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and for 2 heteroatoms within the parent chain ("hetero$C_{2-4}$ alkenyl"). In some embodiments, a heteroalkenyl group has 2 to 3 carbon atoms, at least one double bond, and 1 heteroatom within the parent chain ("hetero$C_{2-3}$ alkenyl"). In some embodiments, a heteroalkenyl group has 2 to 6 carbon atoms, at least one double bond, and 1 or 2 heteroatoms within the parent chain ("hetero$C_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{2-10}$ alkenyl. In certain embodiments, the heteroalkenyl group is a substituted hetero$C_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_2$-4 alkynyl groups include ethynyl ($C_2$), 1-propynyl ($C_3$), 2-propynyl ($C_3$), 1-butynyl ($C_4$), 2-butynyl ($C_4$), and the like. Examples of $C_{2-6}$ alkynyl groups include the aforementioned $C_2$-4 alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and for 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{2-10}$ alkynyl. In certain embodiments, the heteroalkynyl group is a substituted hetero$C_{2-10}$ alkynyl.

The term "carbocyclyl" or "carbocyclic" refers to a radical of a nonaromatic cyclic hydrocarbon group having from 3 to 14 ring carbon atoms ("$C_{3-14}$ carbocyclyl") and zero heteroatoms in the nonaromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_3$-14 carbocyclyl. In certain embodiments, the carbocyclyl group is a substituted $C_3$-14 carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl. In certain embodiments, the carbocyclyl includes 0, 1, or 2 C=C double bonds in the carbocyclic ring system, as valency permits.

The term "heterocyclyl" or "heterocyclic" refers to a radical of a 3 to 14 membered nonaromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl. In certain embodiments, the heterocyclyl is substituted or unsubstituted, 3- to 7-membered, monocyclic heterocyclyl, wherein 1, 2, or 3 atoms in the heterocyclic ring system are independently oxygen, nitrogen, or sulfur, as valency permits.

In some embodiments, a heterocyclyl group is a 5-10 membered nonaromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered nonaromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered nonaromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include azirdinyl, oxiranyl, and thiiranyl. Exemplary 4-membered heterocyclyl groups containing 1 heteroatom include azetidinyl, oxetanyl, and thietanyl. Exemplary 5-membered heterocyclyl groups containing 1 heteroatom include tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include dioxolanyl, oxathiolanyl and dithiolanyl. Exemplary 5-membered heterocyclyl groups containing 3 heteroatoms include triazolinyl, oxadiazolinyl, and thiadiazolinyl. Exemplary 6-membered heterocyclyl groups containing 1 heteroatom include piperidinyl, tetrahydropyranyl, dihydropyridinyl, and thianyl. Exemplary 6-membered heterocyclyl groups containing 2 heteroatoms include piperazinyl, morpholinyl, dithianyl, and dioxanyl. Exemplary 6-membered heterocyclyl groups containing 3 heteroatoms include triazinyl. Exemplary 7-membered heterocyclyl groups containing 1 heteroatom include azepanyl, oxepanyl and thiepanyl. Exemplary 8-membered heterocyclyl groups containing 1 heteroatom include azocanyl, oxecanyl and thiocanyl. Exemplary bicyclic heterocyclyl groups include indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 r electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_6$-14 aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). In certain embodiments, the heteroaryl is substituted or unsubstituted, 5- or 6-membered, monocyclic heteroaryl, wherein 1, 2, 3, or 4 atoms in the heteroaryl ring system are independently oxygen, nitrogen, or sulfur. In certain embodiments, the heteroaryl is substituted or unsubstituted, 9- or 10-membered, bicyclic heteroaryl, wherein 1, 2, 3, or 4 atoms in the heteroaryl ring system are independently oxygen, nitrogen, or sulfur.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include pyrrolyl, furanyl, and thiophenyl. Exemplary 5-membered heteroaryl groups containing 2 heteroatoms include imidazolyl, pyrazolyl, oxazolyl, isoxazolyl, thiazolyl, and isothiazolyl. Exemplary 5-membered heteroaryl groups containing 3 heteroatoms include triazolyl, oxadiazolyl, and thiadiazolyl. Exemplary 5-membered heteroaryl groups containing 4 heteroatoms include tetrazolyl. Exemplary 6-membered heteroaryl groups containing 1 heteroatom include pyridinyl. Exemplary 6-membered heteroaryl groups containing 2 heteroatoms include pyridazinyl, pyrimidinyl, and pyrazinyl. Exemplary 6 membered heteroaryl groups containing 3 or 4 heteroatoms include triazinyl and tetrazinyl, respectively. Exemplary 7-membered heteroaryl groups containing 1 heteroatom include azepinyl, oxepinyl, and thiepinyl. Exemplary 5,6-bicyclic heteroaryl groups include indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include naphthyridinyl, pteridinyl, quinolinyl, isoquinolinyl, cinnolinyl, quinoxalinyl, phthalazinyl, and quinazolinyl. Exemplary tricyclic heteroaryl groups include phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group substituted by a heteroaryl group, wherein the point of attachment is on the alkyl moiety.

The term "unsaturated bond" refers to a double or triple bond.

The term "unsaturated" or "partially unsaturated" refers to a moiety that includes at least one double or triple bond.

The term "saturated" or "fully saturated" refers to a moiety that does not contain a double or triple bond, i.e., the moiety only contains single bonds.

Affixing the suffix "ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{cc}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{2-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X is a counterion.

In certain embodiments, the carbon atom substituents are independently halogen, substituted (e.g., substituted with one or more halogen) or unsubstituted C$_{1-6}$ alkyl, —OR$^{aa}$, —SR$^{aa}$, —N(R$^{bb}$)$_2$, —CN, —SCN, —NO$_2$, —C(=O)R$^{aa}$, —CO$_2$R$^{aa}$, —C(=O)N(R$^{bb}$)$_2$, —OC(=O)R$^{aa}$, —OCO$_2$R$^{aa}$, —OC(=O)N(R$^{bb}$)$_2$, —NR$^{bb}$C(=O)R$^{aa}$, —NR$^{bb}$CO$_2$R$^{aa}$, or —NR$^{bb}$C(=O)N(R$^{bb}$)$_2$. In certain embodiments, the carbon atom substituents are independently halogen, substituted (e.g., substituted with one or more halogen) or unsubstituted C$_{1-6}$ alkyl, —OR$^{aa}$, —SR$^{aa}$, —N(R$^{bb}$)$_2$, —CN, —SCN, —NO$_2$, —C(=O)R$^{aa}$, —CO$_2$R$^{aa}$, —C(=O)N(R$^{bb}$)$_2$, —OC(=O)R$^{aa}$, —OCO$_2$R$^{aa}$, —OC(=O)N(R$^{bb}$)$_2$, —NR$^{bb}$C(=O)R$^{aa}$, —NR$^{bb}$CO$_2$R$^{aa}$, or —NR$^{bb}$C(=O)N(R$^{bb}$)$_2$, wherein R$^{aa}$ is hydrogen, substituted (e.g., substituted with one or more halogen) or unsubstituted C$_{1-6}$ alkyl, an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom; and each R$^{bb}$ is independently hydrogen, substituted (e.g., substituted with one or more halogen) or unsubstituted C$_{1-6}$ alkyl, or a nitrogen protecting group (e.g., Bn, Boc, Cbz, Fmoc, trifluoroacetyl, triphenylmethyl, acetyl, or Ts). In certain embodiments, the carbon atom substituents are independently halogen, substituted (e.g., substituted with one or more halogen) or unsubstituted C$_{1-6}$ alkyl, —OR$^{aa}$, —SR$^{aa}$, —N(R$^{bb}$)$_2$, —CN, —SCN, or —NO$_2$. In certain embodiments, the carbon atom substituents are independently halogen, substituted (e.g., substituted with one or more halogen moieties) or unsubstituted C$_{1-6}$ alkyl, —OR$^{aa}$, —SR$^{aa}$, —N(R$^{bb}$)$_2$, —CN, —SCN, or —NO$_2$, wherein R$^{aa}$ is hydrogen, substituted (e.g., substituted with one or more halogen) or unsubstituted C$_{1-6}$ alkyl, an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom; and each R$^{bb}$ is independently hydrogen, substituted (e.g., substituted with one or more halogen) or unsubstituted C$_{1-6}$ alkyl, or a nitrogen protecting group (e.g., Bn, Boc, Cbz, Fmoc, trifluoroacetyl, triphenylmethyl, acetyl, or Ts).

In certain embodiments, the molecular weight of a carbon atom substituent is lower than 250, lower than 200, lower than 150, lower than 100, or lower than 50 g/mol. In certain embodiments, a carbon atom substituent consists of carbon, hydrogen, fluorine, chlorine, bromine, iodine, oxygen, sulfur, nitrogen, and/or silicon atoms. In certain embodiments, a carbon atom substituent consists of carbon, hydrogen, fluorine, chlorine, bromine, iodine, oxygen, sulfur, and/or nitrogen atoms. In certain embodiments, a carbon atom substituent consists of carbon, hydrogen, fluorine, chlorine, bromine, and/or iodine atoms. In certain embodiments, a carbon atom substituent consists of carbon, hydrogen, fluorine, and/or chlorine atoms.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein.

The term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —SR$^{aa}$, —S=SR$^{cc}$, —SC(=S)SR$^{aa}$, —SC(=O)SR$^{aa}$, —SC(=O)OR$^{aa}$, and —SC(=O)R$^{aa}$, wherein R$^{aa}$ and R$^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a mono-substituted amino or a disubstituted amino group.

The term "sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

The term "sulfinyl" refers to the group —S(=O)R$^{aa}$, wherein R$^a$ is as defined herein.

The term "carbonyl" refers a group wherein the carbon directly attached to the parent molecule is sp$^2$ hybridized, and is substituted with an oxygen, nitrogen or sulfur atom, e.g., a group selected from ketones (—C(=O)R$^{aa}$), carboxylic acids (—CO$_2$H), aldehydes (—CHO), esters (—CO$_2$R$^{aa}$, —C(=O)SR$^{aa}$, —C(=S)SR$^{aa}$), amides (—C(=O)N(R$^{bb}$)$_2$, —C(=O)NR$^{bb}$SO$_2$R$^{aa}$, —C(=S)N(R$^{bb}$)$_2$), and imines (—C(=NR$^{bb}$)R$^{aa}$, —C(=NR$^{bb}$)OR$^{aa}$), —C(=NR$^{bb}$)N(R$^{bb}$)$_2$), wherein R$^{aa}$ and R$^{bb}$ are as defined herein.

The term "silyl" refers to the group —Si(R$^{aa}$)$_3$, wherein R$^{aa}$ is as defined herein.

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the nitrogen atom substituents are independently substituted (e.g., substituted with one or more halogen) or unsubstituted C$_{1-6}$ alkyl, —C(=O)R$^{aa}$, —CO$_2$R$^{aa}$, —C(=O)N(R$^{bb}$)$_2$, or a nitrogen protecting group. In certain embodiments, the nitrogen atom substituents are independently substituted (e.g., substituted with one or more halogen) or unsubstituted C$_{1-6}$ alkyl, —C(=O)R$^{aa}$, —CO$_2$R$^{aa}$, —C(=O)N(R$^{bb}$)$_2$, or a nitrogen protecting group, wherein R$^{aa}$ is hydrogen, substituted (e.g., substituted with one or more halogen) or unsubstituted C$_{1-6}$ alkyl, or an oxygen protecting group when attached to an oxygen atom; and each R$^{bb}$ is independently hydrogen, substituted (e.g., substituted with one or more halogen) or unsubstituted C$_{1-6}$ alkyl, or a nitrogen protecting group. In certain embodiments, the nitrogen atom substituents are independently substituted (e.g., substituted with one or more halogen) or unsubstituted C$_{1-6}$ alkyl or a nitrogen protecting group.

In certain embodiments, the substituent present on the nitrogen atom is an nitrogen protecting group (also referred to herein as an "amino protecting group"). Nitrogen protecting groups include —OH, —OR$^{aa}$, —N(R$^{cc}$)$_2$, —C(=O)R$^{aa}$, —C(=O)N(R$^{cc}$)$_2$, —CO$_2$R", —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., —S(=O)$_2$R$^{aa}$) include p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pme), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, a nitrogen protecting group is Bn, Boc, Cbz, Fmoc, trifluoroacetyl, triphenylmethyl, acetyl, or Ts.

In certain embodiments, the oxygen atom substituents are independently substituted (e.g., substituted with one or more halogen) or unsubstituted $C_{1-6}$ alkyl, —C(=O)R$^{aa}$, —CO$_2$R$^{aa}$, —C(=O)N(R$^{bb}$)$_2$, or an oxygen protecting group. In certain embodiments, the oxygen atom substituents are independently substituted (e.g., substituted with one or more halogen) or unsubstituted $C_{1-6}$ alkyl, —C(=O)R$^{aa}$, —CO$_2$R$^{aa}$, —C(=O)N(R$^{bb}$)$_2$, or an oxygen protecting group, wherein R$^{aa}$ is hydrogen, substituted (e.g., substituted with one or more halogen) or unsubstituted $C_{1-6}$ alkyl, or an oxygen protecting group when attached to an oxygen atom; and each R$^{bb}$ is independently hydrogen, substituted (e.g., substituted with one or more halogen) or unsubstituted $C_{1-6}$ alkyl, or a nitrogen protecting group. In certain embodiments, the oxygen atom substituents are independently substituted (e.g., substituted with one or more halogen) or unsubstituted $C_{1-6}$ alkyl or an oxygen protecting group.

In certain embodiments, the substituent present on an oxygen atom is an oxygen protecting group (also referred to herein as an "hydroxyl protecting group"). Oxygen protecting groups include —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy) ethyl, 1-methyl-1-methoxyethyl, 1-methyl-1-benzyloxyethyl, 1-methyl-1-benzyloxy-2-fluoroethyl, 2,2,2- trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, ca-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthtyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, o-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, an oxygen protecting group is silyl, TBDPS, TBDMS, TIPS, TES, TMS, MOM, THP, t-Bu, Bn, allyl, acetyl, pivaloyl, or benzoyl.

In certain embodiments, the sulfur atom substituents are independently substituted (e.g., substituted with one or more halogen) or unsubstituted $C_{1-6}$ alkyl, —C(=O)$R^{aa}$, —CO$_2R^{aa}$, —C(=O)N($R^{bb}$)$_2$, or a sulfur protecting group. In certain embodiments, the sulfur atom substituents are independently substituted (e.g., substituted with one or more halogen) or unsubstituted $C_{1-6}$ alkyl, —C(=O)$R^{aa}$, —CO$_2R^{aa}$, —C(=O)N($R^{bb}$)$_2$, or a sulfur protecting group, wherein $R^{aa}$ is hydrogen, substituted (e.g., substituted with one or more halogen) or unsubstituted $C_{1-6}$ alkyl, or an oxygen protecting group when attached to an oxygen atom; and each $R^{bb}$ is independently hydrogen, substituted (e.g., substituted with one or more halogen) or unsubstituted $C_{1-6}$ alkyl, or a nitrogen protecting group. In certain embodiments, the sulfur atom substituents are independently substituted (e.g., substituted with one or more halogen) or unsubstituted $C_{1-6}$ alkyl or a sulfur protecting group.

In certain embodiments, the substituent present on a sulfur atom is a sulfur protecting group (also referred to as a "thiol protecting group"). Sulfur protecting groups include —$R^{aa}$, —N($R^{bb}$)$_2$, —C(=O)S$R^{aa}$, —C(=O)$R^{aa}$, —CO$_2R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —S(=O)$R^{aa}$, —SO$_2R^{aa}$, —Si($R^{aa}$)$_3$, —P($R^{cc}$)$_2$, —P($R^{cc}$)$_3$, —P(=O)$_2R^{aa}$, —P(=O)($R^{aa}$)$_2$, —P(=O)(O$R^{cc}$)$_2$, —P(=O)$_2$N($R^{bb}$)$_2$, and —P(=O)(N$R^{bb}$)$_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

In certain embodiments, the molecular weight of a substituent is lower than 250, lower than 200, lower than 150, lower than 100, or lower than 50 g/mol. In certain embodiments, a substituent consists of carbon, hydrogen, fluorine, chlorine, bromine, iodine, oxygen, sulfur, nitrogen, and/or silicon atoms. In certain embodiments, a substituent consists of carbon, hydrogen, fluorine, chlorine, bromine, iodine, oxygen, sulfur, and/or nitrogen atoms. In certain embodiments, a substituent consists of carbon, hydrogen, fluorine, chlorine, bromine, and/or iodine atoms. In certain embodiments, a substituent consists of carbon, hydrogen, fluorine, and/or chlorine atoms. In certain embodiments, a substituent comprises 0, 1, 2, or 3 hydrogen bond donors. In certain embodiments, a substituent comprises 0, 1, 2, or 3 hydrogen bond acceptors.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3^-$, ClO$_4^-$, OH$^-$, H$_2$PO$_4^-$, HCO$_3^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4^-$, PF$_4^-$, PF$_6^-$, AsF$_6^-$, SbF$_6^-$, B[3,5-(CF$_3$)$_2$C$_6$H$_3$]$_4^-$, B(C$_6$F$_5$)$_4^-$, BPh$_4^-$, Al(OC(CF$_3$)$_3$)$_4^-$, and carborane anions (e.g., CB$_{11}$H$_{12}^-$ or (HCB$_{11}$Me$_5$Br$_6$)$^-$). Exemplary counterions which may be multivalent include CO$_3^{2-}$, HPO$_4^{2-}$, PO$_4^{3-}$, B$_4$O$_7^{2-}$, SO$_4^{2-}$, S$_2$O$_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J.*

*Pharmaceutical Sciences,* 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4} alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R \cdot x H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates ($R \cdot 0.5 H_2O$)), and polyhydrates (x is a number greater than 1, e.g., dihydrates ($R \cdot 2 H_2O$) and hexahydrates ($R \cdot 6 H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorph" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than 1,500 g/mol. In certain embodiments, the molecular weight of a small molecule is not more than 1,000 g/mol, not more than 900 g/mol, not more than 800 g/mol, not more than 700 g/mol, not more than 600 g/mol, not more than 500 g/mol, not more than 400 g/mol, not more than 300 g/mol, not more than 200 g/mol, or not more than 100 g/mol. In certain embodiments, the molecular weight of a small molecule is at least 100 g/mol, at least 200 g/mol, at least 300 g/mol, at least 400 g/mol, at least 500 g/mol, at least 600 g/mol, at least 700 g/mol, at least 800 g/mol, or at least 900 g/mol, or at least 1,000 g/mol. Combinations of the above ranges (e.g., at least 200 g/mol and not more than 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

A "protein," "peptide," or "polypeptide" comprises a polymer of amino acid residues linked together by peptide bonds. The term refers to proteins, polypeptides, and peptides of any size, structure, or function. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. One or more of the amino acids in a protein may be protected. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these. In certain embodiments, a protein comprises between 2 and 10, between 10 and 30, between 30 and 100, between 100 and 300, or between 300 and 1,000, inclusive, amino acids. In certain embodiments, the amino acids in a protein are natural amino acids. In certain embodiments, the amino acids in a protein are unnatural amino acids. In certain embodiments, the amino acids in a protein are a combination of natural amino acids and unnatural amino acids.

The terms "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a viral infection or cancer. In some embodiments, treatment may be administered after one or more signs or symptoms of the viral infection or cancer have developed or have been observed. In other embodiments, treatment may be administered in the absence of signs or symptoms of the viral infection or cancer. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenstrom's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyo sarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

FIG. 1A shows fold increase in HLA-DR protein in human cell lines treated with I-1. FIG. 1B shows fold increase in MHC Class II IA/IE protein in mouse cell lines treated with I-1 or DMSO.

FIG. 2A shows the percentage of MHC Class II positive cells at various concentrations of I-1. FIG. 2B shows MHC Class II geometric MFI (mean fluorescence intensity) at various concentrations of I-1.

FIG. 3A shows the percentage of MHC Class II positive cells in the presence of DMSO or various concentrations of I-1. FIG. 3B shows the geometric mean MFI (mean fluorescence intensity) for MHC Class II in the presence of DMSO or various concentrations of I-1.

FIG. 4A shows the percent of viable P388D1 cells in the presence of DMSO or various concentrations of I-1. FIG. 4B shows the percent of viable RENCA cells in the presence of DMSO or various concentrations of I-1.

FIG. 5A shows the effect of a vehicle (Veh), I-1, anti-PD-1 antibody (Anti-PD-1, αPD-1, or αPD1), and I-1+anti-PD-1 antibody on tumor volume (mm$^3$) over several days, with treatment initiated at twenty four hours after tumor induction. FIG. 5B shows the percent of cells positive for MHC Class II expression (on day 11, d11) treated with vehicle, I-1, anti-PD-1 antibody, or I-1+anti-PD-1 antibody, and also shows the percent of [CD45+] CD3+ cells in tumors (on day 11, d11) treated with vehicle, I-1, anti-PD-1 antibody, or I-1+anti-PD-1 antibody.

FIGS. 7A to 7D show in vivo individual responses through day 21 in mice with RENCA tumors. FIG. 7A shows the tumor volume (mm$^3$) over time (days) in response to vehicle. FIG. 7B shows the tumor volume (mm$^3$) over time (days) in response to I-1 delivered at 50 mg/kg twice daily at 12 hour intervals (50 mpk BID). FIG. 7C shows the tumor volume (mm$^3$) over time (days) in response to Anti-PD-1 antibody delivered at 10 mg/kg twice weekly (10 mpk BIW). FIG. 7D shows the tumor volume (mm$^3$) over time (days) in response to the combination of I-1+Anti-PD-1 antibody.

FIG. 8A shows the percent of cells positive for MHC II (IA/IE) in tumors from mice treated with a vehicle or I-1. FIG. 8B shows the percent of cells positive for [CD45+] CD3 in tumors from mice treated with a vehicle or I-1.

DETAILED DESCRIPTION

Figure 1A:
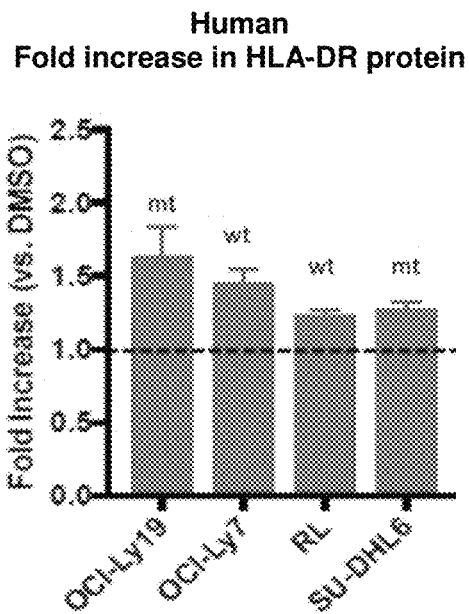
FIGS. 1A and 1B show MHC Class II expression in human and mouse cell lines.

The present disclosure relates to compositions, kits, and methods for, e.g., treatment of cancer.

Selective HDAC3 Inhibitors

The compositions, kits, and methods described herein involve selective HDAC3 inhibitors.

Compounds of Formula (I)

In certain embodiments, the selective HDAC3 inhibitor is a compound of Formula (I):

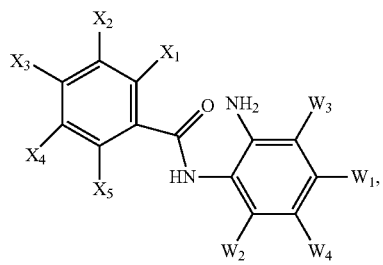

(I)

or a pharmaceutically acceptable salt, hydrate, solvate, or prodrug thereof, wherein:

$W_1$, $W_2$, $W_3$, and $W_4$ are each independently selected from hydrogen, fluorine, chlorine, bromine, $CF_3$, $CH_3$, and deuterium, provided that at least one of $W_1$, $W_2$, $W_3$, or $W_4$ is not hydrogen;

$X_1$ and $X_5$ are each independently selected from hydrogen, halogen and $C_1$-$C_3$ alkyl;

$X_2$, $X_3$, and $X_4$ are each independently selected from hydrogen, halogen, $OR^5$, $C(O)R^6$, $OS(O)_pR^7$, $NR^3R^4$, $NR^1C(O)R^2$, $NR^1S(O)_pR^7$, $S(O)_qR^{10}$, $C(O)OR^{11}$, $C(O)NR^{12}R^{13}$, $OC(O)OR^{14}$, $OC(O)NR^{15}R^{16}$, $NR^{17}C(O)OR^{18}$, $NR^{19}C(O)NR^{20}R^{21}$, $C_1$-$C_8$ alkyl, $C_2$-$C_8$ alkenyl, $C_2$-$C_8$ alkynyl, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring, wherein said alkyl, alkenyl, alkynyl, cycloalkyl, cycloalkenyl, aromatic ring, heteroaromatic ring, and heterocyclic ring is unsubstituted or substituted with one or more $R^a$ and one or two of $X_2$, $X_3$, and $X_4$ is hydrogen;

$R^a$ is selected from halogen, $OR^{25}$, $C_1$-$C_8$ alkyl, $CF_3$, $CHF_2$, $CH_2F$, $NR^{26}C(O)R^{27}$, and $NR^{28}R^{29}$; or $X_2$ and $X_3$ or $X_4$ and $X_3$ taken together with the atoms to which they are attached form ring selected from a $C_3$-$C_8$ cycloalkyl, $C_4$-$C_8$ cycloalkenyl, aromatic ring, 3-8 membered heteroaromatic ring and 3-8 membered saturated or partially saturated heterocyclic ring, wherein said ring is unsubstituted or substituted with one or more $R^v$, $R^v$ is selected from halogen, $OR^{25}$, $C_1$-$C_8$ alkyl, $CF_3$, $CHF_2$, $CH_2F$, $NR^{26}C(O)R^{27}$, $NR^{28}R^{29}$, $S(O)_qR^7$, $S(O)_qR^{10}$, $C(O)OR^{11}$, $C(O)NR^{12}R^{13}$, $OC(O)OR^{14}$, $OC(O)NR^{15}R^{16}$, $NR^{17}C(O)OR^8$, and $NR^9C(O)NR^{20}R^{21}$;

$R^1$ and $R^{26}$ are each independently selected from hydrogen and $C_1$-$C_8$ alkyl;

$R^2$ is selected from hydrogen, $C_1$-$C_8$ alkyl, $C_2$-$C_8$ alkenyl, $C_3$-$C_8$ alkynyl, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring, wherein said alkyl, alkenyl, alkynyl, cycloalkyl, cycloalkenyl, aromatic ring, heteroaromatic ring, and heterocyclic ring are unsubstituted or substituted with one or more $R^b$;

$R^{27}$ is selected from hydrogen, $C_1$-$C_8$ alkyl, $C_3$-$C_8$ alkynyl, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring, wherein said alkyl, alkenyl, alkynyl, cycloalkyl, cycloalkenyl, aromatic ring, heteroaromatic ring, and heterocyclic ring are unsubstituted or substituted with one or more $R^b$;

$R^b$ is selected from halogen, $C_1$-$C_8$ alkyl, $CF_3$, $CHF_2$, $CH_2F$, $OR^{25}$, $NH_2$, $NHCH_3$, $N(CH_3)_2$, $C_3$-$C_8$ cycloalkyl, $C_4$-$C_8$ cycloalkenyl, aromatic ring, 3-8 membered heteroaromatic ring, 3-8 membered saturated or partially saturated heterocyclic ring, wherein said cycloalkyl, cycloalkenyl, aromatic ring, heteroaromatic ring, and heterocyclic ring is unsubstituted or substituted with one or more $R^{b1}$;

$R^{b1}$ is selected from halogen, $C_1$-$C_3$ alkyl, $CF_3$, $CHF_2$, $CH_2F$, $OH$, $OCH_3$, $SOCH_3$, $S(O)_2CH_3$, $NH_2$, $NHCH_3$, and $N(CH_3)_2$;

$R^3$ and $R^4$ are each independently selected from hydrogen, $C_1$-$C_8$ alkyl, $C_2$-$C_8$ alkenyl, $C_3$-$C_8$ alkynyl, $C_3$-$C_8$ cycloalkyl, $C_4$-$C_8$ cycloakenyl, aromatic ring, 3-8 membered heteroaromatic ring, and 3-8 membered saturated or partially saturated heterocyclic ring, wherein said alkyl, alkenyl, alkynyl, cycloalkyl, cycloalkenyl, aromatic ring, heteroaromatic ring and heterocyclic ring are unsubstituted or substituted with one or more $R^g$;

$R^{28}$ and $R^{29}$ are each independently selected from hydrogen, $C_1$-$C_8$ alkyl, $C_2$-$C_8$ alkenyl, $C_3$-$C_8$ alkynyl, $C_3$-$C_8$ cycloalkyl, $C_4$-$C_8$ cycloakenyl, and 3-8 membered saturated or partially saturated heterocyclic ring, wherein said alkyl, alkenyl, alkynyl, cycloalkyl, cycloalkenyl, aromatic ring, heteroaromatic ring and heterocyclic ring are unsubstituted or substituted with one or more $R^g$;

$R^g$ is selected from halogen, $C_1$-$C_3$ alkyl, $CF_3$, $CHF_2$, $CH_2F$, $OH$, $OCH_3$, $NH_2$, $NHCH_3$, $N(CH_3)_2$, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring, wherein said cycloalkyl, cycloalkenyl, aromatic ring, heteroaromatic ring, and heterocyclic ring is unsubstituted or substituted with one or more $R^h$;

$R^h$ is selected from halogen, $C_1$-$C_3$ alkyl, $CF_3$, $CHF_2$, $CH_2F$, $OH$, $OCH_3$, $SOCH_3$, $S(O)_2CH_3$, $NH_2$, $NHCH_3$, and $N(CH_3)_2$;

$R^5$ and $R^{25}$ are each independently selected from hydrogen, $C_1$-$C_8$ alkyl, $CF_3$, $CHF_2$, $CH_2F$, $C_2$-$C_8$ alkenyl, $C_3$-$C_8$ alkynyl, $C_3$-$C_8$ cycloalkyl, $C_4$-$C_8$ cycloalkenyl, aromatic ring, 3-8 membered heteroaromatic ring, 3-8 membered saturated or partially saturated heterocyclic ring, wherein said alkyl, alkenyl, alkynyl, cycloalkyl, cycloalkenyl, aromatic ring, heteroaromatic ring and heterocyclic ring are unsubstituted or substituted with one or more $R^c$;

$R^c$ is selected from halogen, $C_1$-$C_3$ alkyl, $CF_3$, $CHF_2$, $CH_2F$, $OH$, $OCH_3$, $NH_2$, $NHCH_3$, $N(CH_3)_2$, $C_3$-$C_8$ cycloalkyl, $C_4$-$C_8$ cycloalkenyl, aromatic ring, 3-8 membered heteroaromatic ring, 3-8 membered saturated or partially saturated heterocyclic ring, wherein said cycloalkyl, cycloalkenyl, aromatic ring, heteroaromatic ring, and heterocyclic ring is unsubstituted or substituted with one or more $R^d$;

$R^d$ is selected from halogen, $C_1$-$C_3$ alkyl, $CF_3$, $CHF_2$, $CH_2F$, $OH$, $OCH_3$, $SOCH_3$, $S(O)_2CH_3$, $NH_2$, $NHCH_3$, and $N(CH_3)_2$;

$R^6$ is selected from hydrogen, $OR^{25}$, $C_1$-$C_8$ alkyl, $CF_3$, $CHF_2$, $CH_2F$, $C_2$-$C_8$ alkenyl, $C_3$-$C_8$ alkynyl, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring; wherein said alkyl, alkenyl, alkynyl, cycloalkyl, cycloalkenyl, aromatic ring, heteroaromatic ring and heterocyclic ring are unsubstituted or substituted with one or more $R^e$;

$R^e$ is selected from halogen, $C_1$-$C_3$ alkyl, $CF_3$, $CHF_2$, $CH_2F$, OH, $OCH_3$, $NH_2$, $NHCH_3$, $N(CH_3)_2$, $C_3$-$C_8$ cycloalkyl, $C_4$-$C_8$ cycloalkenyl, aromatic ring, 3-8 membered heteroaromatic ring, 3-8 membered saturated or partially saturated heterocyclic ring, wherein said cycloalkyl, cycloalkenyl, aromatic ring, heteroaromatic ring, and heterocyclic ring is unsubstituted or substituted with one or more $R^f$;

$R^f$ is selected from halogen, $C_1$-$C_3$ alkyl, $CF_3$, $CHF_2$, $CH_2F$, OH, $OCH_3$, $SOCH_3$, $S(O)_2CH_3$, $NH_2$, $NHCH_3$, and $N(CH_3)_2$;

$R^7$ is selected from $C_1$-$C_8$ alkyl, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring; wherein said alkyl, cycloalkyl, cycloalkenyl, aromatic ring, heteroaromatic ring, and heterocyclic ring are unsubstituted or substituted with one or more $R^i$;

$R^i$ is selected from halogen, $C_1$-$C_3$ alkyl, $CF_3$, $CHF_2$, $CH_2F$, OH, $OCH_3$, $NH_2$, $NHCH_3$, and $N(CH_3)_2$;

$R^{10}$ are each independently selected from $C_1$-$C_8$ alkyl, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring; wherein said alkyl, cycloalkyl, cycloalkenyl, aromatic ring, heteroaromatic ring, and heterocyclic ring are unsubstituted or substituted with one or more $R^{4j}$;

$R^j$ is selected from halogen, $C_1$-$C_3$ alkyl, $CF_3$, $CHF_2$, $CH_2F$, OH, $OCH_3$, $NH_2$, $NHCH_3$, and $N(CH_3)_2$;

$R^{11}$ is selected from hydrogen, $C_1$-$C_8$ alkyl, $C_2$-$C_8$ alkenyl, $C_2$-$C_8$ alkynyl, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring; wherein said alkyl, alkenyl, alkynyl, cycloalkyl, cycloalkenyl, aromatic ring, heteroaromatic ring and heterocyclic ring are unsubstituted or substituted with one or more $R^k$;

$R^k$ is selected from halogen, $C_1$-$C_3$ alkyl, $CF_3$, $CHF_2$, $CH_2F$, OH, $OCH_3$, $NH_2$, $NHCH_3$, $N(CH_3)_2$, $C_3$-$C_8$ cycloalkyl, $C_4$-$C_8$ cycloalkenyl, aromatic ring, 3-8 membered heteroaromatic ring, 3-8 membered saturated or partially saturated heterocyclic ring, wherein said cycloalkyl, cycloalkenyl, aromatic ring, heteroaromatic ring, and heterocyclic ring is unsubstituted or substituted with one or more $R^{k1}$;

$R^{k1}$ is selected from halogen, $C_1$-$C_3$ alkyl, $CF_3$, $CHF_2$, $CH_2F$, OH, $OCH_3$, $SO_2CH_3$, $NH_2$, $NHCH_3$, and $N(CH_3)_2$;

$R^{12}$ and $R^{13}$ are each independently selected from hydrogen, $C_1$-$C_8$ alkyl, $C_2$-$C_8$ alkenyl, $C_3$-$C_8$ alkynyl, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring, wherein said alkyl, alkenyl, alkynyl, cycloalkyl, cycloalkenyl, aromatic ring, heteroaromatic ring and heterocyclic ring are unsubstituted or substituted with one or more $R^l$;

$R^l$ is selected from halogen, $C_1$-$C_3$ alkyl, $CF_3$, $CHF_2$, $CH_2F$, OH, $OCH_3$, $NH_2$, $NHCH_3$, $N(CH_3)_2$, $C_3$-$C_8$ cycloalkyl, $C_4$-$C_8$ cycloalkenyl, aromatic ring, 3-8 membered heteroaromatic ring, 3-8 membered saturated or partially saturated heterocyclic ring, wherein said cycloalkyl, cycloalkenyl, aromatic ring, heteroaromatic ring, and heterocyclic ring is unsubstituted or substituted with one or more $R^m$;

$R^m$ is selected from halogen, $C_1$-$C_3$ alkyl, $CF_3$, $CHF_2$, $CH_2F$, OH, $OCH_3$, $SOCH_3$, $S(O)_2CH_3$, $NH_2$, $NHCH_3$, and $N(CH_3)_2$;

$R^{14}$ is selected from $C_1$-$C_8$ alkyl, $C_2$-$C_8$ alkenyl, $C_2$-$C_8$ alkynyl, $C_3$-$C_8$ cycloalkyl, $C_4$-$C_8$ cycloalkenyl, and aromatic ring; wherein said alkyl, alkenyl, alkynyl, cycloalkyl, cycloalkenyl, and aromatic ring are unsubstituted or substituted with one or more $R^n$;

$R^n$ is selected from halogen, $C_1$-$C_3$ alkyl, $CF_3$, $CHF_2$, $CH_2F$, OH, $OCH_3$, $NH_2$, $NHCH_3$, $N(CH_3)_2$, $C_3$-$C_8$ cycloalkyl, $C_4$-$C_8$ cycloalkenyl, aromatic ring, 3-8 membered heteroaromatic ring, 3-8 membered saturated or partially saturated heterocyclic ring, wherein said cycloalkyl, cycloalkenyl, aromatic ring, heteroaromatic ring, and heterocyclic ring is unsubstituted or substituted with one or more $R^{n1}$;

$R^{n1}$ is selected from halogen, $C_1$-$C_3$ alkyl, $CF_3$, $CHF_2$, $CH_2F$, OH, $OCH_3$, $SO_2CH_3$, $NH_2$, $NHCH_3$, and $N(CH_3)_2$;

$R^{15}$ and $R^{16}$ are each independently selected from hydrogen, $C_1$-$C_8$ alkyl, $C_2$-$C_8$ alkenyl, $C_3$-$C_8$ alkynyl, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring, wherein said alkyl, alkenyl, alkynyl, cycloalkyl, cycloalkenyl, aromatic ring, heteroaromatic ring and heterocyclic ring are unsubstituted or substituted with one or more $R^o$;

$R^o$ is selected from halogen, $C_1$-$C_3$ alkyl, $CF_3$, $CHF_2$, $CH_2F$, OH, $OCH_3$, $NH_2$, $NHCH_3$, $N(CH_3)_2$, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring, wherein said cycloalkyl, cycloalkenyl, aromatic ring, heteroaromatic ring, and heterocyclic ring is unsubstituted or substituted with one or more $R^p$;

$R^p$ is selected from halogen, $C_1$-$C_3$ alkyl, $CF_3$, $CHF_2$, $CH_2F$, OH, $OCH_3$, $SOCH_3$, $S(O)_2CH_3$, $NH_2$, $NHCH_3$, and $N(CH_3)_2$;

$R^{17}$ and $R^{19}$ are each independently selected from hydrogen and $C_1$-$C_8$ alkyl;

$R^{18}$ is selected from $C_1$-$C_8$ alkyl, $C_2$-$C_8$ alkenyl, $C_2$-$C_8$ alkynyl, $C_3$-$C_8$ cycloalkyl, $C_4$-$C_8$ cycloalkenyl, aromatic ring, 3-8 membered heteroaromatic ring, and 3-8 membered saturated heterocyclic ring; wherein said alkyl, alkenyl, alkynyl, cycloalkyl, cycloalkenyl, heteroaromatic ring, heterocyclic ring, and aromatic ring are unsubstituted or substituted with one or more $R^q$;

$R^q$ is selected from halogen, $C_1$-$C_3$ alkyl, $CF_3$, $CHF_2$, $CH_2F$, OH, $OCH_3$, $NH_2$, $NHCH_3$, $N(CH_3)_2$, $C_3$-$C_8$ cycloalkyl, $C_4$-$C_8$ cycloalkenyl, aromatic ring, 3-8 membered heteroaromatic ring, 3-8 membered saturated or partially saturated heterocyclic ring, wherein said cycloalkyl, cycloalkenyl, aromatic ring, heteroaromatic ring, and heterocyclic ring is unsubstituted or substituted with one or more $R^{q1}$;

$R^{q1}$ is selected from halogen, $C_1$-$C_3$ alkyl, $CF_3$, $CHF_2$, $CH_2F$, OH, $OCH_3$, $SO_2CH_3$, $NH_2$, $NHCH_3$, and $N(CH_3)_2$;

$R^{20}$ and $R^{21}$ are each independently selected from selected from hydrogen, $C_1$-$C_8$ alkyl, $C_2$-$C_8$ alkenyl, $C_3$-$C_8$ alkynyl, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring, wherein said alkyl, alkenyl, alkynyl, cycloalkyl, cycloalkenyl, aromatic ring, heteroaromatic ring and heterocyclic ring are unsubstituted or substituted with one or more $R^r$;

$R^r$ is selected from halogen, $C_1$-$C_3$ alkyl, $CF_3$, $CHCF_2$, $CH_2F$, OH, $OCH_3$, $NH_2$, $NHCH_3$, $N(CH_3)_2$, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring, wherein said cycloalkyl, cycloalkenyl, aromatic ring, heteroaromatic ring, and heterocyclic ring is unsubstituted or substituted with one or more $R^s$;

$R^s$ is selected from halogen, $C_1$-$C_3$ alkyl, $CF_3$, $CHF_2$, $CH_2F$, OH, $OCH_3$, $SOCH_3$, $SO_2CH_3$, $NH_2$, $NHCH_3$, and $N(CH_3)_2$; and p and q are each independently selected from 0, 1, and 2.

In certain embodiments:

$W_1$, $W_2$, $W_3$, and $W_4$ are each independently selected from hydrogen and fluorine, provided that at least $W_1$ is not hydrogen;

$X_3$ is selected from halogen, $OR^5$, $C(O)R^6$, $OS(O)_pR^7$, $NR^3R^4$, $NR^1C(O)R^2$, $S(O)_qR^{10}$, $C(O)OR^{11}$, $C(O)NR^{12}R^{13}$, $OC(O)OR^{14}$, $OC(O)NR^{15}R^{16}$, $NR^{17}C(O)OR^{18}$, $NR^{19}C(O)NR^{20}R^{21}$, $C_1$-$C_8$ alkyl, $C_2$-$C_8$ alkenyl, $C_2$-$C_8$ alkynyl, $C_3$-$C_8$ cycloalkyl, $C_4$-$C_8$ cycloalkenyl, aromatic ring, 3-8 membered heteroaromatic ring, and 3-8 membered, saturated or partially saturated, heterocyclic ring, wherein said alkyl, alkenyl, alkynyl, cycloalkyl, cycloalkenyl, aromatic ring, heteroaromatic ring, and heterocyclic ring are unsubstituted or substituted with one or more $R^a$;

$X_2$ and $X_4$ are each independently hydrogen or halogen, provided that one or two of $X_2$ and $X_4$ is hydrogen;

$R^b$ is selected from halogen, $C_1$-$C_8$ alkyl, $CF_3$, $CHF_2$, $CH_2F$, $OR^{25}$, $NH_2$, $NHCH_3$, $N(CH_3)_2$, $C_3$-$C_8$ cycloalkyl, $C_4$-$C_8$ cycloalkenyl, aromatic ring, and 3-8 membered, saturated or partially saturated, heterocyclic ring, wherein said cycloalkyl, cycloalkenyl, aromatic ring, and heterocyclic ring are unsubstituted or substituted with one or more $R^{b1}$;

$R^{28}$ is selected from $C_1$-$C_8$ alkyl, $C_2$-$C_8$ alkenyl, $C_3$-$C_8$ alkynyl, $C_3$-$C_8$ cycloalkyl, $C_4$-$C_8$ cycloakenyl, aromatic ring, 3-8 membered heteroaromatic ring, and 3-8 membered, saturated or partially saturated, heterocyclic ring, wherein said alkyl, alkenyl, alkynyl, cycloalkyl, cycloalkenyl, aromatic ring, heteroaromatic ring, and heterocyclic ring are unsubstituted or substituted with one or more $R^g$;

$R^{29}$ is selected from hydrogen, $C_1$-$C_8$ alkyl, $C_2$-$C_8$ alkenyl, $C_3$-$C_8$ alkynyl, $C_3$-$C_8$ cycloalkyl, $C_4$-$C_8$ cycloakenyl, aromatic ring, 3-8 membered heteroaromatic ring, and 3-8 membered, saturated or partially saturated, heterocyclic ring, wherein said alkyl, alkenyl, alkynyl, cycloalkyl, cycloalkenyl, aromatic ring, heteroaromatic ring, and heterocyclic ring are unsubstituted or substituted with one or more $R^g$; and $R^g$ is selected from $CHF_2$, $CH_2F$, $NH_2$, $NHCH_3$, $N(CH_3)_2$, $C_3$-$C_8$ cycloalkyl, $C_4$-$C_8$ cycloalkenyl, and 3-8 membered, saturated or partially saturated, heterocyclic ring, wherein said cycloalkyl, cycloalkenyl, and heterocyclic ring are unsubstituted or substituted with one or more $R^h$.

In certain embodiments, $W_1$ is F. In certain embodiments, each of $W_2$, $W_3$, and $W_4$ is independently H or F. In certain embodiments, each of $W_2$, $W_3$, and $W_4$ is H.

In certain embodiments, $X_1$ is H, halogen, and $C_1$-$C_8$ alkyl, wherein said alkyl is unsubstituted or substituted with one or more $R^a$. In certain embodiments, $X_1$ is H or halogen. In certain embodiments, $X_1$ is H. In certain embodiments, $X_1$ is halogen (e.g., F).

In certain embodiments, $X_2$ is H, halogen, and $C_1$-$C_8$ alkyl, wherein said alkyl is unsubstituted or substituted with one or more $R^a$. In certain embodiments, $X_2$ is H or halogen. In certain embodiments, $X_2$ is H. In certain embodiments, $X_2$ is halogen (e.g., F).

In certain embodiments, $X_4$ is H, halogen, and $C_1$-$C_8$ alkyl, wherein said alkyl is unsubstituted or substituted with one or more $R^a$. In certain embodiments, $X_4$ is H or halogen. In certain embodiments, $X_4$ is H. In certain embodiments, $X_4$ is halogen (e.g., F).

In certain embodiments, $X_5$ is H, halogen, and $C_1$-$C_8$ alkyl, wherein said alkyl is unsubstituted or substituted with one or more $R^a$. In certain embodiments, $X_5$ is H or halogen. In certain embodiments, $X_5$ is H. In certain embodiments, $X_5$ is halogen (e.g., F).

In certain embodiments, $X_3$ is not H. In certain embodiments, $X_3$ is halogen. In certain embodiments, $X_3$ is $OR^5$, $C(O)R^6$, $OS(O)_pR^7$, $NR^3R^4$, $NR^1C(O)R^2$, $NR^1S(O)_pR^7$, $S(O)_qR^{10}$, $C(O)OR^{11}$, $C(O)NR^{12}R^{13}$, $OC(O)OR^{14}$, $OC(O)NR^{15}R^{16}$, $NR^{17}C(O)OR^{18}$, or $NR^{19}C(O)NR^{20}R^{21}$. In certain embodiments, $X_3$ is $NR^1C(O)R^2$, $NR^1S(O)_pR^7$, $OC(O)OR^{14}$, $OC(O)NR^{15}R^{16}$, $NR^{17}C(O)OR^{18}$, or $NR^{19}C(O)NR^{20}R^{21}$. In certain embodiments, $X_3$ is $NR^1C(O)R^2$. In certain embodiments, $X_3$ is $NHC(O)R^2$. In certain embodiments, $X_3$ is $NHC(O)CH_3$. In certain embodiments, $X_3$ is $C_1$-$C_8$ alkyl, $C_2$-$C_8$ alkenyl, $C_2$-$C_8$ alkynyl, $C_3$-$C_8$ cycloalkyl, or $C_4$-$C_8$ cycloalkenyl, wherein said alkyl, alkenyl, alkynyl, cycloalkyl, and cycloalkenyl are unsubstituted or substituted with one or more $R^a$. In certain embodiments, $X_3$ is aromatic ring or 3-8 membered heteroaromatic ring, wherein said aromatic ring and heteroaromatic ring are unsubstituted or substituted with one or more $R^a$. In certain embodiments, $X_3$ is 3-8 membered saturated or partially saturated heterocyclic ring, wherein said heterocyclic ring is unsubstituted or substituted with one or more $R^a$.

In certain embodiments, $W_1$, $W_2$, $W_3$, and $W_4$ are each independently selected from hydrogen and fluorine, provided that at least one of $W_1$, $W_2$, $W_3$, and $W_4$ is not hydrogen;

$X_1$ and $X_5$ are each independently selected from hydrogen, halogen and $C_1$-$C_3$ alkyl;

$X_3$ is selected from halogen and $NR^1C(O)R^2$;

$X_2$ and $X_4$ are each independently hydrogen or halogen, provided that one or two of $X_2$ and $X_4$ is hydrogen;

$R^1$ is selected from hydrogen and $C_1$-$C_8$ alkyl;

$R^2$ is selected from hydrogen, $C_1$-$C_8$ alkyl, $C_2$-$C_8$ alkenyl, $C_3$-$C_8$ alkynyl, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring, wherein said alkyl, alkenyl, alkynyl, cycloalkyl, cycloalkenyl, aromatic ring, heteroaromatic ring, and heterocyclic ring are unsubstituted or substituted with one or more $R^b$;

$R^b$ is selected from halogen, $C_1$-$C_8$ alkyl, $CF_3$, $CHF_2$, $CH_2F$, $OR^{25}$, $NH_2$, $NHCH_3$, $N(CH_3)_2$, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring, wherein said cycloalkyl, cycloalkenyl, aromatic ring, heteroaromatic ring, and heterocyclic ring are unsubstituted or substituted with one or more $R^{b1}$; and $R^{b1}$ is selected from halogen, $C_1$-$C_3$ alkyl, $CF_3$, $CHF_2$, $CH_2F$, OH, $OCH_3$, $SOCH_3$, $S(O)_2CH_3$, $NH_2$, $NHCH_3$, and $N(CH_3)_2$;

provided that said compound is not of the formula:

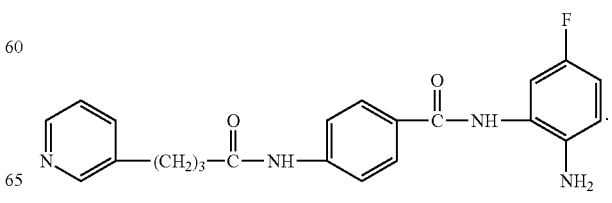

In certain embodiments, the selective HDAC3 inhibitor is a compound of the formula:

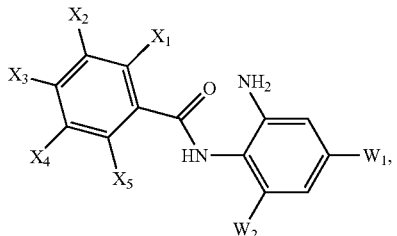

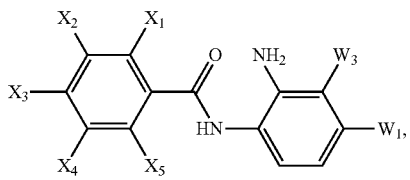

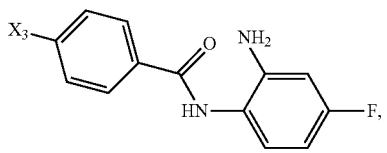

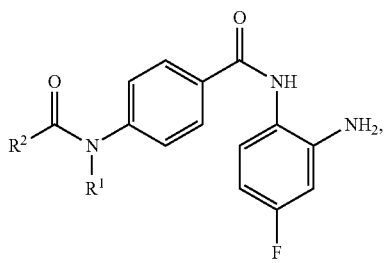

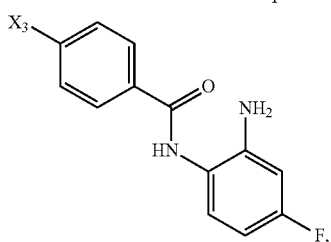

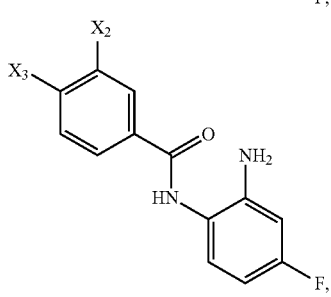

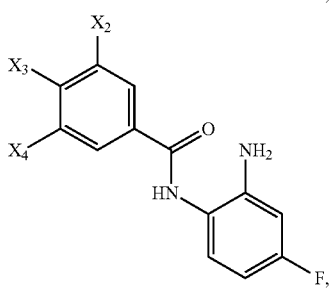

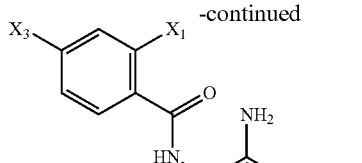

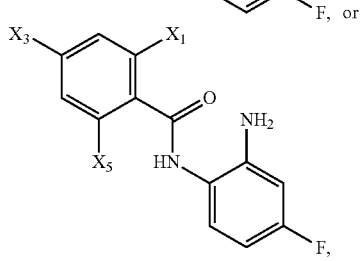

or a pharmaceutically acceptable salt, hydrate, solvate, or prodrug thereof.

In certain embodiments, the selective HDAC3 inhibitor is a compound of the formula

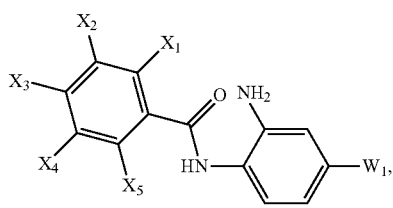

or a pharmaceutically acceptable salt, hydrate, solvate, or prodrug thereof.

In certain embodiments, the selective HDAC3 inhibitor is a compound of the formula

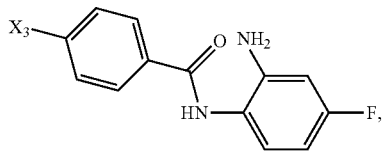

or a pharmaceutically acceptable salt, hydrate, solvate, or prodrug thereof.

In certain embodiments, the selective HDAC3 inhibitor is a compound of the formula

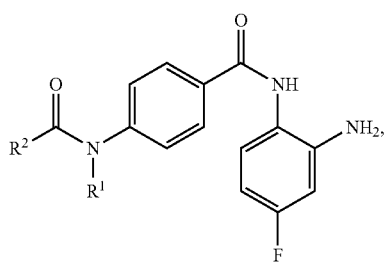

or a pharmaceutically acceptable salt, hydrate, solvate, or prodrug thereof.

In certain embodiments, the selective HDAC3 inhibitor is a compound of the formula

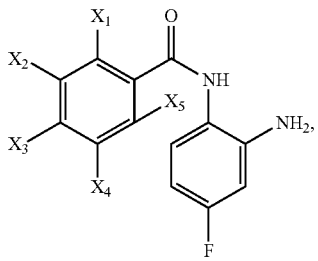

or a pharmaceutically acceptable salt, hydrate, solvate, or prodrug thereof, wherein:

$X_3$ is halogen, $OR^5$, $C(O)R^6$, $OS(O)_pR^7$, $NR^3R^4$, $NR^1C(O)R^2$, $NR^1S(O)_pR^7$, $S(O)_qR^{10}$, $C(O)OR^{11}$, $C(O)NR^{12}R^{13}$, $OC(O)OR^{14}$, $OC(O)NR^{15}R^{16}$, $NR^{17}C(O)OR^{18}$, $NR^{19}C(O)NR^{20}R^{21}$, $C_1$-$C_8$ alkyl, $C_2$-$C_8$ alkenyl, $C_2$-$C_8$ alkynyl, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring, wherein said alkyl, alkenyl, alkynyl, cycloalkyl, cycloalkenyl, aromatic ring, heteroaromatic ring, and heterocyclic ring is unsubstituted or substituted with one or more $R^a$;

one of $X_2$ and $X_4$ is hydrogen; and the other one of $X_2$ and $X_4$ is hydrogen, halogen, $OR^5$, $C(O)R^6$, $OS(O)_pR^7$, $NR^3R^4$, $NR^1C(O)R^2$, $NR^1S(O)_pR^7$, $S(O)_qR^{10}$, $C(O)OR^{11}$, $C(O)NR^{12}R^{13}$, $OC(O)OR^{14}$, $OC(O)NR^{15}R^{16}$, $NR^{17}C(O)OR^{18}$, $NR^{19}C(O)NR^{20}R^{21}$, $C_1$-$C_8$ alkyl, $C_2$-$C_8$ alkenyl, $C_2$-$C_8$ alkynyl, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring, wherein said alkyl, alkenyl, alkynyl, cycloalkyl, cycloalkenyl, aromatic ring, heteroaromatic ring, and heterocyclic ring is unsubstituted or substituted with one or more $R^a$.

In certain embodiments, the selective HDAC3 inhibitor is a compound of the formula

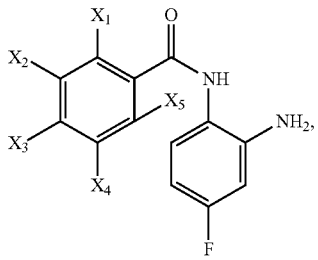

or a pharmaceutically acceptable salt, hydrate, solvate, or prodrug thereof, wherein:

$X_3$ is halogen, $OR^5$, $C(O)R^6$, $OS(O)_pR^7$, $NR^3R^4$, $NR^1C(O)R^2$, $NR^1S(O)_pR^7$, $S(O)_qR^{10}$, $C(O)OR^{11}$, $C(O)NR^{12}R^{13}$, $OC(O)OR^{14}$, $OC(O)NR^{15}R^{16}$, $NR^{17}C(O)OR^1$, or $NR^{19}C(O)NR^{20}R^{21}$;

one of $X_2$ and $X_4$ is hydrogen; and the other one of $X_2$ and $X_4$ is hydrogen, halogen, $OR^5$, $C(O)R^6$, $OS(O)_pR^7$, $NR^3R^4$, $NR^1C(O)R^2$, $NR^1S(O)_pR^7$, $S(O)_qR^{10}$, $C(O)OR^{11}$, $C(O)NR^{12}R^{13}$, $OC(O)OR^{14}$, $OC(O)NR^{15}R^{16}$, $NR^{17}C(O)OR^{18}$, $NR^{19}C(O)NR^{20}R^{21}$, $C_1$-$C_8$ alkyl, $C_2$-$C_8$ alkenyl, $C_2$-$C_8$ alkynyl, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring, wherein said alkyl, alkenyl, alkynyl, cycloalkyl, cycloalkenyl, aromatic ring, heteroaromatic ring, and heterocyclic ring is unsubstituted or substituted with one or more $R^a$.

In certain embodiments, the selective HDAC3 inhibitor is a compound of the formula

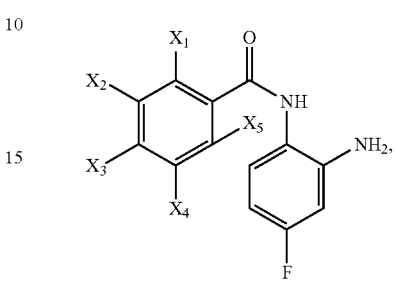

or a pharmaceutically acceptable salt, hydrate, solvate, or prodrug thereof, wherein:

$X_3$ is halogen, $OR^5$, $C(O)R^6$, $OS(O)_pR^7$, $NR^3R^4$, $NR^1C(O)R^2$, $NR^1S(O)_pR^7$, $S(O)_qR^{10}$, $C(O)OR^{11}$, $C(O)NR^{12}R^{13}$, $OC(O)OR^{14}$, $OC(O)NR^{15}R^{16}$, $NR^{17}C(O)OR^{18}$, $NR^{19}C(O)NR^{20}R^{21}$, $C_1$-$C_8$ alkyl, $C_2$-$C_8$ alkenyl, $C_2$-$C_8$ alkynyl, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring, wherein said alkyl, alkenyl, alkynyl, cycloalkyl, cycloalkenyl, aromatic ring, heteroaromatic ring, and heterocyclic ring is unsubstituted or substituted with one or more $R^a$;

one of $X_2$ and $X_4$ is hydrogen; and the other one of $X_2$ and $X_4$ is hydrogen, halogen, or $C_1$-$C_8$ alkyl (e.g., $C_1$-$C_3$ alkyl), wherein said alkyl is unsubstituted or substituted with one or more $R^a$.

In certain embodiments, the selective HDAC3 inhibitor is a compound of the formula

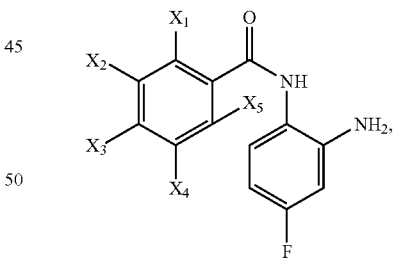

or a pharmaceutically acceptable salt, hydrate, solvate, or prodrug thereof, wherein:

$X_3$ is halogen, $OR^5$, $C(O)R^6$, $OS(O)_pR^7$, $NR^3R^4$, $NR^1C(O)R^2$, $NR^1S(O)_pR^7$, $S(O)_qR^{10}$, $C(O)OR^{11}$, $C(O)NR^{12}R^{13}$, $OC(O)OR^{14}$, $OC(O)NR^{15}R^{16}$, $NR^{17}C(O)OR^{18}$, or $NR^{19}C(O)NR^{20}R^{21}$;

one of $X_2$ and $X_4$ is hydrogen; and the other one of $X_2$ and $X_4$ is hydrogen, halogen, or $C_1$-$C_8$ alkyl (e.g., $C_1$-$C_3$ alkyl), wherein said alkyl is unsubstituted or substituted with one or more $R^a$.

In certain embodiments, the selective HDAC3 inhibitor is a compound of the formula:

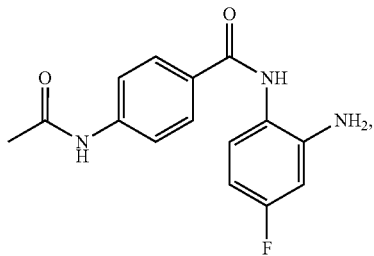

(I-1)

or a pharmaceutically acceptable salt, hydrate, solvate, or prodrug thereof.

In certain embodiments, the selective HDAC3 inhibitor is a compound of the formula:

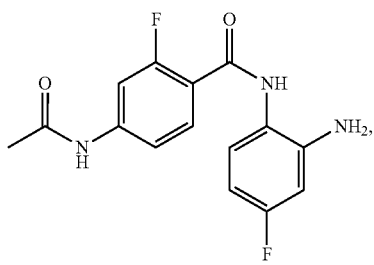

(I-6)

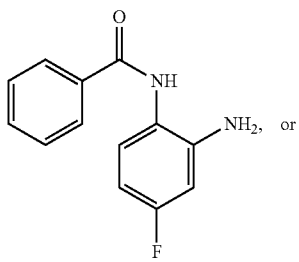

(I-7)

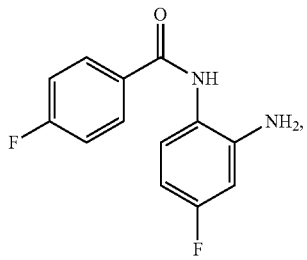

(I-8)

or a pharmaceutically acceptable salt, hydrate, solvate, or prodrug thereof.

In certain embodiments, the selective HDAC3 inhibitor is not of the formula:

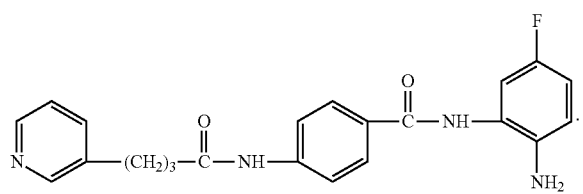

or a pharmaceutically acceptable salt, hydrate, or solvate thereof.

Compounds of Formula (II)

In certain embodiments, the selective HDAC3 inhibitor is a compound of Formula (II):

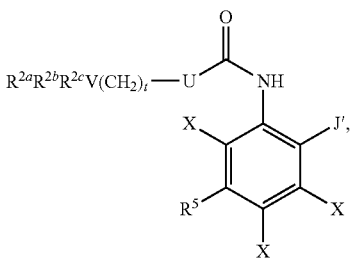

(II)

or a pharmaceutically acceptable salt, hydrate, solvate, or prodrug thereof, wherein:

U is selected from single bond, $CR^{2e}R^{2f}$—$CR^{2g}R^{2h}$, $NR^{2d}$, $NR^{2d}$—$NR^{2d'}$, and O;

J' is selected from $NH_2$, OH, and SH;

V is selected from C and N, provided that when V is N, one of $R^{2a}$, $R^{2b}$, or $R^{2c}$ is absent;

X is selected from hydrogen, deuterium, methyl, $CF_3$, and halogen;

$R^{2a}$ is selected from hydrogen, halogen, OH, $NH_2$, and $C_1$-$C_8$ alkyl;

$R^{2b}$ is selected from hydrogen, halogen, OH, $NH_2$, and $C_1$-$C_8$ alkyl;

$R^{2c}$ is selected from hydrogen, halogen, OH, $NH_2$, and $C_1$-$C_8$ alkyl;

$R^{2d}$ is selected from $NH_2$, hydrogen, and $C_1$-$C_8$ alkyl;

$R^{2d'}$ is selected from $NH_2$, hydrogen, and $C_1$-$C_8$ alkyl;

$R^{2e}$, $R^{2f}$, $R^{2g}$, and $R^{2h}$ are each independently selected from hydrogen, halogen, and $C_1$-$C_4$ alkyl;

or taken together two of $R^{2a}$, $R^{2b}$, and $R^{2c}$ form =O;

or taken together two of $R^{2a}$, $R^{2b}$, and $R^{2c}$ form a $C_3$-$C_8$ cycloalkyl ring, $C_4$-$C_8$ cycloalkenyl ring, or 3 to 8 membered saturated or partially unsaturated heterocyclic ring, and the remaining $R^{2a}$, $R^{2b}$, or $R^{2c}$ is absent or selected from hydrogen, halogen, OH, $NH_2$, and $C_1$-$C_8$ alkyl, further wherein said cycloalkyl, cycloalkenyl, and heterocyclic ring are unsubstituted or substituted with one or more $R^X$;

or taken together two of $R^{2a}$, $R^{2b}$, $R^{2c}$, and $R^{2d}$ form a $C_3$-$C_8$ cycloalkyl ring, $C_4$-$C_8$ cycloalkenyl ring, or 3 to 8 membered saturated or partially unsaturated heterocyclic ring, and the remaining $R^{2a}$, $R^{2b}$, or $R^{2c}$ is selected from hydrogen, halogen, OH, $NH_2$, and $C_1$-$C_8$ alkyl, or $R^{2d}$ is hydrogen, $NH_2$, or $C_1$-$C_8$ alkyl, further wherein said cycloalkyl, cycloalkenyl, and heterocyclic ring are unsubstituted or substituted with one or more $R^X$;

or taken together two of $R^{2a}$, $R^{2b}$, and $R^{2c}$ form an aromatic or heteroaromatic ring and the remaining $R^{2a}$, $R^{2b}$, or $R^{2c}$ is absent, provided that when two of $R^{2a}$, $R^{2b}$, and $R^{2c}$ form an aromatic ring and the remaining $R^{2a}$, $R^{2b}$, or $R^{2c}$ is absent, U is not a single bond when t is 0, further wherein said aromatic and heteroaromatic ring are unsubstituted or substituted with one or more $R^X$;

or taken together $R^{2e}$ and $R^{2f}$ or $R^{2g}$ and $R^{2h}$ form =O;

or taken together two of $R^{2e}$, $R^{2f}$, $R^{2g}$, and $R^{2h}$ on two adjacent carbon atoms together with the bond between said adjacent carbon atoms form a carbon-carbon double bond;

or taken together two of $R^{2e}$, $R^{2}$, $R^{2f}$, $R^{2g}$, and $R^{2h}$ on two adjacent carbon atoms together with the intervening atoms to which they are attached form a 3 to 8 membered saturated or partially saturated ring;

each $R^x$ is independently selected from $(CH_2)_zNH_2$, $(CH_2)_zNHR^3$, $(CH_2)_zNR^3R^3$, $OR^3$, $OCF_3$, $OCH_2F$, $OCHF_2$, $(CH_2)_z$-aromatic ring, $(CH_2)_z$-heterocyclic ring, hydroxyl, halogen, $C_1$-$C_8$ alkyl, $(C_1$-$C_8$ alkyl$)CF_3$, $(C_1$-$C_8$ alkyl$)OH$, $C(O)R^{3'}$ $(CH_2)_zC(O)NH_2$, $(CH_2)_zC(O)NHR^3$, $(CH_2)_zC(O)NR^3R^3$, $(CH_2)_zNHC(O)R^4$, and $(CH_2)_zNR^4C(O)R^4$;

or taken together two $R^x$ attached to the same carbon atom of a cycloalkyl, cycloalkenyl or heterocyclic ring form =O;

or taken together two $R^x$ form a $C_3$-$C_8$ cycloalkyl ring, $C_4$-$C_8$ cycloalkenyl ring, or 3 to 8 membered saturated or partially unsaturated heterocyclic ring, further wherein said cycloalkyl, cycloalkenyl, and heterocyclic ring are unsubstituted or substituted with one or more $R^z$;

or taken together two $R^x$ form an aromatic ring or heteroaromatic ring, further wherein said aromatic and heteroaromatic ring are unsubstituted or substituted with one or more $R^z$;

each $R^z$ is independently selected from halogen, $C_1$-$C_4$ alkyl, OH, $OR^3$, $CF_3$, $OCF_3$, $OCH_2F$, $OCHF_2$, $NH_2$, $NHR^3$, $NR^3R^3$, and $C(O)CH_3$;

$R^3$ is selected from $C_1$-$C_8$ alkyl and $O(C_1$-$C_8$ alkyl$)$;

$R^4$ is selected from $C_1$-$C_8$ alkyl and $CF_3$;

$R^5$ is selected from hydrogen, deuterium, halogen, OH, $OCH_3$, $CF_3$, $CH_3$, and cyclopropyl;

t is selected from 0, 1, and 2, and z is selected from 0, 1, 2, and 3.

In certain embodiments, the selective HDAC3 inhibitor is a compound of the formula:

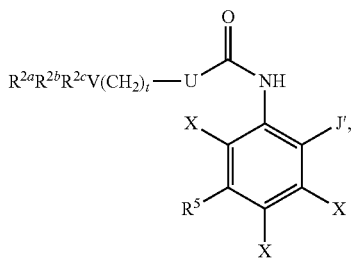

or a pharmaceutically acceptable salt, hydrate, solvate, or prodrug thereof, wherein:

the moiety

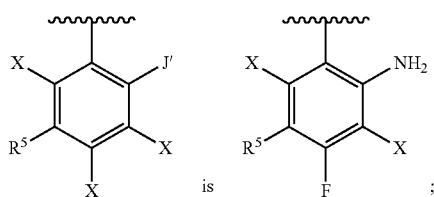

U is selected from a single bond and $NR^{2d}$;

V is selected from C and N, provided that when V is N, one of $R^{2a}$, $R^{2b}$, or $R^{2c}$ is absent;

each X is independently selected from hydrogen, deuterium, methyl, $CF_3$, and halogen;

$R^{2a}$ is selected from hydrogen, halogen, OH, $NH_2$, and $C_1$-$C_8$ alkyl;

$R^{2b}$ is selected from hydrogen, halogen, OH, $NH_2$, and $C_1$-$C_8$ alkyl;

$R^{2c}$ is selected from hydrogen, halogen, OH, $NH_2$, and $C_1$-$C_8$ alkyl;

$R^{2d}$ is selected from $NH_2$ and $C_1$-$C_8$ alkyl;

provided that:

taken together two of $R^{2a}$, $R^{2b}$, and $R^{2c}$ form a $C_3$-$C_8$ cycloalkyl ring, $C_4$-$C_8$ cycloalkenyl ring, or 3 to 8 membered, saturated or partially unsaturated, heterocyclic ring containing 1, 2, 3, or 4 nitrogen atoms, and the remaining $R^{2a}$, $R^{2b}$, or $R^{2c}$ is absent or selected from hydrogen, halogen, OH, $NH_2$, and $C_1$-$C_8$ alkyl, wherein:

said cycloalkyl ring formed by taking together two of $R^{2a}$, $R^{2b}$, and $R^{2c}$ is substituted with two or more $R^x$, wherein two $R^x$ are taken together to form a $C_3$-$C_8$ cycloalkyl ring that is substituted with one or more $R^z$ or is unsubstituted, $C_4$-$C_8$ cycloalkenyl ring, or 3 to 8 membered, saturated or partially unsaturated, heterocyclic ring, further wherein said cycloalkenyl ring and heterocyclic ring are unsubstituted or substituted with one or more $R^z$, or to form an aromatic ring or heteroaromatic ring, further wherein said aromatic ring and heteroaromatic ring are monocyclic or bicyclic, and are unsubstituted or substituted with one or more $R^z$; and said cycloalkenyl ring formed by taking together two of $R^{2a}$, $R^{2b}$, and $R^{2c}$, and heterocyclic ring formed by taking together two of $R^{2a}$, $R^{2b}$, and $R^{2c}$ are unsubstituted or substituted with one or more $R^X$;

or taken together $R^{2d}$ and one of $R^{2a}$, $R^{2b}$, and $R^{2c}$ form a 3 to 8 membered, saturated or partially unsaturated, heterocyclic ring, and: the remaining $R^{2a}$, $R^{2b}$, or $R^{2c}$ is selected from hydrogen, halogen, OH, $NH_2$, and $C_1$-$C_8$ alkyl, or taken together two of the remaining $R^{2a}$, $R^{2b}$, and $R^{2c}$ form =O; wherein said heterocyclic ring is unsubstituted or substituted with one or more $R^X$;

or taken together two of $R^{2a}$, $R^{2b}$, and $R^{2c}$ form an aromatic or heteroaromatic ring and the remaining $R^{2a}$, $R^{2b}$, or $R^{2c}$ is absent, provided that when two of $R^{2a}$, $R^{2b}$, and $R^{2c}$ form an aromatic or heteroaromatic ring and the remaining $R^{2a}$, $R^{2b}$, or $R^{2c}$ is absent, U is not a single bond, wherein: said aromatic ring is monocyclic, bicyclic, or tricyclic, and is unsubstituted or substituted with one or more $R^X$; and said heteroaromatic ring is monocyclic or bicyclic, and is unsubstituted or substituted with one or more $R^x$;

each $R^x$ is independently selected from $(CH_2)_zNH_2$, $(CH_2)_zNHR^3$, $(CH_2)_zNR^3R^3$, $OR^3$, $OCF_3$, $OCH_2F$, $OCHF_2$, $(CH_2)_z$-aromatic ring, $(CH_2)_z$-heterocyclic ring, hydroxyl, halogen, $C_1$-$C_8$ alkyl, $(C_1$-$C_5$ alkyl$)CF_3$, $(C_1$-$C_8$ alkyl$)OH$, $C(O)R^3$, $(CH_2)_zC(O)NH_2$, $(CH_2)_zC(O)NHR^3$, $(CH_2)_zC(O)NR^3R^3$, $(CH_2)_zNHC(O)R^4$, and $(CH_2)_zNR^4C(O)R^4$, wherein the aromatic ring is monocyclic, bicyclic, or tricyclic, and the heterocyclic ring is 3 to 8 membered;

or taken together two $R^x$ attached to the same carbon atom of a cycloalkyl, cycloalkenyl, or heterocyclic ring form =O;

or taken together two $R^x$ form a $C_3$-$C_8$ cycloalkyl ring, $C_4$-$C_8$ cycloalkenyl ring, or 3 to 8 membered, saturated or partially unsaturated, heterocyclic ring, wherein said cycloalkyl ring, cycloalkenyl ring, and heterocyclic ring are unsubstituted or substituted with one or more $R^z$;

or taken together two $R^x$ form an aromatic ring or heteroaromatic ring, wherein: said aromatic ring is monocyclic, bicyclic, or tricyclic, and is unsubstituted or substituted with one or more $R^z$; and said heteroaromatic ring is monocyclic or bicyclic, and is unsubstituted or substituted with one or more $R^z$;

each $R^z$ is independently selected from halogen, $C_1$-$C_4$ alkyl, OH, $OR^3$, $CF_3$, $OCF_3$, $OCH_2F$, $OCHF_2$, $NH_2$, $NHR^3$, $NR^3R^3$, and $C(O)CH_3$;

$R^3$ is $C_1$-$C_8$ alkyl;

$R^4$ is selected from $C_1$-$C_8$ alkyl and $CF_3$;

$R^5$ is selected from hydrogen, deuterium, halogen, OH, $OCH_3$, $CF_3$, $CH_3$, and cyclopropyl;

t is 0, and z is selected from 0, 1, 2, and 3.

In certain embodiments, $R^{2a}R^{2b}R^{2c}V$— is:

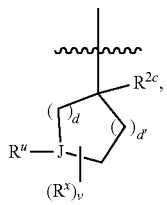

wherein:

J is selected from N, O, C, and S;

when J is N or C, $R^u$ is selected from hydrogen, $C_1$-$C_8$ alkyl, ($C_1$-$C_8$ alkyl)$CF_3$, ($C_1$-$C_8$ alkyl)OH, and $C(O)R^{3a}$; and when J is O or S, $R^u$ is absent;

$R^{3a}$ is $C_1$-$C_8$ alkyl;

v is selected from 0, 1, 2, 3, 4, 5, 6, 7, and 8; and d and d' are each independently selected from 0, 1, 2, and 3, provided that the ring formed by taking together $R^e a$ and $R^{2b}$ is a 3 to 8 membered ring.

In certain embodiments, $R^{2a}R^{2b}R^{2c}V$ is:

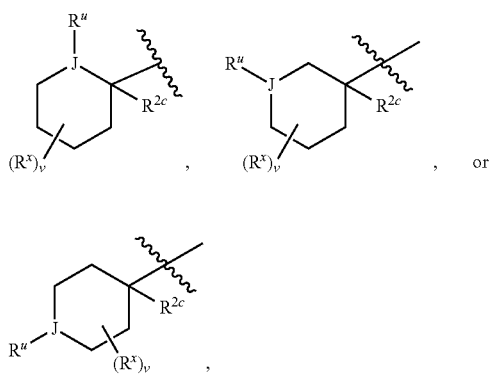

wherein:

J is selected from N, O, C, and S;

when J is N or C, $R^u$ is selected from hydrogen, $C_1$-$C_8$ alkyl, ($C_1$-$C_8$ alkyl)$CF_3$, ($C_1$-$C_8$ alkyl)OH, and $C(O)R^{3a}$; and when J is O or S, $R^u$ is absent;

$R^{3a}$ is $C_1$-$C_8$ alkyl; and v is selected from 0, 1, 2, 3, 4, 5, 6, 7, and 8.

In certain embodiments, $R^{2a}R^{2b}R^{2c}V$— is:

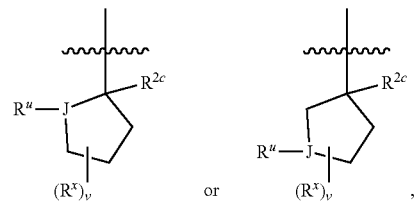

wherein:

J is selected from N, O, C, and S;

when J is N or C, $R^u$ is selected from hydrogen, $C_1$-$C_8$ alkyl, ($C_1$-$C_8$ alkyl)$CF_3$, ($C_1$-$C_8$ alkyl)OH, and $C(O)R^{3a}$; and when J is O or S, $R^u$ is absent;

$R^{3a}$ is $C_1$-$C_8$ alkyl; and v is selected from 0, 1, 2, 3, 4, 5, 6, or 7.

In certain embodiments, $R^{2a}R^{2b}R^{2c}V$— is:

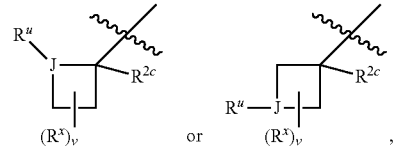

wherein:

J is selected from N, O, C, and S;

when J is N or C, $R^u$ is selected from hydrogen, $C_1$-$C_8$ alkyl, ($C_1$-$C_8$ alkyl)$CF_3$, ($C_1$-$C_8$ alkyl)OH, and $C(O)R^{3a}$; and when J is O or S, $R^u$ is absent;

$R^{3a}$ is $C_1$-$C_8$ alkyl; and v is selected from 0, 1, 2, 3, 4, or 5.

In certain embodiments, $R^{2a}R^{2b}R^{2c}V$— is:

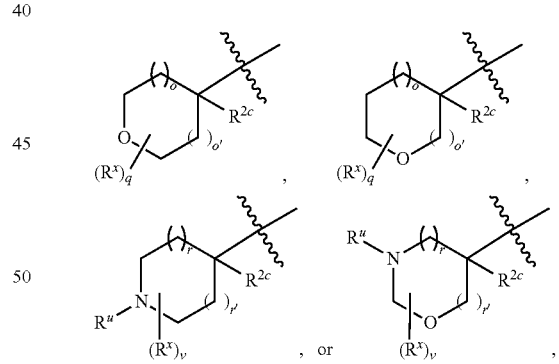

wherein:

o and o' are each independently selected from 0, 1, and 2, provided that the ring formed by taking together $R^{2a}$ and $R^{2b}$ is a 3 to 8 membered ring;

r and r' are each independently selected from 0, 1, and 2, provided that the ring formed by taking together $R^{2a}$ and $R^{2b}$ is a 3 to 8 membered ring;

q is selected from 0, 1, 2, 3, 4, 5, 6, 7, and 8;

$R^u$ is selected from hydrogen, $C_1$-$C_8$ alkyl, ($C_1$-$C_8$ alkyl)$CF_3$, ($C_1$-$C_8$ alkyl)OH, and $C(O)R^{3a}$;

$R^{3a}$ is $C_1$-$C_8$ alkyl; and v is selected from 0, 1, 2, 3, 4, 5, 6, 7, and 8.

In certain embodiments, $R^{2a}R^{2b}R^{2c}V-$ is:

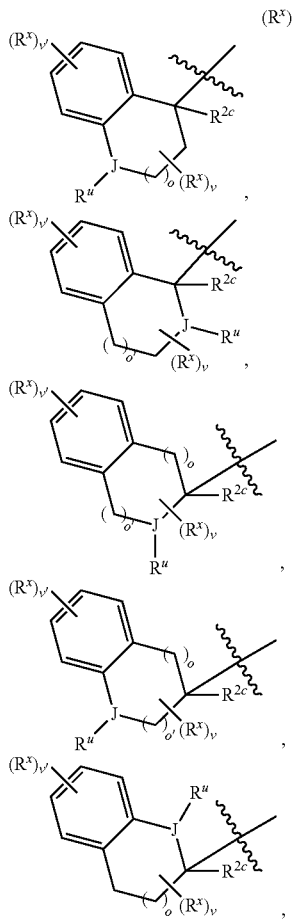

wherein:
J is selected from N, O, C, and S;
when J is N or C, $R^u$ is selected from hydrogen, $C_1$-$C_8$ alkyl, $(C_1$-$C_8$ alkyl)$CF_3$, $(C_1$-$C_8$ alkyl)OH, $C(O)R^{3a}$; and when J is O or S, $R^u$ is absent;
$R^{3a}$ is $C_1$-$C_8$ alkyl;
v is selected from 0, 1, 2, 3, 4, 5, 6, 7, and 8;
v' is selected from 0, 1, 2, 3, and 4; and
o and o' are each independently selected from 0, 1, 2, and 3, provided that the ring formed by taking together $R^{2a}$ and $R^{2b}$ is a 3 to 8 membered ring.

In certain embodiments, $R^{2a}R^{2b}R^{2c}V-$ is:

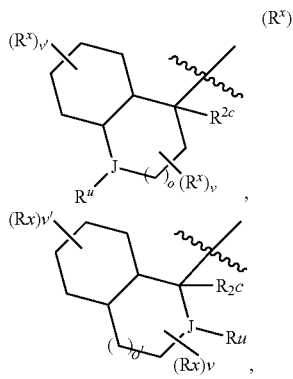

-continued

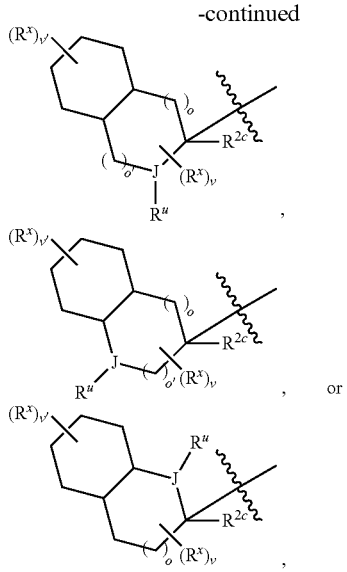

wherein:
J is selected from N, O, C, and S;
when J is N or C, $R^u$ is selected from hydrogen, $C_1$-$C_8$ alkyl, $(C_1$-$C_8$ alkyl)$CF_3$, $(C_1$-$C_8$ alkyl)OH, $C(O)R^{3a}$; and when J is O or S, $R^u$ is absent;
$R^{3a}$ is $C_1$-$C_8$ alkyl;
v is selected from 0, 1, 2, 3, 4, 5, 6, 7, and 8;
v' is selected from 0, 1, 2, 3, and 4; and
o and o' are each independently selected from 0, 1, 2, and 3, provided that the ring formed by taking together $R^{2a}$ and $R^{2b}$ is a 3 to 8 membered ring.

In certain embodiments, $R^{2a}R^{2b}R^{2c}V-$ is:

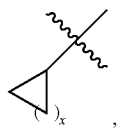

wherein x is selected from 1, 2, 3, and 4.

In certain embodiments, $R^{2a}R^{2b}R^{2c}V-$ is:

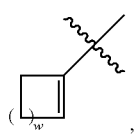

wherein w is selected from 1, 2, and 3.

In certain embodiments, $R^{2a}R^{2b}R^{2c}V-$ is selected from the group consisting of:

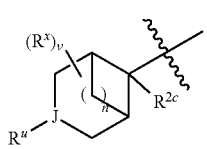 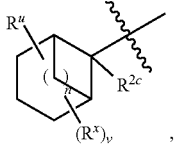

-continued

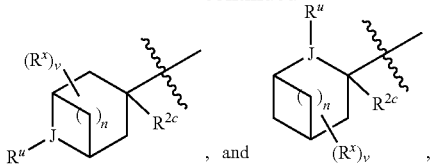

, and wherein:

J is selected from N, O, C, and S;

when J is N or C, $R^u$ is selected from hydrogen, $C_1$-$C_8$ alkyl, ($C_1$-$C_5$ alkyl)$CF_3$, ($C_1$-$C_5$ alkyl)OH, C(O)$R^{3a}$; and when J is O or S, $R^u$ is absent;

$R^{3a}$ is $C_1$-$C_8$ alkyl;

n is 0, 1, 2, or 3; and v is selected from 0, 1, 2, 3, 4, 5, 6, 7, and 8.

In certain embodiments, $R^{2a}R^{2b}R^{2c}V—$ is

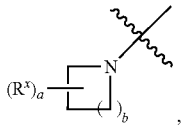

wherein: b is selected from 0, 1, 2, and 3; and a is selected from 0, 1, 2, 3, 4, 5, 6, 7, 8, 9, and 10. In certain embodiments, $R^{2a}R^{2b}R^{2c}V—$ is

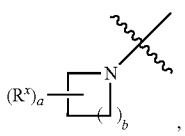

wherein:

taken together two $R^x$ form a $C_3$-$C_8$ cycloalkyl ring, $C_4$-$C_8$ cycloalkenyl ring, or 3 to 8 membered, saturated or partially unsaturated, heterocyclic ring;

a is 0, 1, 2, 3, 4, 5, 6, 7, 8, 9, or 10; and b is 0, 1, 2, or 3.

In certain embodiments, $R^{2a}R^{2b}R^{2c}V—$ is

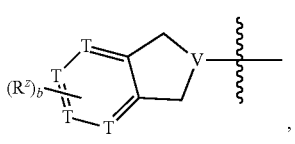

wherein:

V is N or CH;

each T is independently CH, $CR^z$, or N;

each $R^z$ is independently selected from halogen, $C_1$-$C_4$ alkyl, OH, $OR^3$, $CF_3$, $OCF_3$, $OCH_2F$, $OCHF_2$, $NH_2$, $NHR^3$, $NR^3R^3$, and C(O)$CH_3$;

each $R^3$ is independently $C_1$-$C_8$ alkyl or O($C_1$-$C_8$ alkyl); and b is 0, 1, 2, 3, or 4.

In certain embodiments, $R^{2a}R^{2b}R^{2c}V—$ is:

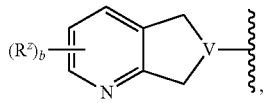

wherein:

V is N or CH;

each $R^z$ is independently halogen, $C_1$-$C_4$ alkyl, OH, $OR^3$, $CF_3$, $OCF_3$, $OCH_2F$, $OCHF_2$, $NH_2$, $NHR^3$, $NR^3R^3$, or C(O)$CH_3$;

each $R^3$ is independently $C_1$-$C_8$ alkyl or O($C_1$-$C_8$ alkyl); and b is 0, 1, 2, or 3.

In certain embodiments, $R^{2a}R^{2b}R^{2c}V—$ is:

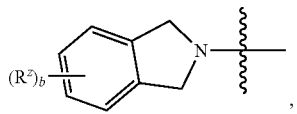

wherein:

each $R^z$ is independently halogen, $C_1$-$C_4$ alkyl, OH, $OR^3$, $CF_3$, $OCF_3$, $OCH_2F$, $OCHF_2$, $NH_2$, $NHR^3$, $NR^3R^3$, or C(O)$CH_3$;

each $R^3$ is independently $C_1$-$C_8$ alkyl or O($C_1$-$C_8$ alkyl); and b is 0, 1, 2, 3, or 4.

In certain embodiments, $R^{2a}R^{2b}R^{2c}V—$ is:

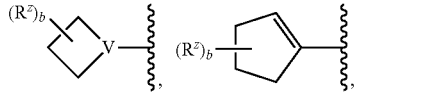

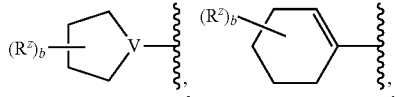

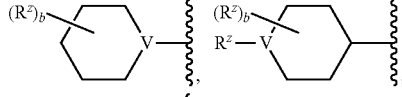

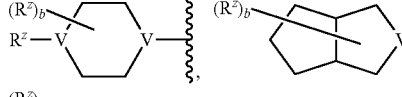

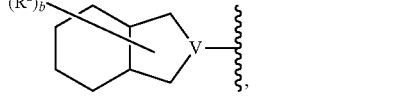

wherein:

each V is independently N or CH;

each $R^z$ is independently halogen, $C_1$-$C_4$ alkyl, OH, $OR^3$, $CF_3$, $OCF_3$, $OCH_2F$, $OCHF_2$, $NH_2$, $NHR^3$, $NR^3R^3$, or C(O)$CH_3$;

each $R^3$ is independently $C_1$-$C_8$ alkyl or O($C_1$-$C_8$ alkyl); and b is 0, 1, 2, 3, 4, 5, 6, 7, 8, 9, or 10, as valency permits.

In certain embodiments, $R^{2a}R^{2b}R^{2c}V-$ is:

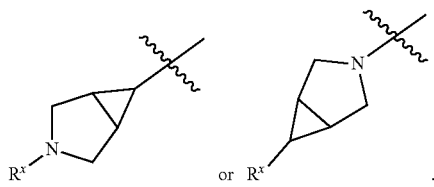

In certain embodiments, $R^5$ is hydrogen.
In certain embodiments, the moiety

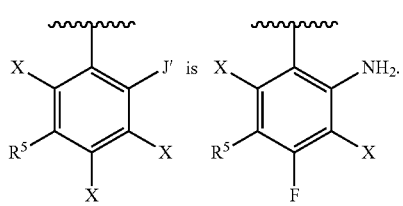

In certain embodiments, each X is hydrogen.
In certain embodiments, U is a single bond. In certain embodiments, U is $CH_2-CH_2$.
In certain embodiments, t is 0. In certain embodiments, t is 1. In certain embodiments, t is 2.
In certain embodiments, $R^5$ is H. In certain embodiments, $R^5$ is halogen (e.g., F). In certain embodiments, $R^5$ is unsubstituted $C_{1-6}$ alkyl. In certain embodiments, $R^5$ is $C_{1-6}$ alkyl substituted with one or more halogen, as valency permits.
In certain embodiments, the selective HDAC3 inhibitor is a compound of the formula:

(II-207)
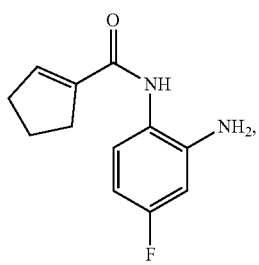

(II-219)
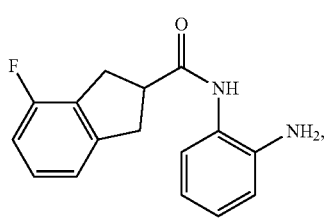

(II-220)
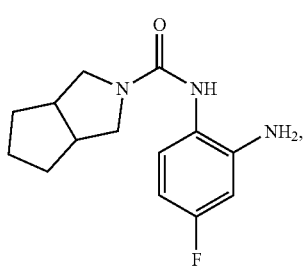

(II-222)
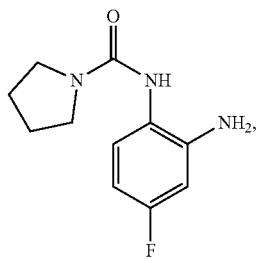

(II-223)
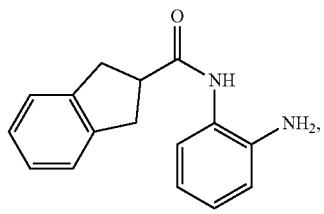

(II-228)
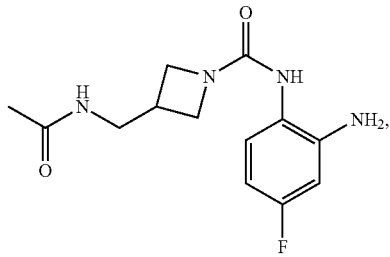

(II-234)
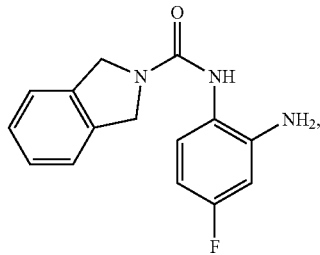

(II-237)
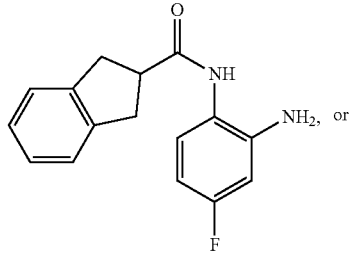

or (II-243)
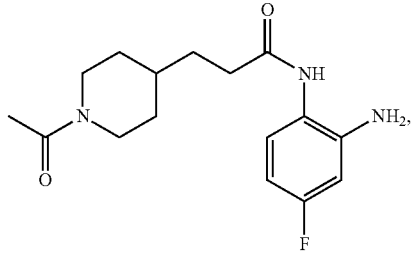

or a pharmaceutically acceptable salt, hydrate, solvate, or prodrug thereof.

Compounds of Formula (III)

In certain embodiments, the selective HDAC3 inhibitor is a compound of the formula:

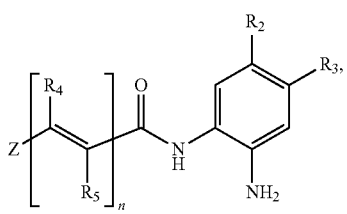

(III)

or a pharmaceutically acceptable salt, hydrate, solvate, or prodrug thereof, wherein n=0;

Z is $R_1$—V-Cy-U—Ar$^t$/Het$^t$;

Ar$^t$/Het$^t$ is:
(i) phenyl, pyridyl, or pyrimidinyl, each of which is optionally substituted with from 1-3 $R^p$; provided that the point of connection on said phenyl, pyridyl, or pyrimidinyl to U and the point of connection on said phenyl, pyridyl, or pyrimidinyl to the amide carbonyl do not result in 1,2-relation to one another on said phenyl, pyridyl, or pyrimidinyl; wherein $R^p$ at each occurrence is, independently, selected from H, F, chloro, $CH_3$, $CF_3$, $OCH_3$, $OCF_3$, and $OCHF_2$;
(ii) a 5-membered heteroaryl selected from pyrazolyl, pyrrolyl, thiazolyl, thienyl, furanyl, imidazolyl, oxazolyl, oxadiazolyl, thiadiazolyl, isoxazolyl, and isothiazolyl, each of which is optionally substituted with from 1-3 $R^p$; provided that the point of connection on said 5-membered heteroaryl to U and the point of connection on said 5-membered heteroaryl to the amide carbonyl do not result in 1,2-relation to one another on said 5-membered heteroaryl;
(iii) a 8-, 9- or 10-membered bicyclic heteroaryl selected from benzothienyl, benzofuranyl, benzothioazolyl, benzoxazolyl, indolyl, isoindolonyl, indolizinyl, pyrolopyrimidinyl, pyrazolopyridinyl, imidazopyridinyl, imidazopyridazinyl, triazolopyridinyl, imidazothiazolyl, imidazooxazolyl, quinolinyl, and naphthyridinyl; each of which is optionally substituted with from 1-3 $R^p$;

$R_1$ is:
(i) hydrogen; or
(ii) C6-C10 aryl, which is optionally substituted with from 1-3 $R^q$; or
(iii) monocyclic or bicyclic heteroaryl including from 5-10 ring atoms, which is optionally substituted with from 1-3 $R^q$; wherein from 1-4 of the ring atoms is/are a heteroatom independently selected from O, N, N—H, N—$R^q$, and S; or
(iv) heterocyclyl including from 4-10 ring atoms, which is optionally substituted with from 1-3 $R^q$; wherein from 1-4 of the ring atoms is/are a heteroatom independently selected from O, N, N—H, N—$R^q$, and S; and each occurrence of $R^q$ is independently selected from the group consisting of.
halogen;
C1-C6 alkyl; fluoru(C1-C6)alkyl;
hydroxyl;
hydroxy($C_1$-$C_4$)alkyl;
C1-C6 alkoxy; fluoro(C1-C6)alkoxy;
(C1-C6 alkyl)C(O)—;
(C1-C6 alkyl)NH—; (C1-C6 alkyl)$_2$N—;

—N*($R^{q'}$)$_2$, wherein $R^{q'}$—N*—$R^{q'}$ together form a saturated ring having 5 or 6 ring atoms, wherein 1 or 2 ring atoms in addition to the N* ring atom is/are optionally a heteroatom independently selected from NH, N(alkyl), O, or S;
formyl; formyl(C1-C4) alkyl; cyano; cyano(C1-C4) alkyl;
benzyl; benzyloxy;
heterocyclyl-(C0-C6) alkyl, wherein the heterocyclyl portion includes 5 or 6 ring atoms, in which 1 or 2 of the ring atoms is/are a heteroatom independently selected from NH, N(alkyl), O, or S, and when said alkyl portion is present, said alkyl portion serves as the point of attachment to $R_1$; otherwise in the case of C0 alkyl, a heterocyclyl carbon ring atom serves as the point of attachment of the heterocyclyl to $R_1$;
phenyl or heteroaryl including from 5-6 ring atoms, wherein from 1-4 of the ring atoms is/are a heteroatom independently selected from O, N, N—H, N—$R^{q''}$, and S, each of which is optionally substituted with from 1-3 $R^{q''}$;
$SO_2$—(C1-C6)alkyl; SO—(C1-C6)alkyl; and
nitro;

each occurrence of $R^{q''}$ is independently selected from the group consisting of:
halogen;
C1-C6 alkyl; fluoru(C1-C6)alkyl;
hydroxyl;
hydroxy($C_1$-$C_4$)alkyl;
C1-C6 alkoxy; fluoro(C1-C6)alkoxy;
(C1-C6 alkyl)C(O)—;
(C1-C6 alkyl)NH—; (C1-C6 alkyl)$_2$N—;
formyl; formyl($C_1$-$C_4$) alkyl; cyano; cyano($C_1$-$C_4$) alkyl;
benzyl; benzyloxy;
heterocyclyl-(C0-C6) alkyl, wherein the heterocyclyl portion includes 5 or 6 ring atoms, in which 1 or 2 of the ring atoms is/are a heteroatom independently selected from NH, N(alkyl), O, or S, and when said alkyl portion is present, said alkyl portion serves as the point of attachment to $R_1$; otherwise in the case of C0 alkyl, a heterocyclyl carbon ring atom serves as the point of attachment of the heterocyclyl to $R_1$;
phenyl or heteroaryl including from 5-6 ring atoms, wherein from 1-4 of the ring atoms is/are a heteroatom independently selected from O, N, N—H, N—(C1-C6 alkyl), and S;
$SO_2$—(C1-C6)alkyl; SO—(C1-C6)alkyl; and
nitro:

U is:
(i) =CR$^r$, wherein the carbon atom in =CR$^r$ is doubly bonded to a ring atom of Cy, thereby forming an exocyclic double bond; or
(ii) —U'—(R$^s$)$_2$— or —C(R$^s$)$_2$—U'—;
wherein:
R$^r$ is hydrogen, F, C1-C6 alkyl, fluoro(C1-C6)alkyl, C3-C6 cycloalkyl, C1-C6 alkoxy. C1-C6 fluoroalkoxy, or cyano;
each occurrence of R$^s$ is independently selected from H, F, OH, C1-C6 alkyl, C3-C6 cycloalkyl, $NH_2$, OCO—(C1-C6 alkyl), OCO—(C3-C6 cycloalkyl), C1-C6 alkoxy C1-C6 fluoroalkoxy, and cyano; or
R$^s$—C—R$^s$ together form C3-C6 cycloalkyl or heterocyclyl including 3-6 ring atoms, in which one of the heterocyclyl ring atoms is selected from O; S(O)$_m$, wherein m is 0-2 and NR$^u$;
each occurrence of R$^u$ is independently selected from H, C1-C6 alkyl, —C(=O)H, —C(=O)R$^v$, C(=O)O (C1-C6 alkyl), C(=O)N(R$^w$)$_2$, and SO$_2$—R$^v$, wherein R$^v$ is selected from C1-C6 alkyl, CH$_2$-(heteroaryl including 5-10 ring atoms), CH$_2$—(C6-C10 aryl), and C6-C10 aryl; and each occurrence of R$^w$ is independently selected from H, C1-C6 alkyl, CH$_2$-(heteroaryl including 5-10 ring atoms), CH$_2$—(C6-C10 aryl), and C6-C10 aryl, wherein the aryl and heteroaryl portion in R$^v$ and R$^w$ can be optionally substituted with one or more independently selected substituents selected from F, C1-C6 alkyl, fluoro(C1-C6)alkyl, C3-C6 cycloalkyl, C1-C6 alkoxy, C1-C6 fluoroalkoxy, and cyano;

U' is a bond; O; NR$^u$; S(O)$_m$; CH$_2$; or U''-CH$_2$—;
wherein U'' is O; NR$^u$; or S(O)$_m$ and m is 0-2;

Cy is C4-C10 cycloalkyl or saturated heterocyclyl including 4-10 ring atoms, wherein from 1-3 heteroatoms are independently selected from N—H, NR$^{x'}$, and S(O)$_m$; m is 0-2; R$^{x'}$ is defined as R$^{q''}$; and Cy is optionally substituted with from 1-3 R$^x$; and each occurrence of R$^x$ is independently selected from F, OH, C1-C6 alkyl, fluoro(C1-C6)alkyl, C3-C6 cycloalkyl, C1-C6 alkoxy, C1-C6 fluoroalkoxy, and cyano; and wherein when the heterocyclyl contains a secondary amine as part of its structure, then:

(i) V is linked through the nitrogen of the secondary amine portion of the heterocyclyl; and
(ii) U is linked to Cy via a Cy ring carbon atom; wherein the bond between U and the Cy ring carbon is a single or double bond; and
(iii) the Cy ring carbon atom that is attached to U is not adjacent to Cy ring nitrogen atom that is attached to V;

V is:
(i) —V'—C(R$^y$)$_2$— or —C(R$^y$)$_2$—V'—; or
(ii) O, NR$^z$, or S(O)$_m$, wherein m is 0-2; or
(iii) —CH=CH—, C=O, C(R$^y$)$_2$—C(=O), —C(=O)—C(R$^y$)$_2$—, —SO$_2$NR$^z$, NR$^z$SO$_2$, —C(=O)NR$^z$, or NR$^z$C(=O); wherein:
each occurrence of R$^y$ is independently selected from H, F, OH, C1-C6 alkyl, C3-C6 cycloalkyl, NH$_2$, OCO—(C1-C6 alkyl), OCO—(C3-C6 cycloalkyl), C1-C6 alkoxy C1-C6 fluoroalkoxy, and cyano; or
R$^y$—C—R$^y$ together form (C3-C6 cycloalkyl or heterocyclyl including 3-6 ring atoms, in which one of the heterocyclyl ring atoms is selected from O; S(O), and NR$^{aa}$, and m is 0-2;
each occurrence of R$^z$ and R$^{aa}$ is independently selected from H, C1-C6 alkyl, —C(=O)H, —C(=O)R$^v$, C(=O)O(C1-C6 alkyl), C(=O)N(R$^w$)$_2$, and SO$_2$—R$^v$, wherein R$^v$ is selected from C1-C6 alkyl, CH$_2$-(heteroaryl including 5-10 ring atoms), CH$_2$—(C6-C10 aryl), and C6-C10 aryl; and each occurrence of R$^w$ is independently selected from H, C1-C6 alkyl, CH$_2$-(heteroaryl including 5-10 ring atoms), CH$_2$—(C6-C10 aryl), and C6-C10 aryl;

V' is a bond; O; NR$^u$; S(O)$_m$; —C(O)—O—(CR$^y_2$)$_{0-2}$—, —(CR$^y_2$)$_{0-2}$—O—C(O)—C(O)—, C(R$^y$)$_2$—C(R$^y$)$_2$; —(R$^y$)$_2$—V''; or V''—C(R$^y$)$_2$—; wherein V'' is O; NR$^z$; or S(O)$_m$, and m is 0-2; wherein each occurrence of R$^u$ is independently selected from H, C1-C6 alkyl, —C(=O) H, —C(=O)R$^v$, C(=O)O(C1-C6 alkyl), C(=O)N (R$^w$)$_2$ and SO$_2$—R$^v$, wherein R$^v$ is selected from C1-C6 alkyl, CH$_2$-(heteroaryl including 5-10 ring atoms), CH$_2$—(C6-C10 aryl), and C6-C10 aryl, and each occurrence of R$^v$ is independently selected from H, F, OH, C1-C6 alkyl, C3-C6 cycloalkyl, NH$_2$, OCO—(C1-C6 alkyl), OCO—(C3-C6 cycloalkyl), C1-C6 alkoxy C1-C6 fluoroalkoxy, and cyano;

R$_2$ is selected from H, F, Cl, CF$_3$, CF$_2$CF$_1$, CH$_2$CF$_3$, OCF$_3$, OCHF$_2$, phenyl; phenyl substituted with from 1-3 substituents independently selected from F, OH, C1-C6 alkyl, fluoro(C1-C6) alkyl C3-C6 cycloalkyl, NH$_2$, C1-C6 alkoxy, C1-C6 fluoroalkoxy, and cyano; thienyl; thiazolyl; and pyrazol-1-yl; and R$_3$ is F.

In certain embodiments, R$_2$ is H. In certain embodiments, R$_2$ is F. In certain embodiments, R$_2$ is Cl. In certain embodiments, R$_2$ is CF$_3$, CF$_2$CF$_3$, CH$_2$CF$_3$, OCF$_3$, or OCHF$_2$.

In certain embodiments, the selective HDAC3 inhibitor is a compound of the formula:

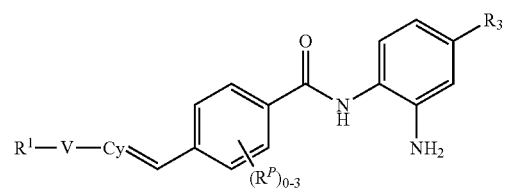

wherein:
R$^3$ is F;
R$^p$ is Cl or F;
Cy is a saturated heterocyclyl having 4-8 ring atoms, where at least one hetero atom is NH or N(C$_{1-6}$ alkyl) to form a secondary amine or tertiary amine, respectively, and optionally one or two additional heteroatoms are independently selected from the group consisting of O, NH, and N(C$_{1-6}$ alkyl); wherein a ring atom of Cy is bonded to the exocyclic double bond;
V is C(R$^y$)$_2$;
each R$^y$ is independently selected from the group consisting of H, F, C$_{1-6}$ alkyl, and C$_{3-6}$ cycloakyl;
R$^1$ is H, phenyl, or monocyclic or bicyclic heteroaryl, where the phenyl and heteroaryl are each optionally substituted with 1-3 Rq; and
R$^q$ is independently halogen OH, C$_{1-6}$ alkyl, fluoro(C$_{1-6}$ alkyl), hydroxy(C$_{1-4}$ alkyl), C$_{1-6}$ alkoxy, or fluoro(C$_{1-6}$ alkoxy);

or a pharmaceutically acceptable salt, hydrate, solvate, or prodrug thereof.

In certain embodiments, the selective HDAC3 inhibitor is a compound of the formula:

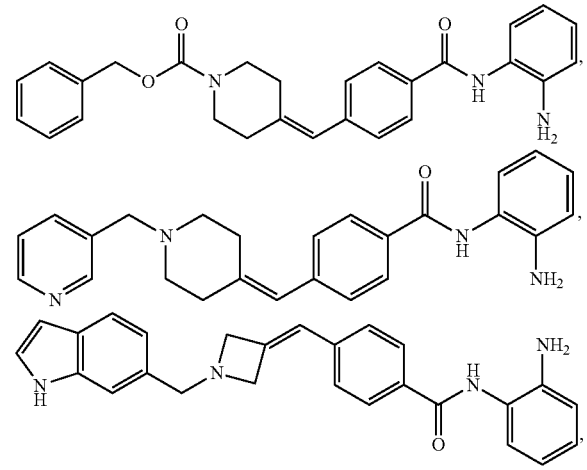

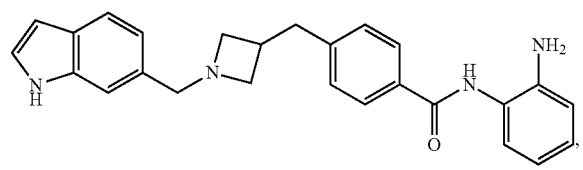
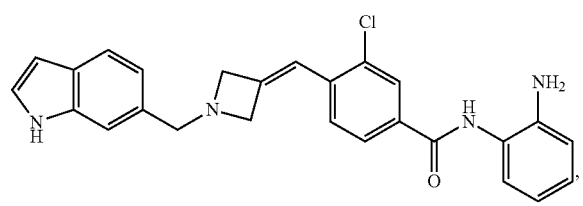
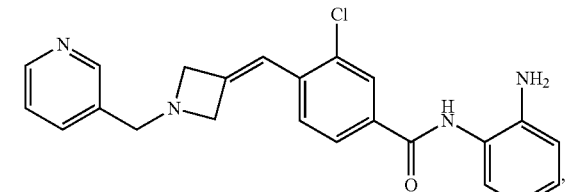
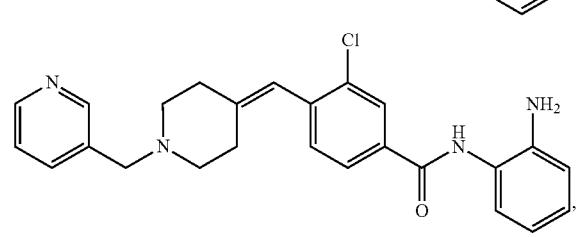
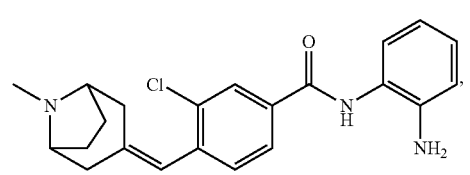
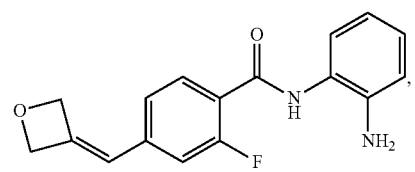
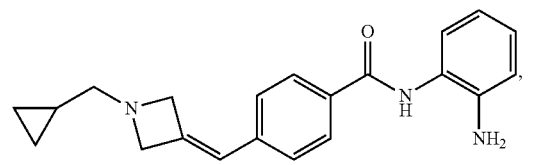
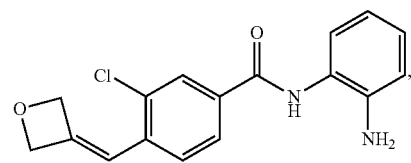
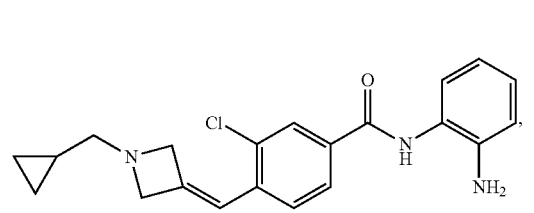
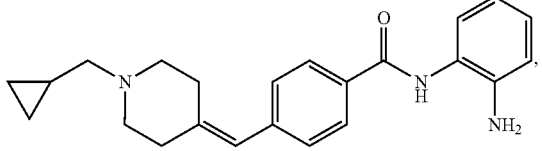
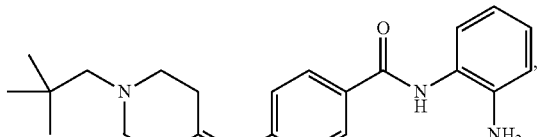
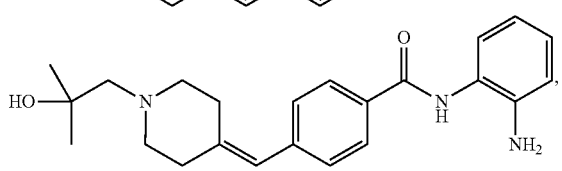
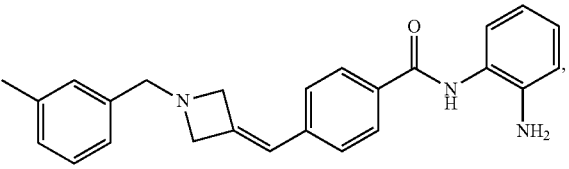
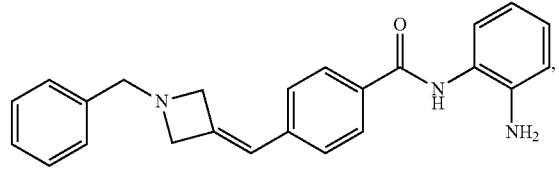
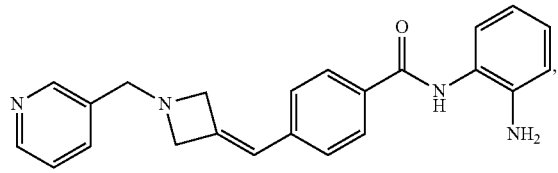
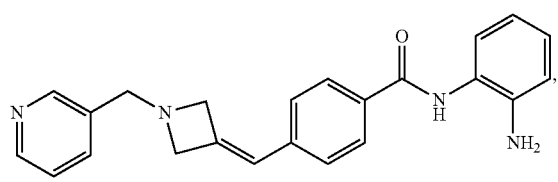
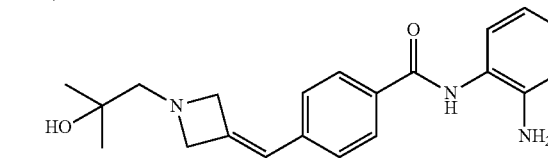
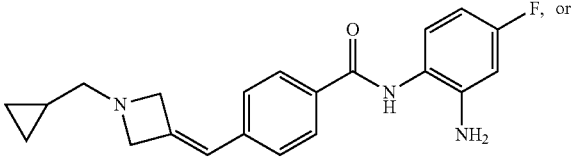
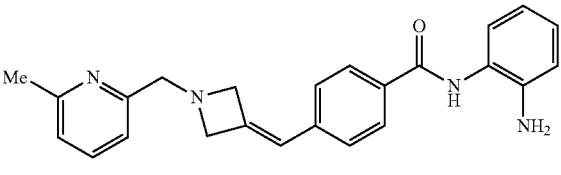
or a pharmaceutically acceptable salt, hydrate, solvate, or prodrug thereof.

In certain embodiments, wherein the selective HDAC3 inhibitor is a compound of the formula:

*[Chemical structure: cyclopropylmethyl-azetidinylidene-methyl-benzamide-N-(2-amino-4-fluorophenyl)]* or a pharmaceutically acceptable salt, hydrate, solvate, or prodrug thereof.

Compounds of Formula (IV)

In certain embodiments, the selective HDAC3 inhibitor is a compound of the formula:

$$Cy^1\text{-}L^1\text{-}Y\text{-}N(R^1)\text{-}L^2\text{-}C(=O)\text{-}NH\text{-}Ar^2 \quad (IV)$$

or a pharmaceutically acceptable salt, hydrate, solvate, or prodrug thereof, wherein:

Y is C(=O);

$Ar^2$ is selected from the group consisting of $C_{6-10}$ aryl and benzo[d][1,3]dioxolyl; wherein said $C_{6-10}$ aryl and benzo[d][1,3]dioxolyl are each substituted at one ortho position by $NH_2$ and at additional positions by m independently selected $R^z$ groups;

$L^2$ is selected from straight chain $C_{4-6}$ alkylene and straight chain $C_{4-6}$ alkenylene wherein 1 or 2 carbon atoms of said straight chain $C_{4-6}$ alkylene, or straight chain $C_{4-6}$ alkenylene is optionally replaced by a group independently selected from the group consisting of —O—, —S—, —S(=O)—, —S(=O)$_2$—, —C(=O)—, and —NR$^a$—;

each $R^a$ is independently selected from the group consisting of H and $C_{1-3}$ alkyl;

$Cy^1$ is selected from the group consisting of $C_{6-10}$ aryl and $C_{1-9}$ heteroaryl;

each of which is substituted with n independently selected $R^y$ groups;

$L^1$ is a bond;

$R^1$ is H $C_{1-4}$ alkyl;

$R^1$ is H or $C_{1-4}$ alkyl;

each $R^y$ is independently selected from the group consisting of halogen, cyano, nitro, hydroxyl, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkoxycarbonyl, $C_{1-6}$ alkylcarbonyl, $C_{1-6}$ haloalkylcarbonyl, $C_{6-10}$ arylcarbonyl, $C_{1-6}$ alkylsulfonyl, sulfonamido, $C_{1-6}$ alkylthio, carbamyl, $C_{1-6}$ alkylcarbamoyl, di-$C_{1-6}$ alkylcarbamoyl, $C_{1-6}$ alkylcarbonylamino, $C_{1-6}$ alkylcarbonyl-($C_{1-4}$-allyl)amino, $C_{1-6}$ alkoxycarbonylamino, amino, $C_{1-6}$ alkylamino, di-$C_{1-6}$ alkylamino, $C_{3-7}$ cycloalkyl, $C_{2-6}$ heterocycloalkyl, phenyl, $C_{1-5}$ heteroaryl, $C_{3-7}$ cycloaryl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl; wherein said $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkoxycarbonyl, $C_{1-6}$ alkylcarbonyl, $C_{1-6}$ alkylcarbamoyl, di-$C_{1-6}$ alkyl-carbamyl, $C_{1-6}$ alkylcarbonylamino, $C_{1-6}$ alkylcarbonyl-($C_{1-4}$-alkyl)amino, $C_{1-6}$ alkoxycarbonylamino, $C_{1-6}$ alkylamino, di-$C_{1-6}$ alkylamino are each optionally substituted by 1, 2, or 3 independently selected $R^{y'}$ groups; and wherein said $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl are each optionally substituted by 1, 2, or 3 independently selected $R^{y''}$ groups;

provided that only one $R^y$ is selected from the group consisting of optionally substituted $C_{3-7}$cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl;

each $R^z$ is independently selected from the group consisting of halogen, cyano, nitro, hydroxyl, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{6-10}$ aryloxy, $C_{1-6}$ alkoxycarbonyl, $C_{1-6}$ alkylcarbonyl, carbamyl, $C_{1-6}$ alkylcarbamoyl, di-$C_{1-6}$ alkylcarbamoyl, $C_{1-6}$ alkylcarbonylamino, $C_{1-6}$ alkylcarbonyl-($C_{1-4}$-alkyl)amino, $C_{1-6}$ alkoxycarbonylamino, amino, $C_{1-6}$ alkylamino, di-$C_{1-6}$ alkylamino, $C_{3-7}$ cycloalkyl, $C_{2-6}$ heterocycloalkyl, phenyl, $C_{1-6}$ heteroaryl, $C_{3-7}$ cycloakyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl; wherein said $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkoxycarbonyl, $C_{1-6}$ alkylcarbonyl, $C_{1-6}$ alkylcarbamoyl, di-$C_{1-6}$ alkylcarbamyl, $C_{1-6}$ alkylcarbonylamino, $C_{1-6}$ alkylcarbonyl-($C_{1-4}$-alkyl)amino, $C_{1-6}$ alkoxycarbonylamino, $C_{1-6}$ alkylamino, di-$C_{1-6}$ alkylamino are each optionally substituted by 1, 2, or 3 independently selected $R^{z'}$ groups; and wherein said $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl are each optionally substituted by 1, 2, or 3 independently selected $R^{z''}$ groups;

provided that only one $R^z$ is selected from the group consisting of optionally substituted $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$alkyl, and $C_{1-6}$ heteroaryl-$C_{1-4}$-alkyl;

each $R^{y'}$ and $R^{z'}$ is independently selected from the group consisting of hydroxyl, cyano, nitro, $C_{1-4}$ alkoxy, $C_{1-4}$ haloalkoxy, amino, $C_{1-4}$ alkylamino, and di-($C_{1-4}$-alkylamino;

each $R^{y''}$ and $R^{z''}$ is independently selected from the group consisting of halogen, hydroxyl, cyano, nitro, $C_{1-4}$ alkyl, $C_{1-4}$haloalkyl, $C_{1-4}$ alkoxy, $C_{1-4}$ haloalkoxy, amino, $C_{1-4}$ alkylamino, and di-$C_{1-4}$alkylamino;

n is an integer selected from 0, 1, 2, 3, and 4 when Cy' is $C_{1-9}$ heteroaryl and n is an integer selected from the group consisting of 1, 2, 3, and 4 when $Cy^1$ is $C_{6-10}$aryl; and m is an integer selected from the group consisting of 0, 1, 2, and 3;

provided that the compound is not N-(7-(2 aminophenylamino)-7-oxoheptyl)biphenyl-3-carboxamide; N-(7-(2-aminophenylamino)-7-oxoheptyl)biphenyl-4-carboxamide; or N-(7-(2-aminophenylamino)-7-oxoheptyl)-6-phenylnicotinamide.

In certain embodiments, the selective HDAC3 inhibitor is:

N-(6-(2-aminophenylamino)-6-oxohexyl)-4-methylbenzamide;

N-(2-amino-4-fluorophenyl)-6-(thiazol-2-ylcarbonylamino) hexanamide;

N-(6-(2-amino-4-fluorophenylamino)-6-oxohexyl)-4-methylbenzamide;
N-(6-(2-amino-5-fluorophenylamino)-6-oxohexyl)-4-fluorobenzamide
N-(6-(2-amino-4-fluorophenylamino)-6-oxohexyl)-4-fluorobenzamide;
N-(2-amino-5-fluorophenyl)-6-(thiazol-2-ylcarbonylamino)hexanamide;
N-(6-(2-amino-5-fluorophenylamino)-6-oxohexyl)-4-methylbenzamide;
N-(6-(2-amino-4-fluorophenylamino)-6-oxohexyl)-4-fluoro-N-methylbenzamide;
N-(5-(2-aminophenylamino)-5-oxopentyl)-4-methylbenzamide;
N-(7-(2-aminophenylamino)-7-oxoheptyl)-4-methylbenzamide;
N-(6-(2-amino-4-fluorophenylamino)-6-oxohexyl)benzofuran-2-carboxamide;
N-(6-(2-amino-4-fluorophenylamino)-6-oxohexyl)picolinamide;
N-(6-(2-amino-4-fluorophenylamino)-6-oxohexyl)nicotinamide;
N-(6-(2-amino-5-methoxyphenylamino)-6-oxohexyl)-4-methylbenzamide;
N-(2-(3-(2-aminophenylamino)-3-oxopropoxy)ethyl)-4-methylbenzamide;
N-(6-(2-amino-4-fluoro-5-(piperidin-1-yl)phenylamino)-6-oxohexyl)-4-methylbenzamide;
N-(6-(2-amino-5-phenoxyphenylamino)-6-oxohexyl) nicotinamide;
N-(7-(4-aminobiphenyl-3-ylamino)-7-oxoheptyl)nicotinamide;
N-(7-(2-amino-5-(thiophen-2-yl)phenylamino)-7-oxo-heptyl)nicotinamide;
N-(6-(2-aminophenylamino)-6-oxohexyl)-4-fluorobenzamide;
N-(6-(2-aminophenylamino)-6-oxohexyl)-4-chlorobenzamide;
N-(6-(2-aminophenylamino)-6-oxohexyl)-3,4-dichlorobenzamide;
N-(6-(2-aminophenylamino)-6-oxohexyl)-4-methoxybenzamide;
N-(6-(2-aminophenylamino)-6-oxohexyl)-3-chlorobenzamide;
N-(6-(2-aminophenylamino)-6-oxohexyl)-4-(dimethylamino)benzamide;
N-(6-(2-aminophenylamino)-6-oxohexyl)-4-tert-butylbenzamide;
N-(6-(2-aminophenylamino)-6-oxohexyl)-4-(trifluoromethyl)benzamide;
N-(6-(2-aminophenylamino)-6-oxohexyl)-4-nitrobenzamide;
N-(6-(2-aminophenylamino)-6-oxohexyl)-3-nitrobenzamide;
N-(6-(2-aminophenylamino)-6-oxohexyl)-3-(trifluoromethyl)benzamide;
N-(6-(2-aminophenylamino)-6-oxohexyl)-4-cyanobenzamide;
N-(6-(2-aminophenylamino)-6-oxohexyl)-3,5-dichlorobenzamide;
N-(6-(2-aminophenylamino)-6-oxohexyl)thiophene-2-carboxamide;
N-(6-(2-amino-5-fluoro-4-(piperidin-1-yl)phenylamino)-6-oxohexyl)-4-methylbenzamide;
N-(6-(2-amino-4-hydroxyphenylamino)-6-oxohexyl)-4-methylbenzamide;
N-(6-(2,4-diaminophenylamino)-6-oxohexyl-4-methylbenzamide;
N-(6-(2-amino-4,5-dimethylphenylamino)-6-oxohexyl)-4-methylbenzamide;
N-(6-(2-amino-4-chlorophenylamino)-6-oxohexyl)-4-methylbenzamide;
N-(6-(2-amino-4-fluoro-5-(1H-pyrazol-1-yl)phenylamino)-6-oxohexyl)-4-methylbenzamide;
N-(6-(2-amino-4-bromophenylamino)-6-oxohexyl)-4-methylbenzamide;
N-(6-(4-aminobenzo[d][1,3]dioxol-5-ylamino)-6-oxohexyl)-4-methylbenzamide;
N-(6-(2-amino-4-fluoro-5-morpholinophenylamino)-6-oxohexyl)-4-methylbenzamide;
N-(6-(3-aminonaphthalen-2-ylamino)-6-oxohexyl-4-methylbenzamide;
N-(6-(2-aminophenylamino)-6-oxohexyl)thiazole-2-carboxamide;
N-(6-(2-aminophenylamino)-6-oxohexyl)-4-methylthiazole-2-carboxamide;
N-(6-(2-aminophenylamino)-6-oxohexyl)-5-methylthiazole-2-carboxamide;
N-(2-(3-(2-aminophenylamino)-3-oxopropylamino) ethyl)-4-methylamide;
N-(6-(2-aminophenylamino)-6-oxohexyl)-2,4-dichlorobenzamide;
N-(6-(2-aminophenylamino)-6-oxohexyl)-4-(methasulfonyl)benzamide;
N-(6-(2-aminophenylamino)-6-oxohexyl)-4-sulfamoylbenzamide;
N-(6-(2-aminophenylamino)-6-oxohexyl)isonicotinamide;
N-(6-(2-aminophenylamino)-6-oxohexyl)pyrazine-2-carboxamide;
N-(6-(2-aminophenylamino)-6-oxohexyl)pyridazine-4-carboxamide;
N-(6-(2-aminophenylamino)-6-oxohexyl)furan-2-carboxamide;
N-(6-(2-aminophenylamino)-6-oxohexyl)furan-3-carboxamide;
N-(6-(2-aminophenylamino)-6-oxohexyl)-thiophene-2-carboxamide;
N-(6-(2-aminophenylamino)-6-oxohexyl)thiophene-3-carboxamide;
N-(6-(2-aminophenylamino)-6-oxohexyl)-1H-pyrrole-2-carboxamide;
N-(6-(2-aminophenylamino)-6-oxohexyl)-4H-1,2,4-triazole-3-carboxamide;
N-(6-(2-aminophenylamino)-6-oxohexyl)isoxazole-5-carboxamide;
N-(6-(2-aminophenylamino)-6-oxohexyl)thiazole-4-carboxamide;
N-(6-(2-aminophenylamino)-6-oxohexyl)-2-(piperidin-1-yl)isonicotinamide;
N-(6-(2-aminophenylamino)-6-oxohexyl)-3-phenyl-1H-pyrazole-5-carboxamide;
N-(6-(2-aminophenylamino)-6-oxohexyl)benzofuran-2-carboxamide;
N-(6-(2-aminophenylamino)-6-oxohexyl)benzo[d]thiazole-6-carboxamide;
N-(6-(2-aminophenylamino)-6-oxohexyl)benzo[c][1,2,5]oxadiazole-5-carboxamide;
N-(6-(2-aminophenylamino)-6-oxohexyl)quinoxaline-6-carboxamide;
N-(6-(2-aminophenyl)-6-oxohexyl)quinoline-7-carboxamide;
N-(6-(2-aminophenylamino)-6-oxohexyl)-3-(1H-tetrazol-5-yl)benzamide;

N-(6-(2-aminophenylamino)-6-oxohexyl)-4-(1H-tetrazol-5-yl)benzamide;
N-(6-(2-aminophenylamino)-6-oxohexyl)-5-(thiophen-3-yl)isoxazole-3-carboxamide;
N-(6-(2-aminophenylamino)-6-oxohexyl)-1H-indole-2-carboxamide;
N-(6-(2-aminophenylamino)-6-oxohexyl)-1H-indole-5-carboxamide;
N-(6-(2-aminophenylamino)-6-oxohexyl)-5-methoxy-1H-indole-2-carboxamide;
N-(6-(2-aminophenylamino)-6-oxohexyl)-5-cyclopropylisoxazole-3-carboxamide;
N-(6-(2-aminophenylamino)-6-oxohexyl)-1H-indazole-3-carboxamide;
N-(6-(2-aminophenylamino)-6-oxohexyl)isoquinoline-3-carboxamide;
N-(6-(2-aminophenylamino)-6-oxohexyl)quinoline-3-carboxamide;
N-(6-(2-aminophenylamino)-6-oxohexyl)cinnoline-4-carboxamide;
N-(6-(2-aminophenylamino)-6-oxohexyl)quinoxaline-2-carboxamide;
N-(6-(2-aminophenylamino)-6-oxohexyl)-2-(pyridin-4-yl)thiazole-4-carboxamide;
N-(6-(2-aminophenylamino)-6-oxohexyl)-4-methyl-2-(pyridin-3-yl)thiazole-5-carboxamide;
N-(6-(2-aminophenylamino)-6-oxohexyl)-4-(1H-pyrrol-1-yl)benzamide;
N-(6-(2-aminophenylamino)-6-oxohexyl)-4-methyl-2-(pyridin-2-yl)thiazole-5-carboxamide;
N-(5-(2-aminophenylamino)-5-oxopentyl)-5-methylthiazole-2-carboxamide;
N-(5-(2-aminophenylamino)-5-oxopentyl)-2,6-dimethoxynicotinamide;
N-(5-(2-aminophenylamino)-5-oxopentyl)-4-(methylsulfonyl)benzamide;
N-(5-(2-aminophenylamino)-5-oxopentyl)-5-methoxy-1H-indole-2-carboxamide;
N-(5-(2-aminophenylamino)-5-oxopentyl)benzo[d]thiazole-6-carboxamide;
N-(5-(2-aminophenylamino)-5-oxopentyl)-2-pyridin-4-yl)thiazole-4-carboxamide;
N-(5-(2-aminophenylamino)-5-oxopentyl)-2-(piperidin-1-yl)isonicotinamide;
N-(5-(2-aminophenylamino)-5-oxopentyl)isoxazole-5-carboxamide;
N-(5-(2-aminophenylamino)-5-oxopentyl)-5-phenyl-4H-pyrazole-3-carboxamide;
N-(5-(2-aminophenylamino)-5-oxopentyl)-3-(1-methyl-1H-pyrazol-4-yl)isoxazole-5-carboxamide;
N-(6-(2-aminophenylamino)-6-oxohexyl)-2-methylbenzamide;
N-(6-(2-aminophenylamino)-6-oxohexyl)-3-ethylbenzamide;
N-(6-(2-aminophenylamino)-6-oxohexyl)-4-ethylbenzamide;
N-(6-(2-aminophenylamino)-6-oxohexyl)-3,4-dimethylbenzamide;
N-(6-(2-aminophenylamino)-6-oxohexyl)-4-propylbenzamide;
N-(6-(2-aminophenylamino)-6-oxohexyl)-4-isopropylbenzamide;
N-(6-(2-aminophenylamino)-6-oxohexyl)-4-cyclopropylbenzamide;
N-(6-(2-aminophenylamino)-6-oxohexyl)-4-(hydroxymethyl)benzamide;
N-(6-(2-aminophenylamino)-6-oxohexyl)-2-(dimethylamino)benzamide;
N-(6-(2-aminophenylamino)-6-oxohexyl)-2,4-difluorobenzamide;
N-(6-(2-aminophenylamino)-6-oxohexyl)-3-methyl-1H-indol-2-carboxamide;
N-(6-(2-aminophenylamino)-6-oxohexyl)-4-methoxy-1H-indole-2-carboxamide;
N-(6-(2-aminophenylamino)-6-oxohexyl)-4-ethoxy-1H-indole-2-carboxamide;
N-(6-(2-aminophenylamino)-6-oxohexyl)-4-fluoro-1H-indole-2-carboxamide;
N-(6-(2-aminophenylamino)-6-oxohexyl)-4-chloro-1H-indole-2-carboxamide;
N-(6-(2-aminophenylamino)-6-oxohexyl)-5-(trifluoromethoxy)-1H-indole-2-carboxamide;
N-(6-(2-aminophenylamino)-6-oxohexyl)-5-methyl-1H-indole-2-carboxamide;
N-(6-(2-aminophenylamino)-6-oxohexyl)-5-fluoro-1H-indole-2-carboxamide;
N-(6-(2-aminophenylamino)-6-oxohexyl)-5-chloro-1H-indole-2-carboxamide;
N-(6-(2-aminophenylamino)-6-oxohexyl)-7-methoxy-1H-indole-2-carboxamide;
N-(6-(2-aminophenylamino)-6-oxohexyl)-7-methyl-1H-indole-2-carboxamide;
N-(6-(2-aminophenylamino)-6-oxohexyl)-7-fluoro-1H-indole-2-carboxamide;
N-(6-(2-aminophenylamino)-6-oxohexyl)-6-(dimethylamino)-1H-indole-2-carboxamide;
N-(6-(2-aminophenylamino)-6-oxohexyl)-4-(difluoromethoxy)-1H-indole-2-carboxamide;
N-(6-(2-aminophenylamino)-6-oxohexyl)-1-methyl-1H-indole-2-carboxamide;
N-(6-(2-aminophenylamino)-6-oxohexyl)-5-methoxy-1-methyl-1H-indole-2-carboxamide;
N-(6-(2-aminophenylamino)-6-oxohexyl)-5-fluoro-1-methyl-1H-indole-2-carboxamide;
N-(6-(2-aminophenylamino)-6-oxohexyl)-5-chloro-1-methyl-1H-indole-2-carboxamide;
N-(6-(2-aminophenylamino)-6-oxohexyl)-1,5-dimethyl-1H-indole-2-carboxamide;
N-(6-(2-aminophenylamino)-6-oxohexyl)-1-(2-methoxyethyl)-1H-indole-2-carboxamide;
N-(6-(2-aminophenylamino)-6-oxohexyl)-2-ethylbenzamide;
N-(6-(2-aminophenylamino)-6-oxohexyl)-3-(dimethylamino)benzamide;
N-(6-(2-aminophenylamino)-6-oxohexyl)-7-methoxy-1H-indole-3-carboxamide;
N-(6-(2-aminophenylamino)-6-oxohexyl)-1-methyl-1H-indole-6-carboxamide;
N-(6-(2-aminophenylamino)-6-oxohexyl)-2,3-dimethyl-1H-indole-7-carboxamide;
N-(6-(2-aminophenylamino)-6-oxohexyl)-3-(trifluoromethoxy)benzamide;
N-(6-(2-aminophenylamino)-6-oxohexyl)-4-(trifluoromethoxy)benzamide;
N-(6-(2-aminophenylamino)-6-oxohexyl)-1-methyl-1H-indole-3-carboxamide;
N-(6-(2-aminophenylamino)-6-oxohexyl)-5-ethoxy-1H-indole-2-carboxamide;
N-(6-(2-aminophenylamino)-6-oxohexyl)-4-(ethylamino)benzamide;
N-(6-(2-aminophenylamino)-6-oxohexyl)-2,3-dimethyl-1H-indole-5-carboxamide;

N-(6-(2-aminophenylamino)-6-oxohexyl)-7-chloro-1H-indole-3-carboxamide;
N-(6-(2-aminophenylamino)-6-oxohexyl)-3-methylbenzamide;
N-(6-(2-aminophenylamino)-6-oxohexyl)-2,4-dimethylbenzamide;
N-(6-(2-aminophenylamino)-6-oxohexyl)-4-(difluoroethyl)benzamide;
N-(6-(2-aminophenylamino)-6-oxohexyl)-4-(2-hydroxypropan-2-yl)benzamide;
N-(6-(2-aminophenylamino)-6-oxohexyl)-4-(azetidin-1-yl)benzamide;
N-(6-(2-aminophenylamino)-6-oxohexyl)-3-(4-methylpiperazin-1-yl)benzamide;
N-(6-(2-aminophenylamino)-6-oxohexyl)-2-(4-methylpiperazin-1-yl)benzamide;
N-(6-(2-aminophenylamino)-6-oxohexyl)-4-morpholinobenzamide;
N-(6-(2-aminophenylamino)-6-oxohexyl)-2-chlorobenzamide;
N-(6-(2-aminophenylamino)-6-oxohexyl)-3,4-difluorobenzamide;
N-(6-(2-aminophenylamino)-6-oxohexyl)-1H-indole-3-carboxamide;
N-(6-(2-aminophenylamino)-6-oxohexyl)-5-methoxy-1H-indole-3-carboxamide;
N-(6-(2-aminophenylamino)-6-oxohexyl)-2-cyclohexylbenzamide;
N-(6-(2-aminophenylamino)-6-oxohexyl)-2-(methoxyethyl)benzamide;
N-(6-(2-aminophenylamino)-6-oxohexyl)-6-methoxy-1H-indole-3-carboxamide;
N-(6-(2-aminophenylamino)-6-oxohexyl)-1H-indole-4-carboxamide;
N-(6-(2-aminophenylamino)-6-oxohexyl)-1-methyl-1H-indole-4-carboxamide;
N-(6-(2-aminophenylamino)-6-oxohexyl)-1H-indole-5-carboxamide;
N-(6-(2-aminophenylamino)-6-oxohexyl)-1-methyl-1H-indole-5-carboxamide;
N-(6-(2-aminophenylamino)-6-oxohexyl)-1-methyl-1H-indazole-3-carboxamide;
N-(6-(2-aminophenylamino)-6-oxohexyl)-1H-indazole-7-carboxamide;
2-allyl-N-(6-(2-aminophenylamino)-6-oxohexyl)benzamide;
N-(6-(2-aminophenylamino)-6-oxohexyl)-2-(2,2,2-trifluoroacetyl)benzamide;
N-(6-(2-aminophenylamino)-6-oxohexyl)-2-ethoxybenzamide;
N-(6-(2-aminophenylamino)-6-oxohexyl)-2-propoxybenzamide;
N-(6-(2-aminophenylamino)-6-oxohexyl)-2-(ethylthio)benzamide;
N-(6-(2-aminophenylamino)-6-oxohexyl)-2-(methylsulfonyl)benzamide;
N-(6-(2-aminophenylamino)-6-oxohexyl)-2-cyanobenzamide;
2-acetyl-N-(6-(2-aminophenylamino)-6-oxohexyl)benzamide;
N-(6-(2-aminophenylamino)-6-oxohexyl)-2-benzoylbenzamide;
N-(6-(2-aminophenylamino)-6-oxohexyl)biphenyl-2-carboxamide;
N-(6-(2-aminophenylamino)-6-oxohexyl)-2-(difluoromethoxy)benzamide;
N-(6-(2-aminophenylamino)-6-oxohexyl)-2-(2-methoxyethoxyl)benzamide;
N-(6-(2-aminophenylamino)-6-oxohexyl)-2-(trifluoromethyl)benzamide;
N-(6-(2-aminophenylamino)-6-oxohexyl)-2-fluorobenzamide;
N-(6-(2-aminophenylamino)-6-oxohexyl)-2-methoxybenzamide;
N-(6-(2-aminophenylamino)-6-oxohexyl)-2-bromobenzamide;
N-(6-(2-aminophenylamino)-6-oxohexyl)-4-methoxy-1H-indole-3-carboxamide;
N-(6-(2-aminophenylamino)-6-oxohexyl)-1H-indole-7-carboxamide;
N-(6-(2-aminophenylamino)-6-oxohexyl)-1H-indazole-6-carboxamide;
N-(6-(2-aminophenylamino)-6-oxohexyl)-6-methoxy-1H-indole-2-carboxamide;
N-(6-(2-aminophenylamino)-6-oxohexyl)-4-(methylamino)benzamide;
N-(6-(2-aminophenylamino)-6-oxohexyl)-4-(cyclopropylamino)benzamide;
N-(6-(2-aminophenylamino)-6-oxohexyl)-4-(4-methylpiperazin-1-yl)benzamide;
N-(6-(2-aminophenylamino)-6-oxohexyl)-6-methyl-1H-indole-2-carboxamide;
N-(6-(2-aminophenylamino)-6-oxohexyl)-5-ethoxy-1-methyl-1H-indole-2-carboxamide;
N-(6-(2-aminophenylamino)-6-oxohexyl)-2,3-dimethyl-1H-indole-6-carboxamide;
N-(6-(2-aminophenylamino)-6-oxohexyl)-5-methyl-1H-indazole-3-carboxamide;
N-(6-(2-aminophenylamino)-6-oxohexyl)-5-chloro-1H-indole-3-carboxamide;
N-(6-(2-aminophenylamino)-6-oxohexyl)-1H-6-carboxamide;
(E)-N-(6-(2-aminophenylamino)-6-oxohex-3-enyl)-4-methylbenzamide;
(E)-N-(6-(2-aminophenylamino)-6-oxohex-3-enyl)-4-methoxybenzamide;
(E)-N-(6-(2-aminophenylamino)-6-oxohex-3-enyl)-4-fluorobenzamide;
(E)-N-(6-(2-aminophenylamino)-6-oxohex-3-enyl)-3-chlorobenzamide;
(E)-N-(6-(2-aminophenylamino)-6-oxohex-4-enyl)-4-morpholinobenzamide;
(E)-N-(6-(2-aminophenylamino)-6-oxohex-4-enyl)-4-(dimethylamino)benzamide;
(E)-N-(6-(2-aminophenylamino)-6-oxohex-4-enyl)-4-methoxybenzamide;
(E)-N-(6-(2-aminophenylamino)-6-oxohex-4-enyl)-3-chlorobenzamide;
(E)-N-(6-(2-aminophenylamino)-6-oxohex-4-enyl)-4-fluorobenzamide;
(E)-N-(6-(2-aminophenylamino)-6-oxohex-4-enyl)-4-methylbenzamide;
N-(6-(2-aminophenylamino)-6-oxohexyl)-3-difluoromethoxy)benzamide;
N-(6-(2-aminophenylamino)-6-oxohexyl)-3-cyanobenzamide;
N-(6-(2-aminophenylamino)-6-oxohexyl)-3-morpholinobenzamide;
N-(6-(2-aminophenylamino)-6-oxohexyl)-3-ethoxybenzamide; or
N-(6-(2-aminophenylamino)-6-oxohexyl)-3-nitrobenzamide;

or a pharmaceutically acceptable salt, hydrate, solvate, or prodrug thereof.

In certain embodiments, the selective HDAC3 inhibitor is:

N-(2-amino-4-fluorophenyl)-6-(thiazol-2-ylcarbonylamino) hexanamide;

N-(6-(2-amino-4-fluorophenylamino)-6-oxohexyl)-4-methylbenzamide;

N-(6-(2-amino-4-fluorophenylamino)-6-oxohexyl)-4-fluorobenzamide;

N-(6-(2-amino-4-fluorophenylamino)-6-oxohexyl)-4-fluoro-N-methylbenzamide;

N-(6-(2-amino-4-fluorophenylamino)-6-oxohexyl)benzofuran-2-carboxamide;

N-(6-(2-amino-4-fluorophenylamino)-6-oxohexyl)picolinamide;

N-(6-(2-amino-4-fluorophenylamino)-6-oxohexyl)nicotinamide;

N-(6-(2-amino-4-fluoro-5-(piperidin-1-yl)phenylamino)-6-oxohexyl)-4-methylbenzamide;

N-(6-(2-amino-4-fluoro-5-(1H-pyrazol-1-yl)phenylamino)-6-oxohexyl)-4-methylbenzamide; or N-(6-(2-amino-4-fluoro-5-morpholinophenylamino)-6-oxohexyl)-4-methylbenzamide or a pharmaceutically acceptable salt, hydrate, solvate, or prodrug thereof.

Compounds of Formula (V)

In certain embodiments, the selective HDAC3 inhibitor is a compound of the formula:

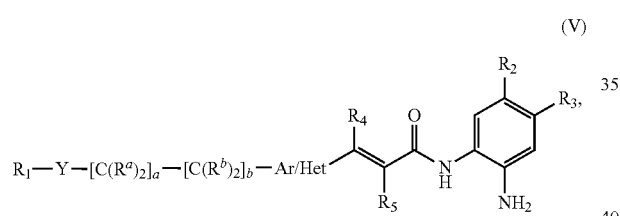

(V)

wherein

Ar/Het is selected from the group consisting of pyrazolyl, thiazolyl, oxazolyl, imidazolyl, thienyl, furanyl, isoxazolyl, isothiazolyl, thiadiazolyl, oxadiazolyl, and 1,2,4-triazolyl;

Y is bond, $CR^c=CR^d$, O, NR', or $S(O)_m$;

a is 1-3;

b is 0-3;

m is 0-2;

each occurrence of $R^a$ and $R^b$ is independently selected from H, F, OH, $C_1$-$C_6$ alkyl, $C_3$-$C_6$ cycloalkyl, $NH_2$, OCO—($C_1$-$C_6$ alkyl), OCO—($C_3$-$C_6$ cycloalkyl), C1-C6 alkoxy, C1-C6 fluoroalkoxy, and cyano;

each of $R^c$ and $R^d$ is, independently, selected from H, F, OH, $C_1$-$C_6$ alkyl, $C_3$-$C_5$ cycloalkyl, $NH_2$, OCO—(C1-C6 alkyl), OCO—($C_3$-$C_5$ cycloalkyl), C1-C6 alkoxy, C1-C6 fluoroalkoxy, and cyano;

each occurrence of $R^e$ is independently selected from H, C1-C6 alkyl, —C(=O)H, —C(=O)$R^h$, C(=O)O(C1-C6 alkyl), C(=O)N($R^i$)$_2$, $SO_2$—$R^h$, wherein $R^h$ is selected from C1-C6 alkyl, $CH_2$-(heteroaryl having 5-10 ring atoms), $CH_2$—(C6-C10 aryl), and C6-C10 aryl; and each occurrence of $R^i$ is independently selected from H, C1-C6 alkyl, $CH_2$-(heteroaryl having 5-10 ring atoms), $CH_2$—(C6-C10 aryl), and C6-C10 aryl and the aryl or heteroaryl portion in $R^h$ and $R^i$ can be optionally substituted with one or more independently selected substituents selected from the group consisting of F, C1-C6 alkyl, fluoro C1-C6 alkyl, C3-C6 cycloalkyl, C1-C6 alkoxy, C1-C6 fluoroalkoxy, and cyano;

each of $R^4$ and $R^5$ is, independently, selected from H, C1-C6 alkyl and F;

R1 is:

(i) hydrogen; or (ii) C6-C10 aryl, which is optionally substituted with from 1-3 $R^o$; or (iii) monocyclic or bicyclic heteroaryl having from 5-10 ring atoms, which is optionally substituted with from 1-3 $R^o$; wherein from 1-4 of the ring atoms is/are a heteroatom independently selected from O, N, N—H, N—$R^o$, and S; or (iv) heterocyclyl having from 4-10 ring atoms, which is optionally substituted with from 1-3 $R^o$; wherein from 1-4 of the ring atoms is/are a heteroatom independently selected from O, N, N—H, N—$R^o$, and S; and each occurrence of $R^o$ is independently selected from the group consisting of: halogen; C1-C6 alkyl; fluoro(C1-C6alkyl); hydroxyl; hydroxy(C1-C4alkyl); C1-C6 alkoxy; fluoro(C1-C6alkoxy); (C1-C6 alkyl)C(O)—; (C1-C6 alkyl)NH—; (C1-C6 alkyl)$_2$N—; formyl; formyl(C1-C4alkyl); cyano; cyano(C1-C4alkyl); benzyl; benzyloxy; $SO_2$—(C1-C6alkyl); SO—(C1-C6alkyl); and nitro;

R2 is selected from H, F, Cl, $CF_3$, $CF_2CF_3$, $CH_2CF_3$, $OCF_3$, $OCHF_2$, phenyl; phenyl substituted with from 1-3 substituents independently selected from F, OH, C1-C6 alkyl, fluoro(C1-C6 alkyl) C3-C6 cycloalkyl, $NH_2$, C1-C6 alkoxy, C1-C6 fluoroalkoxy, and cyano; thienyl; thiazolyl; and pyrazol-1-yl; and R3 is F;

or a pharmaceutically acceptable salt, hydrate, solvate, or prodrug thereof.

In certain embodiments, R2 is H. In certain embodiments, R2 is F. In certain embodiments, R2 is Cl. In certain embodiments, R2 is $CF_3$, $CF_2CF_3$, $CH_2CF_3$, $OCF_3$, or $OCHF_2$.

In certain embodiments, the selective HDAC3 inhibitor is a compound of the formula:

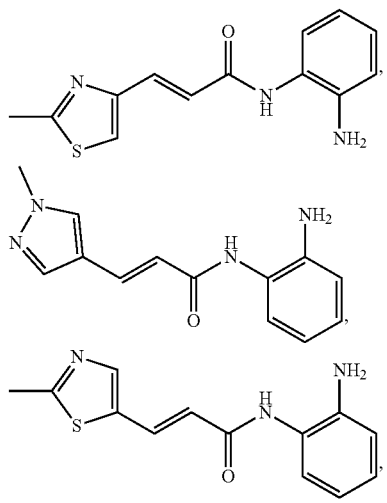

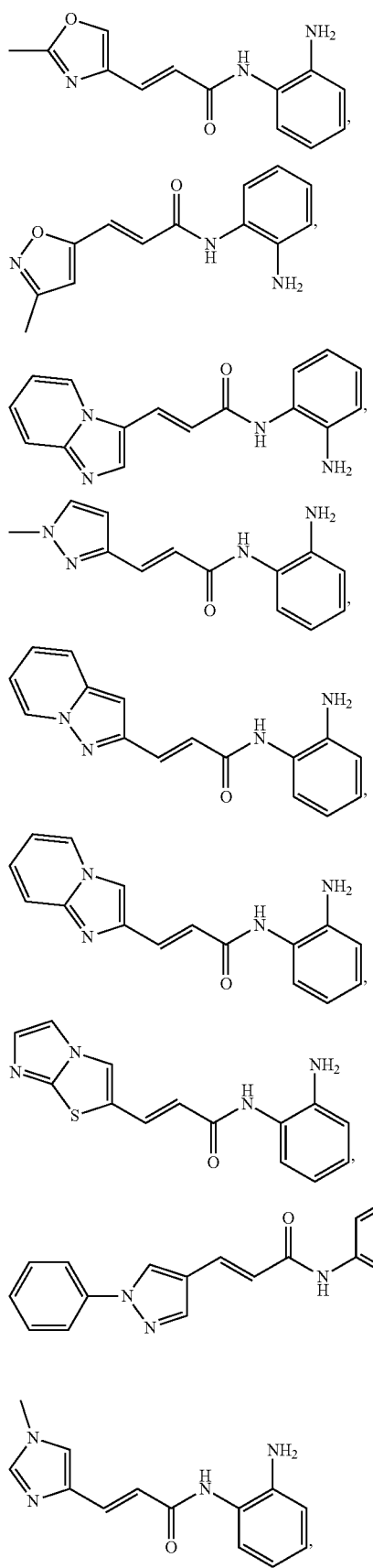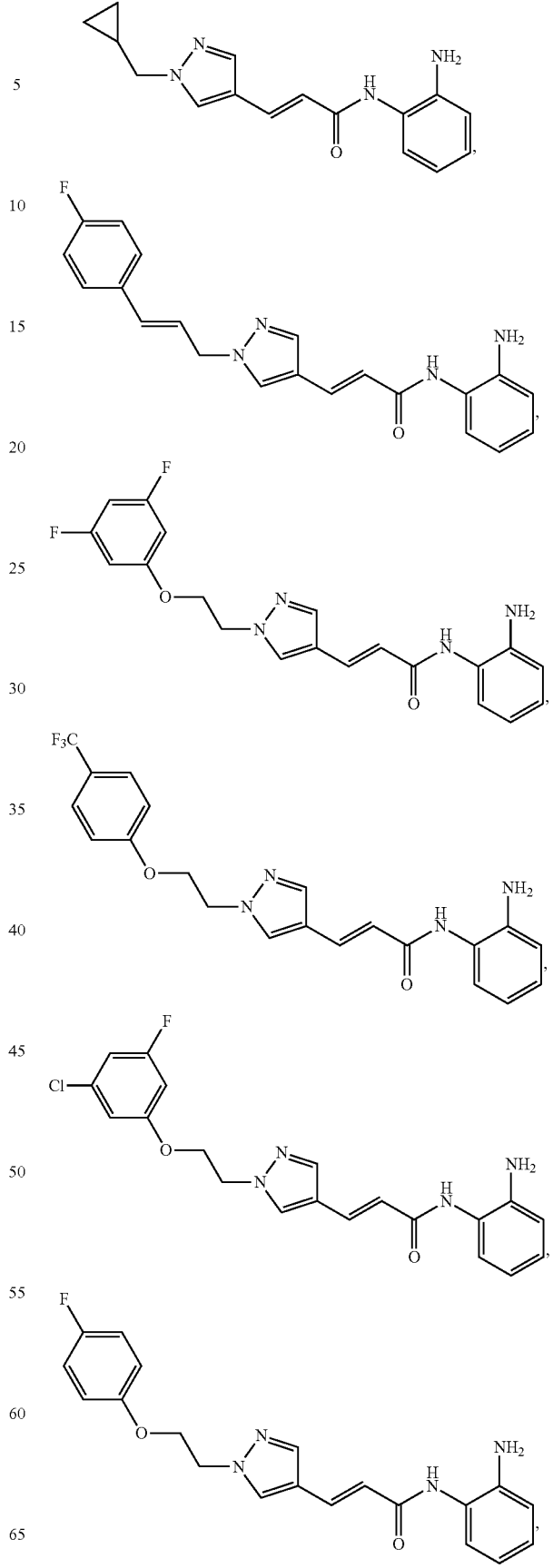

-continued
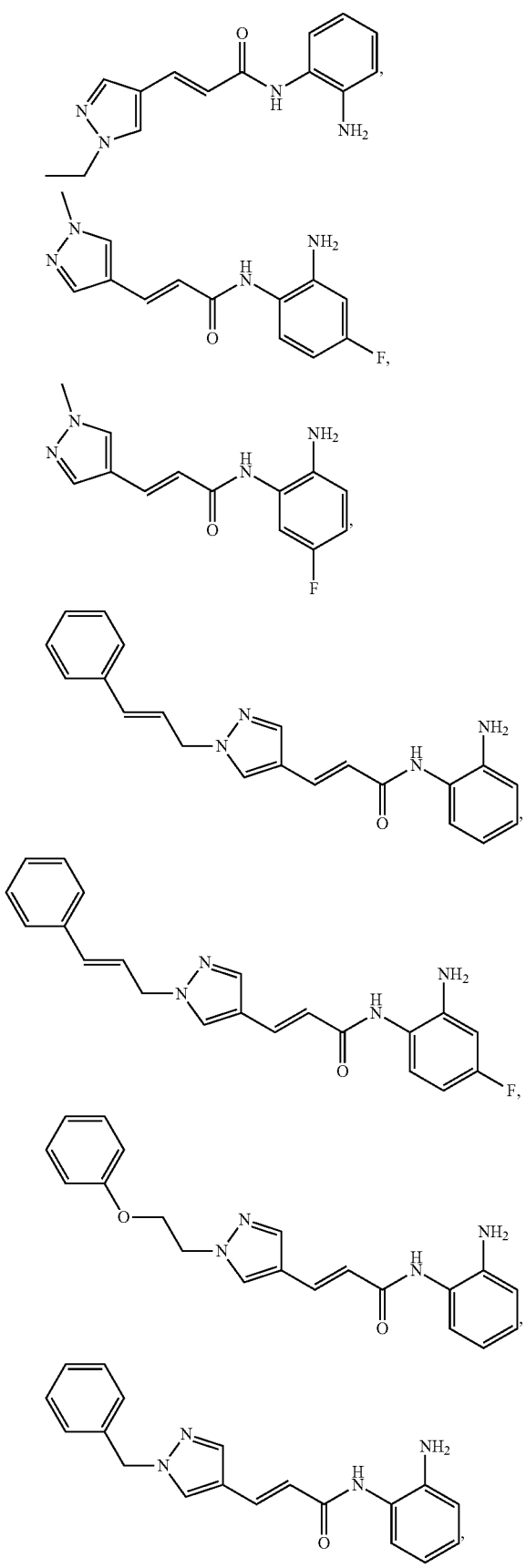
-continued
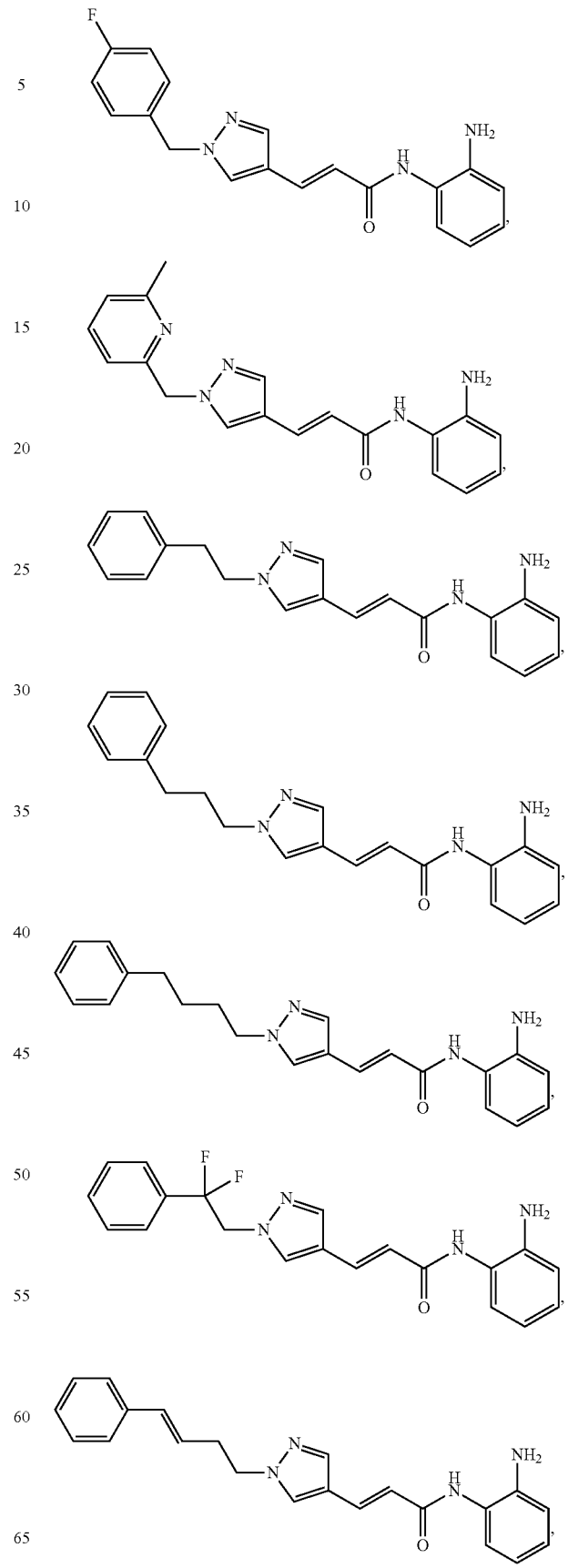

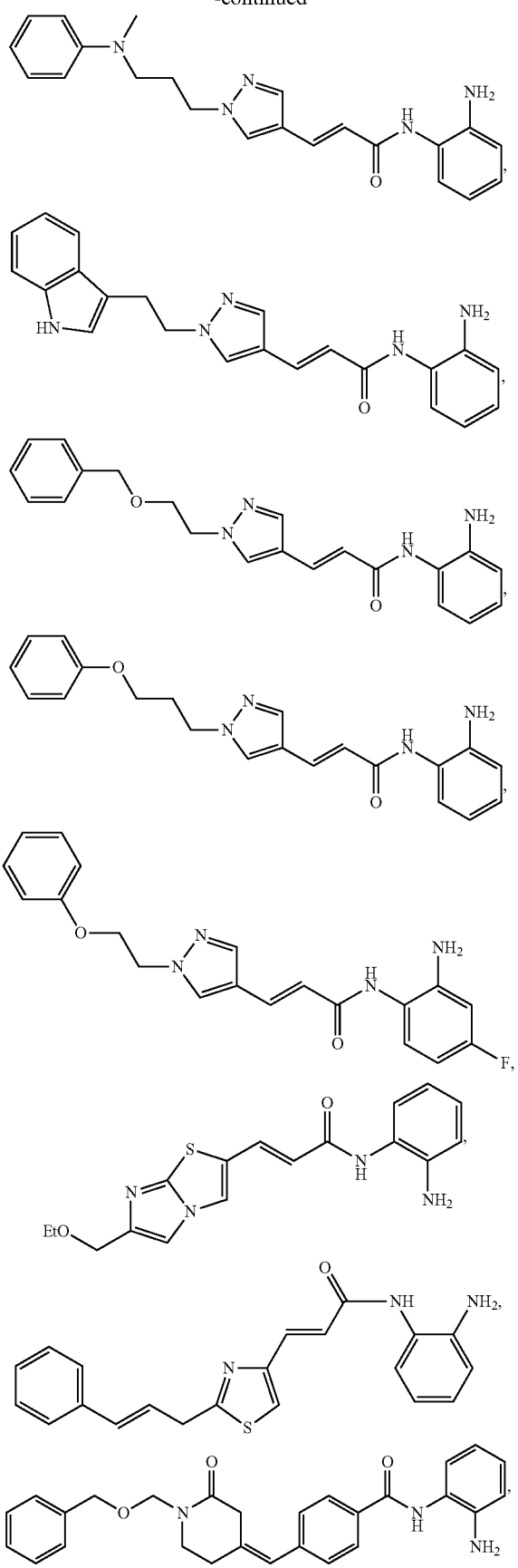
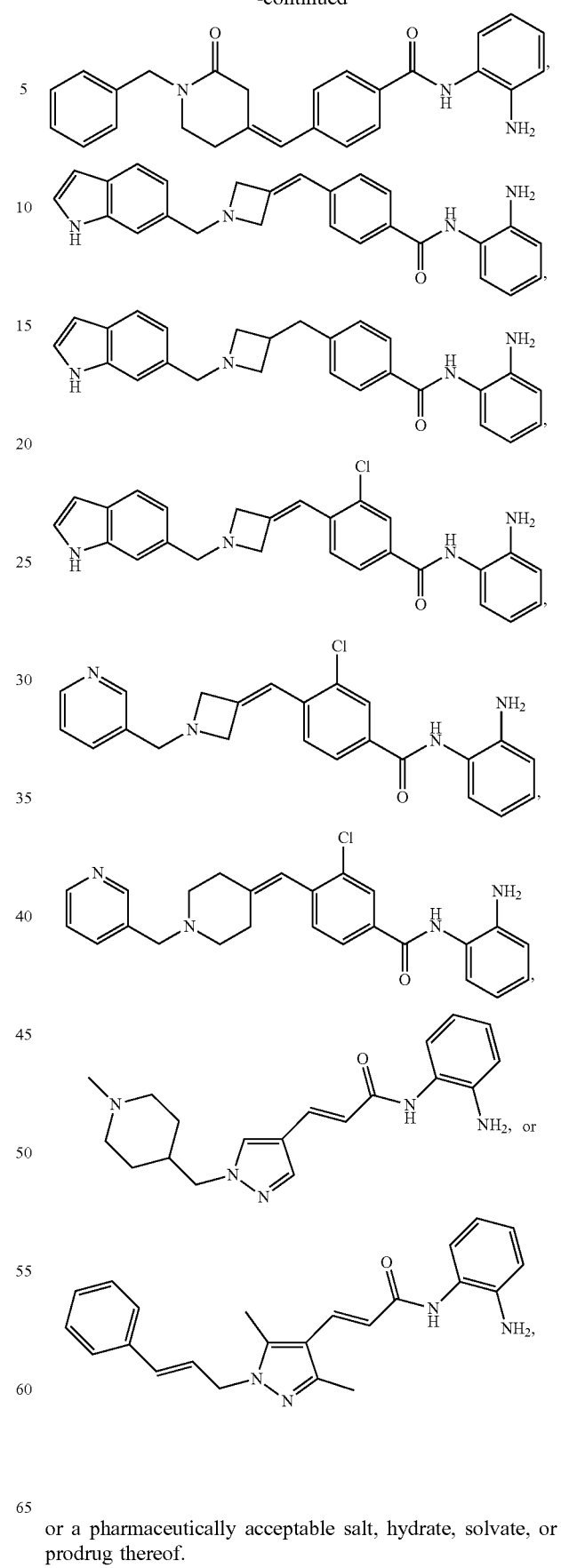
or a pharmaceutically acceptable salt, hydrate, solvate, or prodrug thereof.

In certain embodiments, the selective HDAC3 inhibitor is a compound of the formula:

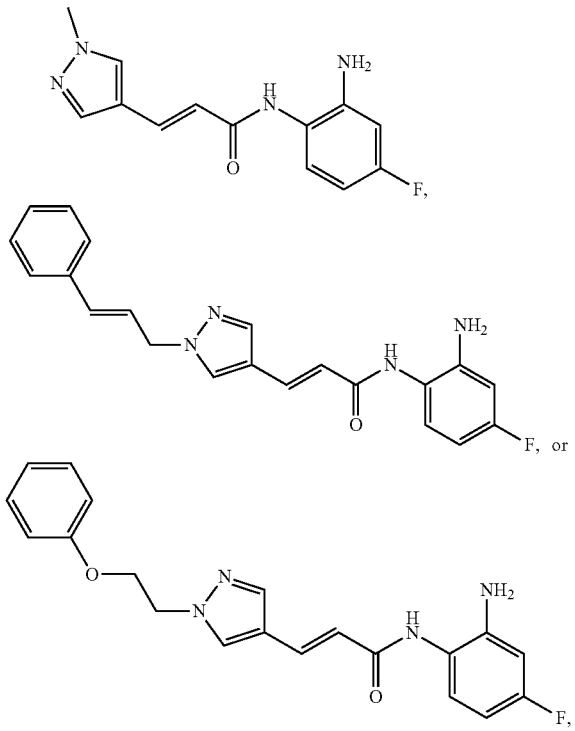

or a pharmaceutically acceptable salt, hydrate, solvate, or prodrug thereof.

In certain embodiments, the selective HDAC3 inhibitor is a compound of the formula:

(RGFP966)

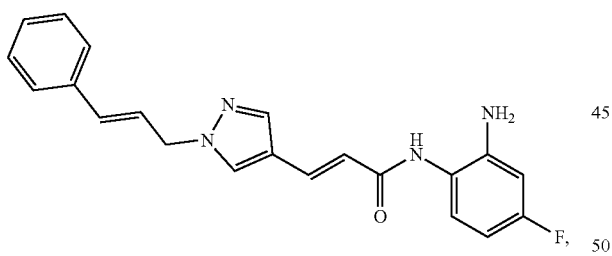

or a pharmaceutically acceptable salt, hydrate, solvate, or prodrug thereof.

Compounds of Formula (VI)

In certain embodiments, the selective HDAC3 inhibitor is a compound of the formula:

(VI)

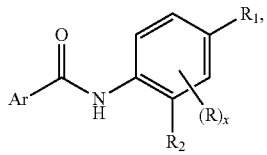

or a pharmaceutically acceptable salt, hydrate, solvate, or prodrug thereof, wherein:

Ar is unsubstituted or substituted phenyl, unsubstituted or substituted pyrazinyl, unsubstituted or substituted pyrimidinyl, unsubstituted or substituted pyridinyl, unsubstituted or substituted quinolinyl, unsubstituted or substituted isoquinolinyl, unsubstituted or substituted quinazolinyl, or unsubstituted or substituted quinoxalinyl;

$R_1$ and $R_2$ are each independently H, hydroxyl, cyano, halogen, unsubstituted or substituted amino, unsubstituted or substituted, $C_1$-$C_6$ alkyl, or unsubstituted or substituted, $C_1$-$C_6$ alkoxy;

each R is independently hydroxyl, cyano, halogen, unsubstituted or substituted amino, unsubstituted or substituted, $C_1$-$C_6$ alkyl, unsubstituted or substituted, $C_1$-$C_6$ alkoxy, or unsubstituted or substituted, $C_6$-$C_{10}$ aryl; and x is 0, 1, 2, or 3;

provided that when Ar is unsubstituted pyrazinyl, x is not 0.

In certain embodiments, $R_1$ is F. In certain embodiments, $R_2$ is $NH_2$. In certain embodiments, x is 0. In certain embodiments, Ar is unsubstituted pyridinyl (e.g., unsubstituted 3-pyridinyl). In certain embodiments, Ar is substituted pyridinyl (e.g., substituted 3-pyridinyl).

In certain embodiments, the selective HDAC3 inhibitor is a compound of the formula:

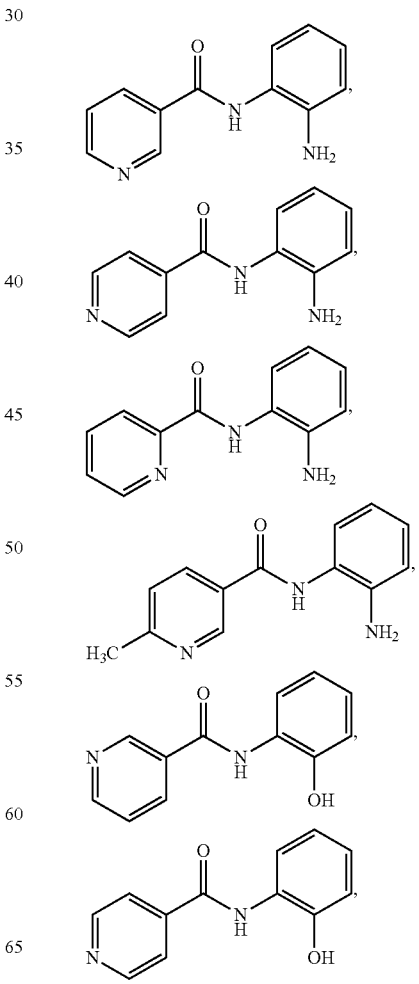

-continued

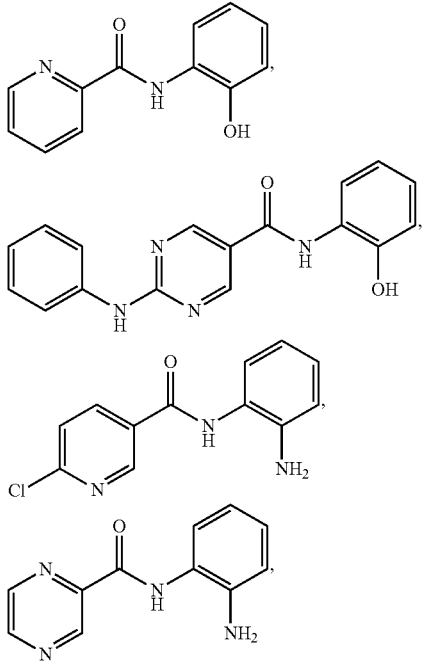

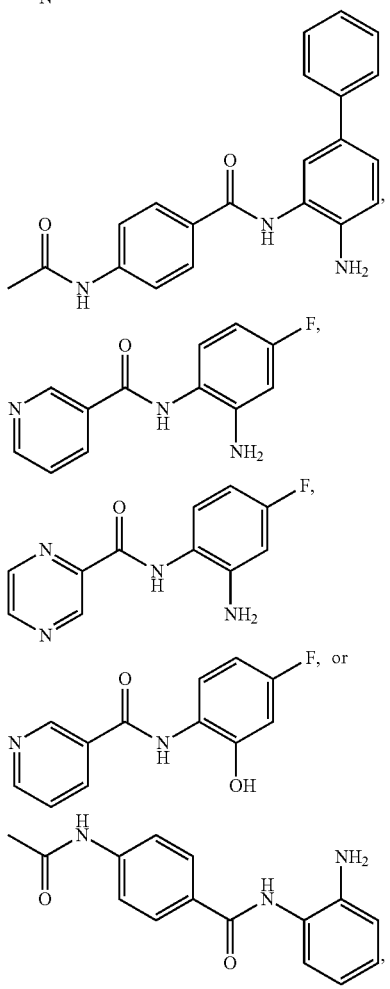

or a pharmaceutically acceptable salt, hydrate, solvate, or prodrug thereof.

In certain embodiments, the selective HDAC3 inhibitor is a compound of the formula:

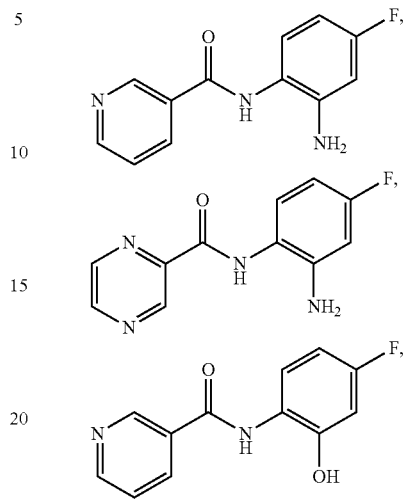

or a pharmaceutically acceptable salt, hydrate, solvate, or prodrug thereof.

Additional Compounds

In certain embodiments, the selective HDAC3 inhibitor is a compound of the formula:

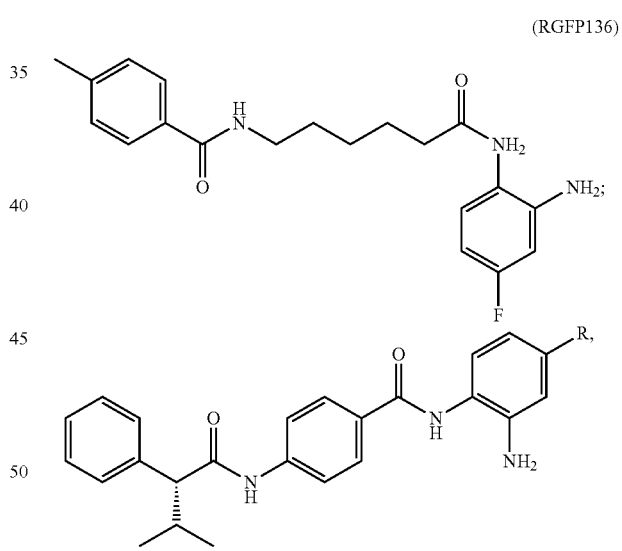

wherein R is H or F;

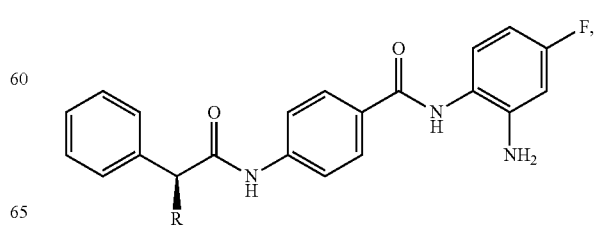

wherein R is Et or Me;

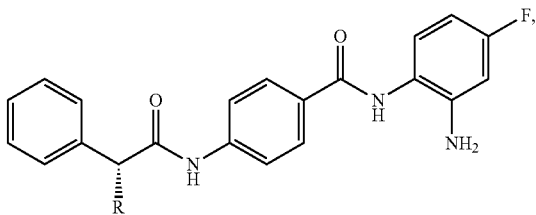

wherein R is Et or Me;

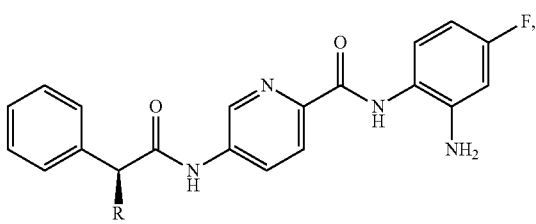

wherein R is i-Pr, Et, or Me;

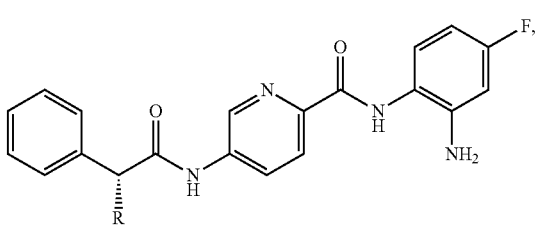

wherein R is i-Pr, Et, or Me;

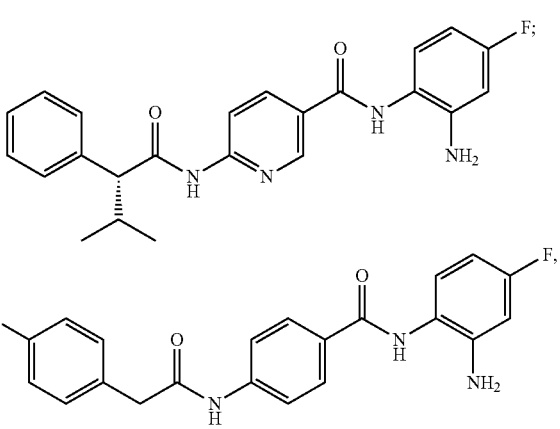

wherein R is H, F, or CF₃;

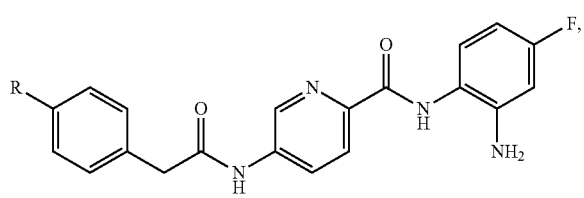

wherein R is H or F;

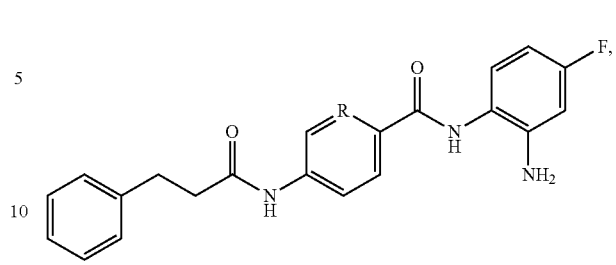

wherein R is CH;

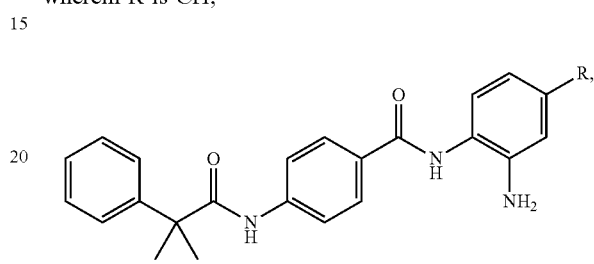

wherein R is F;

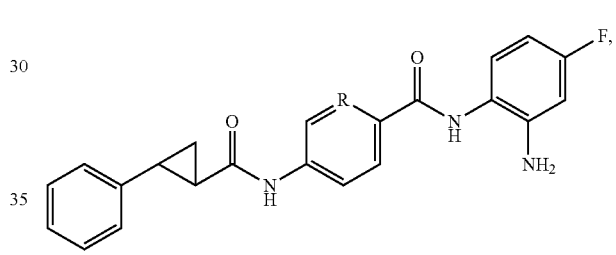

wherein R is CH or N; or

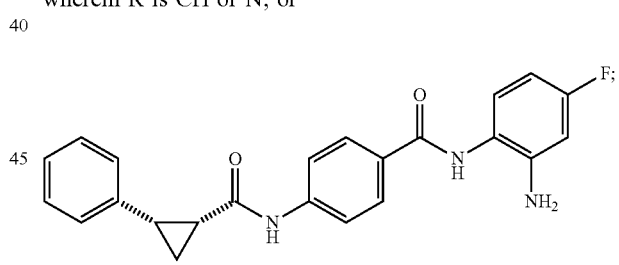

or a pharmaceutically acceptable salt, hydrate, solvate, or prodrug thereof.

The selective HDAC3 inhibitor is more (e.g., at least 1-fold, at least 2-fold, at least 3-fold, at least 4-fold, at least 5-fold, at least 7-fold, at least 10-fold, at least 15-fold, or at least 20-fold, more) active for inhibiting HDAC3 than for inhibiting a histone deacetylase that is not HDAC3. In certain embodiments, the selective HDAC3 inhibitor is more active in an in vitro enzymatic inhibition assay for inhibiting HDAC3 than for inhibiting a histone deacetylase that is not HDAC3. In certain embodiments, the selective HDAC3 inhibitor is at least 5-fold more active for inhibiting HDAC3 than for inhibiting a histone deacetylase that is not HDAC3. In certain embodiments, the selective HDAC3 inhibitor is at least 5-fold more active in an in vitro enzymatic inhibition assay for inhibiting HDAC3 than for inhibiting a histone deacetylase that is not HDAC3. In certain embodiments, the histone deacetylase that is not HDAC3 is HDAC1. In certain embodiments, the histone deacetylase that is not HDAC3 is HDAC2. In certain embodiments, the histone deacetylase that is not HDAC3 is HDAC4, HDAC5, HDAC6, HDAC7, HDAC8, HDAC9, HDAC10, or HDAC11.

In certain embodiments, the amount of the selective HDAC3 inhibitor is effective for increasing (e.g., by at least 10%, at least 30%, at least 100%, at least 3-fold, at least 10-fold, at least 30-fold, or at least 100-fold) expression of an MHC class II protein in at least one of the cancer cells in vitro.

In certain embodiments, the selective HDAC3 inhibitor is administered to the subject in need thereof orally.

Immunotherapy Agents

In some aspects, the disclosure relates to immunotherapy agents and their use in the compositions, kits, and methods described herein, such as to treat cancer. In some embodiments, the immunotherapy agent is effective for increasing (e.g., by at least 10%, at least 30%, at least 100%, at least 3-fold, at least 10-fold, at least 30-fold, or at least 100-fold) an immune response to an MHC class II antigen, e.g., in a subject in need thereof. In some embodiments, MHC Class II molecules contribute to activation of the immune system of a subject through activation of CD4+ T cells by presentation of MHC Class II antigens to the CD4+ T cells. In some embodiments, the immunotherapy agent increases (e.g., by at least 10%, at least 30%, at least 100%, at least 3-fold, at least 10-fold, at least 30-fold, or at least 100-fold) recruitment of immune cells to a cancer, e.g., macrophages and/or T cells, or prevents recruited immune cells, e.g., CD8+ T cells, from becoming inactivated or tolerized. In certain embodiments, the combined amount (combined amount of the selective HDAC3 inhibitor and the immunotherapy agent) increases (e.g., by at least 10%, at least 30%, at least 100%, at least 3-fold, at least 10-fold, at least 30-fold, or at least 100-fold) recruitment of immune cells to a cancer, e.g., macrophages and/or T cells, or prevents recruited immune cells, e.g., CD8+ T cells, from becoming inactivated or tolerized. Recruitment of immune cells can be measured, e.g., by biopsy of a tumor and assessing the presence of immune cell surface markers CD8, CD3 and/or CD4. Activation of immune cells can be measured, e.g., by measuring production of cytokines in the immune cells (e.g., T cells), such as by measuring secretion of interferon-gamma upon challenge of the immune cells with an antigen. In certain embodiments, the combined amount (combined amount of the selective HDAC3 inhibitor and the immunotherapy agent) increases (e.g., by at least 10%, at least 30%, at least 100%, at least 3-fold, at least 10-fold, at least 30-fold, or at least 100-fold) activation of the immune system in the subject in need thereof. The immunotherapy agent may be, e.g., a protein (e.g., an antibody), a small molecule, a peptide, an antisense oligonucleotide, or an siRNA. As described herein, in some embodiments, selective HDAC3 inhibitors can be used in combination with an immunotherapy agent, e.g., in a composition, kit, or method as described herein. In some embodiments, the immunotherapy agent is an immune checkpoint inhibitor.

Immune Checkpoint Inhibitors

In some aspects, the disclosure relates to immune checkpoint inhibitors and their use in the compositions, kits, and methods described herein, such as to treat cancer. Immune checkpoint molecules are molecules that are responsible for modulating immune responses, e.g., modulating T cell responses. Immune checkpoint molecules are important for maintaining immune homeostasis, both by maintaining self-tolerance and protecting a host from pathogens. However, some cancers benefit from immune checkpoint molecules that hinder the immune system from otherwise attacking the cancer. Accordingly, immune checkpoint inhibitors have been used to restore the immune system's ability to attack certain cancers. As described herein, in some embodiments, selective HDAC3 inhibitors can be used in combination with an immune checkpoint inhibitor as described herein, e.g., in a composition, kit or method as described herein. In some embodiments, the immune checkpoint inhibitor increases (e.g., by at least 10%, at least 30%, at least 100%, at least 3-fold, at least 10-fold, at least 30-fold, or at least 100-fold) recruitment of immune cells to a cancer, e.g., macrophages and/or T cells, or prevents recruited immune cells, e.g., CD8+ T cells, from becoming inactivated or tolerized. In some embodiments, the combined amount (combined amount of the selective HDAC3 inhibitor and immune checkpoint inhibitor) increases (e.g., by at least 10%, at least 30%, at least 100%, at least 3-fold, at least 10-fold, at least 30-fold, or at least 100-fold) recruitment of immune cells to a cancer, e.g., macrophages and/or T cells, or prevents recruited immune cells, e.g., CD8+ T cells, from becoming inactivated or tolerized.

An immune checkpoint inhibitor, as used herein, is an agent that inhibits or prevents the activity of an immune checkpoint molecule, e.g., by binding to the molecule. An immune checkpoint inhibitor may reduce the immune checkpoint molecule activity in a cell or organism, e.g., by at least 5%, at least 10%, at least 20%, at least 30%, at least 40%, at least 50%, at least 60%, at least 70%, at least 80%, at least 90%, or about 100%, compared to a cell or organism that has not been exposed to the immune checkpoint inhibitor. Immune checkpoint molecule activity may be interfered with by antibodies that bind selectively to and block the activity of the immune checkpoint molecule. The activity of the immune checkpoint molecule can also be inhibited or blocked by molecules other than antibodies, such as proteins, small molecules, and peptides, that bind to the immune checkpoint molecule. Agents that bind to and degrade or inhibit the DNA or mRNA encoding the immune checkpoint molecule also can act an immune checkpoint inhibitor. Examples include siRNAs and antisense oligonucleotides. Non-limiting example immune checkpoint molecules include programmed cell death 1 protein (PD-1), programmed cell death 1 protein ligand 1 (PD-L1), cytotoxic T-lymphocyte-associated protein 4 (CTLA-4), T-cell immunoglobulin domain and mucin domain 3 (TIM3), lymphocyte activation gene-3 (LAG3), V-set domain-containing T-cell activation inhibitor 1 (VTCN1 or B7-H4), cluster of differentiation 276 (CD276 or B7-H3), B and T lymphocyte attenuator (BTLA), galectin-9 (GALS), checkpoint kinase 1 (Chk1), adenosine A2A receptor (A2AR), indoleamine 2,3-dioxygenase (IDO), killer-cell immunoglobulin-like receptor (KIR), and V-domain Ig suppressor of T cell activation (VISTA).

In some embodiments, the immune checkpoint inhibitor is an antibody, such a humanized or human antibody. As used herein, the term "antibody" refers to an immunoglobulin molecule that specifically binds to a particular antigen such as an immune checkpoint molecule (e.g., PD-L1, PD-1, or CTLA-4) and includes polyclonal, monoclonal, genetically engineered and otherwise modified forms of antibodies, including but not limited to chimeric antibodies, humanized antibodies, fully human antibodies, heteroconjugate antibodies (e.g., bispecific antibodies, diabodies, triabodies, and tetrabodies), and antigen binding fragments of antibodies, including e.g., Fab', F(ab')2, Fab, Fv, rIgG, and scFv fragments. Moreover, unless otherwise indicated, the term "monoclonal antibody" is meant to include both intact molecules, as well as, antibody fragments (such as, for example, Fab and F(ab')2 fragments) which are capable of specifically binding to the antigen. An antibody may include an immunoglobulin constant domain from any immunoglobulin, such as IgG1, IgG2, IgG3, or IgG4 subtypes, IgA (including IgA1 and IgA2), IgE, IgD or IgM.

In some embodiments, the immune checkpoint inhibitor is an antibody (e.g., a monoclonal antibody such as a human or humanized monoclonal antibody) to an immune checkpoint molecule, such as programmed cell death 1 protein (PD-1), programmed cell death 1 protein ligand 1 (PD-L1), cytotoxic T-lymphocyte-associated protein 4 (CTLA-4), T-cell immunoglobulin domain and mucin domain 3 (TIM3), lymphocyte activation gene-3 (LAG3), V-set domain-containing T-cell activation inhibitor 1 (VTCN1 or B7-H4), cluster of differentiation 276 (CD276 or B7-H3), B and T lymphocyte attenuator (BTLA), galectin-9 (GALS), checkpoint kinase 1 (Chk1), adenosine A2A receptor (A2AR), indoleamine 2,3-dioxygenase (IDO), killer-cell immunoglobulin-like receptor (KIR), or V-domain Ig suppressor of T cell activation (VISTA).

In some embodiments, immune checkpoint inhibitor is a small molecule, wherein the molecular weight of the small molecule is not more than 1,500 g/mol.

In some embodiments, the immune checkpoint inhibitor is a Programmed Cell Death Ligand 1 (PD-L1) or Programmed Cell Death 1 (PD-1) inhibitor.

A PD-1 inhibitor, as used herein is an agent that inhibits or prevents PD-1 activity, e.g., by binding to PD-1. A PD-1 inhibitor may reduce PD-1 activity in a cell or organism, e.g., by at least 5%, at least 10%, at least 20%, at least 30%, at least 40%, at least 50%, at least 60%, at least 70%, at least 80%, at least 90%, or about 100%, compared to a cell or organism that has not been exposed to the PD-1 inhibitor. Human PD-1 is encoded by the gene PDCD1 (Genbank Entrez ID 5133). PD-1 functions as an immune checkpoint and negatively regulates immune responses, e.g. inhibiting the activation, expansion, and/or function of CD8+ T-cells and other immune cells. PD-L1 is a ligand for PD-1. PD-L1 is a type 1 transmembrane protein with immunoglobulin V-like and C-like domains. Human PD-L1 is encoded by the CD274 gene (Genbank Entrez ID 29126). PD-L1 is also a ligand for B7.1.

PD-1 activity may be interfered with by antibodies that bind selectively to and block the activity of PD-1. The activity of PD-1 can also be inhibited or blocked by molecules other than antibodies, such as proteins, small molecules, and peptides, that bind PD-1. Agents that bind to and degrade or inhibit the DNA or mRNA encoding PD-1 also can act as PD-1 inhibitor. Examples include anti-PD-1 siRNAs and anti-PD-1 antisense oligonucleotides.

A PD-L1 inhibitor, as used herein is an agent that inhibits or prevents PD-L1 activity, e.g., by binding to PD-L1. A PD-L1 inhibitor may reduce PD-L1 activity in a cell or organism, e.g., by at least 5%, at least 10%, at least 20%, at least 30%, at least 40%, at least 50%, at least 60%, at least 70%, at least 80%, at least 90%, or about 100%, compared to a cell or organism that has not been exposed to the PD-L1 inhibitor.

PD-L1 activity may be blocked by molecules that selectively bind to and block the activity of PD-L1, e.g. by blocking the interaction with and activation of PD-1 and/or B7-1. The activity of PD-L1 can also be inhibited or blocked by molecules other than antibodies, such as proteins, small molecules, and peptides, that bind PD-L1. Agents that bind to and degrade or inhibit the DNA or mRNA encoding PD-L1 also can act as PD-L1 inhibitors. Examples include anti-PD-L1 siRNAs and anti-PD-L1 antisense oligonucleotides.

Example PD-1 inhibitors include those described in U.S. Publications 20130280265, 20130237580, 20130230514, 20130109843, 20130108651, 20130017199, 20120251537, and 20110271358, and in European Patent EP2170959B1, the entire disclosures of which are incorporated herein by reference.

Example PD-1 inhibitors include: nivolumab (e.g., OPDIVO® from Bristol-Myers Squibb), a fully human IgG4 monoclonal antibody that binds PD-1; pidilizumab (e.g., CT-011 from CureTech), a humanized IgG1 monoclonal antibody that binds PD-1; pembrolizumab (e.g., KEYTRUDA® from Merck), a humanized IgG4-kappa monoclonal antibody that binds PD-1; MEDI-0680 (AstraZeneca/MedImmune) a monoclonal antibody that binds PD-1; and REGN2810 (Regeneron/Sanofi) a monoclonal antibody that binds PD-1. Another exemplary PD-1 inhibitor is AMP-224 (Glaxo Smith Kline and Amplimmune), a recombinant fusion protein composed of the extracellular domain of the Programmed Cell Death Ligand 2 (PD-L2) and the Fc region of human IgG1, that binds to PD-1.

Example PD-L1 inhibitors include those described in U.S. Publications 20090055944, 20100203056, 20120039906, 20130045202, 20130309250, and 20160108123, the entire disclosures of which are incorporated herein by reference.

Example PD-L1 inhibitors include, for example: atezolizumab (also called TECENTRIQ™, Genentech/Roche), an human monoclonal antibody that binds to PD-L1; durvalumab (also called MEDI4736, AstraZeneca/MedImmune), a human immunoglobulin IgG1 kappa monoclonal antibody that binds to PD-L1; BMS-936559 (Bristol-Meyers Squibb), a fully human IgG4 monoclonal antibody that binds to PD-L1; avelumab (also called MSB 0010718C, Merck KGaA/Pfizer), a fully human IgG1 monoclonal antibody that binds to PD-L1; and CA-170 (Aurigene/Curis) a small molecule antagonist of PD-L1.

In some embodiments, the immune checkpoint inhibitor is a cytotoxic T-lymphocyte-associated protein 4 (CTLA-4) inhibitor.

A CTLA-4 inhibitor, as used herein is an agent that inhibits or prevents CTLA-4 activity, e.g., by binding to CTLA-4. A CTLA-4 inhibitor may reduce CTLA-4 activity in a cell or organism, e.g., by at least 5%, at least 10%, at least 20%, at least 30%, at least 40%, at least 50%, at least 60%, at least 70%, at least 80%, at least 90%, or about 100%, compared to a cell or organism that has not been exposed to the CTLA-4 inhibitor. Human CTLA-4 is encoded by the gene CTLA4 (Genbank Entrez ID 1493). CTLA-4 negatively regulates immune responses, e.g. by transmitting inhibitory signals to T cells.

CTLA-4 activity may be interfered with by antibodies that bind selectively to and block the activity of CTLA-4. The activity of CTLA-4 can also be inhibited or blocked by molecules other than antibodies, such as proteins, small molecules, and peptides, that bind CTLA-4. Agents that bind to and degrade or inhibit the DNA or mRNA encoding CTLA-4 also can act as CTLA-4 antagonists. Examples include anti-CTLA-4 siRNAs and anti-CTLA-4 antisense oligonucleotides.

Example CTLA-4 antagonists include those described in PCT Publication Nos. WO2001/014424, WO2012/118750, European Patent No. EP1212422B1, U.S. Pat. Nos. 5,811, 097, 5,855,887, 6,051,227, 6,984,720, 7,034,121, 7,824,679, 8,017,114, 8,475,790, 8,318,916, 8,685,394, U.S. Publication Nos. 2002/0039581, 2005/0201994, and 2009/0117037, the entire disclosures of which are incorporated herein by reference.

Example CTLA-4 antagonists include: ipilimumab (YERVOY®, Bristol-Myers Squibb), which is a recombinant human IgG1 monoclonal antibody against CTLA-4, and tremelimumab (AstraZeneca; MedImmune/Pfizer), which is a human IgG2 monoclonal antibody against CTLA-4.

In some embodiments, the immune checkpoint inhibitor is a T-cell immunoglobulin domain and mucin domain 3 (TIM3) inhibitor, lymphocyte activation gene-3 (LAG3) inhibitor, V-set domain-containing T-cell activation inhibitor 1 (VTCN1 or B7-H4) inhibitor, cluster of differentiation 276 (CD276 or B7-H3) inhibitor, B and T lymphocyte attenuator (BTLA) inhibitor, galectin-9 (GALS) inhibitor, checkpoint kinase 1 (Chk1) inhibitor, adenosine A2A receptor (A2AR) inhibitor, indoleamine 2,3-dioxygenase (IDO) inhibitor, killer-cell immunoglobulin-like receptor (KIR) inhibitor, or V-domain Ig suppressor of T cell activation (VISTA) inhibitor.

Methods of Treatment

In some aspects, the disclosure relates to methods of treatment, e.g., treatment of cancer. In some embodiments, the method comprises administering a selective histone deacetylase 3 (HDAC3) inhibitor as described herein and/or administering an immunotherapy agent (e.g., an immune checkpoint inhibitor) as described herein to a subject in need thereof as described herein, e.g., a subject having cancer. In some embodiments, the subject is a subject to whom has already been administered a selective HDAC3 inhibitor as described herein and/or administering an immunotherapy agent (e.g., an immune checkpoint inhibitor) as described herein. In some embodiments, the combined amount of the selective HDAC3 inhibitor and the immunotherapy agent is effective for treating the cancer and/or is more effective for treating the cancer than either the selective HDAC3 inhibitor or the immunotherapy agent used alone. In some embodiments, the selective HDAC3 inhibitor and the immunotherapy agent act synergistically to treat the cancer compared to either the selective HDAC3 inhibitor or the immunotherapy agent used alone.

In some embodiments, the method is a method of inhibiting (e.g., by at least 5%, at least 10%, at least 20%, at least 30%, at least 40%, at least 50%, at least 60%, at least 70%, at least 80%, at least 90%, or about 100%) proliferation of cancer cells or inducing death (e.g., by at least 5%, at least 10%, at least 20%, at least 30%, at least 40%, at least 50%, at least 60%, at least 70%, at least 80%, at least 90%, or about 100%) of cancer cells in a subject, the method comprising administering a selective HDAC3 inhibitor as described herein and/or administering an immunotherapy agent (e.g., an immune checkpoint inhibitor) as described herein to a subject in need thereof as described herein, e.g., a subject having cancer. In some embodiments, the combined amount of the selective HDAC3 inhibitor and the immunotherapy agent is effective for inhibiting proliferation of the cancer cells or inducing death of the cancer cells and/or is more effective for inhibiting proliferation of the cancer cells or inducing death of the cancer cells than either the selective HDAC3 inhibitor or the immunotherapy agent used alone. In some embodiments, the selective HDAC3 inhibitor and the immunotherapy agent act synergistically to treat the cancer compared to either the inhibitor or the immunotherapy agent used alone.

In some embodiments of any of the methods described herein, the step of administering the selective HDAC3 inhibitor is prior to (e.g., at least: 1 hour, 2 hours, 6 hours, 12 hours, 1 day, 2 days, 3 days, 5 days, 1 week, 2 weeks, 3 weeks, or 1 month, prior to), concurrently with, or subsequent to (e.g., at least: 1 hour, 2 hours, 6 hours, 12 hours, 1 day, 2 days, 3 days, 5 days, 1 week, 2 weeks, 3 weeks, or 1 month, subsequent to) the step of administering the immunotherapy agent. In some embodiments, the step of administering the immunotherapy agent is prior to, concurrently with, or subsequent to the step of administering the selective HDAC3 inhibitor. In some embodiments, the selective HDAC3 inhibitor is administered more than once. In some embodiments, the immunotherapy agent is administered more than once.

In some embodiments of any of the methods described herein, the ratio of the amount of the selective HDAC3 inhibitor to the amount of the immunotherapy agent administered, by weight, is between 0.01 and 100 (e.g., between 0.1 and 10), inclusive.

In some embodiments of any of the methods described herein, the method comprises further administering an additional pharmaceutical agent, wherein the additional pharmaceutical agent is different from the selective HDAC3 inhibitor and the immunotherapy agent. In certain embodiments, the additional pharmaceutical agent is selected from the group consisting of antimicrobial agents, analgesics, antiinflammatory agents, counterirritants, coagulation modifying agents, diuretics, sympathoaminoetics, anorexics, antacids and other gastrointestinal agents; antiparasitics, antidepressants, antihypertensives, anticholinergics, stimulants, antihormones, central and respiratory stimulants, drug antagonists, lipid-regulating agents, uricosurics, cardiac glycosides, electrolytes, ergot and derivatives thereof, expectorants, hypnotics and sedatives, antidiabetic agents, dopaminergic agents, antiemetics, muscle relaxants, parasympathoaminoetics, anticonvulsants, antihistamines, beta-blockers, purgatives, antiarrhythmics, contrast materials, radiopharmaceuticals, antiallergic agents, tranquilizers, vasodilators, antiviral agents, and antineoplastic or cytostatic agents or other agents with anticancer properties, and combinations thereof. In certain embodiments, the additional pharmaceutical agent is a contraceptive, vitamin, micronutrient, or macronutrient, or a combination thereof. In certain embodiments, the additional pharmaceutical agent is selected from the group consisting of antiinfectives such as antibiotics and antiviral agents; analgesics and analgesic combinations; anorexics; antiheimintics; antiarthritics; antiasthmatic agents; anticonvulsants; antidepressants; antidiuretic agents; antidiarrleals; antihistamines; antiinflammatory agents; antimigraine preparations; antinauseants; antineoplastics; antiparkinsonism drugs; antipruritics; antipsychotics; antipyretics, antispasmodics; anticholinergics; sympathoaminoetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins. In certain embodiments, the additional pharmaceutical agent is an anti-cancer agent (e.g., biotherapeutic anti-cancer agent and chemotherapeutic agent). Exemplary biotherapeutic anti-cancer agents include, but are not limited to, interferons, cytokines (e.g., tumor necrosis factor, interferon $\alpha$, interferon $\gamma$), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g., Herceptin (trastuzumab), T-DM1, AVASTIN (bevacizumab), ERBITUX (cetuximab), Vectibix (panitumumab), Rituxan (rituximab), Bexxar (tositumomab)). Exemplary chemotherapeutic agents include, but are not limited to, anti-estrogens (e.g., tamoxifen, raloxifene, and megestrol), LHRH agonists (e.g., goscrclin and leuprolide), anti-androgens (e.g., flutamide and bicalutamide), photodynamic therapies (e.g., vertoporfin (BPD-MA), phthalocyanine, photosensitizer Pc4, and demethoxy-hypocrellin A (2BA-2-DMHA)), nitrogen mustards (e.g., cyclophosphamide, ifosfamide, trofosfamide, chlorambucil, estramustine, and melphalan), nitrosoureas (e.g., carmustine (BCNU) and lomustine (CCNU)), alkylsulphonates (e.g., busulfan and treosulfan), triazenes (e.g., dacarbazine, temoxolomide), platinum containing compounds (e.g., cisplatin, carboplatin, oxaliplatin), vinca alkaloids (e.g., vincristine, vinblastine, vindesine, and vinorelbine), taxoids (e.g., paclitaxel or a paclitaxel equivalent) docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g., etoposide, etoposide phosphate, teniposide, topotecan, 9-aminocamptothecin, camptoirinotecan, irinotecan, crisnatol, mytomycin C), anti-metabolites, DHFR inhibitors (e.g., methotrexate, dichloromethotrexate, trimetrexate, edatrexate), IMP dehydrogenase inhibitors (e.g., mycophenolic acid, tiazofurin, ribavirin, and EICAR), ribonucleotide reductase inhibitors (e.g. hydroxyurea and deferoxamine), uracil analogs (e.g., 5-fluorouracil (5-FU), floxuridine, doxifluridine, ratitrexed, tegafur-uracil, capecitabine), cytosine analogs (e.g., cytarabine (ara C), cytosine arabinoside, and fludarabine), purine analogs (e.g., mercaptopurine and Thioguanine), Vitamin D3 analogs (e.g., EB 1089, CB 1093, and KH 1060), isoprenylation inhibitors (e.g., lovastatin), dopaminergic neurotoxins (e.g., 1-methyl-4-phenylpyridinium ion), cell cycle inhibitors (e.g., staurosporine), actinomycin (e.g., actinomycin D, dactinomycin), bleomycin (e.g., bleomycin A2, bleomycin B2, peplomycin), anthracycline (e.g., daunorubicin, doxorubicin, pegylated liposomal doxorubicin, idarubicin, epirubicin, pirarubicin, zorubicin, mitoxantrone), MDR inhibitors (e.g., verapamil), $Ca^{2+}$ ATPase inhibitors (e.g., thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab oxogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (Velcade)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe), and OSI-027 (OSI)), oblimersen, gemeitabine, caaminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, caaminomycin, aminopterin, and hexamethyl melamine, and combinations thereof.

An "effective amount" of an agent generally refers to an amount sufficient to elicit the desired biological response, e.g., treat the condition. As will be appreciated by those of ordinary skill in this art, the effective amount of an agent described herein may vary depending on such factors as the condition being treated, the mode of administration, and the age, body composition, and health of the subject. The effective amount may encompass an amount that improves overall therapy, reduces or avoids symptoms or causes of the condition, or enhances the therapeutic efficacy of another therapeutic agent. For treatment of cancer, an effective amount is an amount sufficient to provide a therapeutic benefit in the treatment of the cancer, such as to slow, halt or reverse the growth of cancer cells and/or to kill cancer cells, or to reduce or eliminate one or more symptoms associated with the cancer.

Exemplary effective amounts for antibodies, such as anti-PD-1, anti-PD-L1 antibodies or anti-CTLA4 antibodies include 0.01 mg/kg to 20 mg/kg every 1-4 weeks. In embodiments, such administration is for so long as the disease, e.g., cancer, persists.

Any agent or inhibitor described herein may be administered by any suitable route as needed for the particular condition being treated, e.g., cancer. For example, an agent or inhibitor described herein may be administered parenterally (e.g., intravenous, intraarterial, intraperitoneal, intrathecal, intraventricular, intraurethral, intrasternal, intracranial, intramuscular, intra-ossial, intranodal, intradermal and subcutaneous) or orally. In some embodiments an antibody as described herein is administered parenterally, e.g., intravenously. It is to be understood that the administration route for an agent or inhibitor described herein may vary depending on the type of subject being treated, the disease being treated (e.g., the type of cancer), and the severity of the disease. In some embodiments of any of the methods described herein, an immunotherapy agent as described herein (e.g., a checkpoint inhibitor) is administered to the subject in need thereof orally, topically, by injection, or by implantation. In some embodiments of any of the methods described herein, a selective HDAC3 inhibitor as described herein is administered to the subject in need thereof orally.

Formulations

Any agents or inhibitors described herein may be formulated as a pharmaceutical composition. The term "pharmaceutical composition" or "formulation" refers to preparations which are in such form as to permit the biological activity of the active ingredients to be effective. In some embodiments, a pharmaceutical composition comprises an agent or inhibitor as described herein and a pharmaceutically acceptable carrier. As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, normal (0.9%) saline, 5% dextrose, albumin, emulsions such as oil/water emulsion, and various types of wetting agents. Compositions comprising such carriers are formulated by well-known conventional methods (see, e.g., Remington, The Science and Practice of Pharmacy 20th Ed. Mack Publishing, 2000).

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan monostearate (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotoxoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

Subjects

Methods described herein utilize subjects, such as subjects having or suspected of having cancer. In some embodiments, the subject is a mammalian subject such as a human subject having or suspected of having cancer. Other exemplary subjects include non-human primates, pigs, horses, sheep, cows, rabbits, dogs, cats, rats and mice.

In some embodiments, the subject is a subject to whom has already been administered a selective HDAC3 inhibitor as described herein and/or administering an immunotherapy agent (e.g., an immune checkpoint inhibitor) as described herein.

In some embodiments, the subject has a cancer that is responsive to a selective HDAC3 inhibitor as described herein such that administration of the selective HDAC3 inhibitor to the subject is effective for increasing expression of a major histocompatibility complex (MHC) class II protein (e.g., HLA-DR) in at least one of the cancer cells. In some embodiments, the subject has a cancer that is associated with decreased (e.g., by at least 5%, at least 10%, at least 20%, at least 30%, at least 40%, at least 50%, at least 60%, at least 70%, at least 80%, or at least 90%) expression of an MHC class II protein. Human MHC class II is a heterodimer containing an alpha and beta chain. Human genes that encode human MHC class II alpha and beta chains include HLA-DMA, HLA-DMB, HLA-DOA, HLA-DOB, HLA-DPA1, HLA-DPB1, HLA-DQA1, HLA-DQA2, HLA-DQB1, HLA-DQB2, HLA-DRA, HLA-DRB1, HLA-DRB3, HLA-DRB4, and HLA-DRB5. Mouse MHC class II Expression levels of a MHC class II protein can be measured using any method known in the art or described herein, e.g., using immunoassays, such as enzyme linked immunoabsorbant assay (ELISA), radioimmunoassay (RIA), Immunoradiometric assay (IRMA), Western blotting, flow cytometry, fluorescence-activated cell sorting (FACS), immunocytochemistry or immunohistochemistry.

In some embodiments, the subject has a cancer that is responsive to an immunotherapy agent as described herein. In some embodiments, a subject has a cancer that is responsive to an immunotherapy agent as described herein if this subject has a reduced tumor burden (e.g., due to reduced proliferation of cancer cells and/or increased induction of death of cancer cells) after administration of the immunotherapy agent.

In some embodiments, the subject has a cancer that recruits or is capable of recruiting immune cells, e.g., macrophages and/or T cells (e.g., CD8+, CD3+ and/or CD4+ cells). In some embodiments, a cancer recruits or is capable of recruiting immune cells if immune cells (e.g., at least $10^1$, $10^2$, $10^3$, $10^4$, $10^5$, or more immune cells) are detectable in a tumor sample from the subject. Recruitment of such cells can be measured using any method known in the art or described herein, e.g., by labeling macrophages and/or T cells (e.g., CD8+, CD3+ and/or CD4+ cells) in the cancer, optionally through biopsy of a sample of the cancer and labeling of macrophages and/or T cells in the biopsy sample. Labeling can be accomplished, e.g., using antibodies specific for surface markers on the cells, e.g., CD8, CD3 and/or CD4. The cells may be analyzed, e.g., using FACS, light microscopy or fluorescence microscopy. In some embodiments, the subject has a cancer that recruits immune cells or increases (e.g., by at least 10%, at least 30%, at least 100%, at least 3-fold, at least 10-fold, at least 30-fold, or at least 100-fold) recruitment of immune cells upon administration of a selective HDAC3 inhibitor as described herein to the subject. In some embodiments, the subject has a cancer that recruits immune cells or increases (e.g., by at least 10%, at least 30%, at least 100%, at least 3-fold, at least 10-fold, at least 30-fold, or at least 100-fold) recruitment of immune cells upon administration of a selective HDAC3 inhibitor as described herein and an immunotherapy agent (e.g., an immune checkpoint inhibitor) as described herein to the subject.

In some embodiments, the subject has a cancer that comprises a mutation in a gene encoding a cAMP-response element-binding protein (CREB) binding protein (CREBBP) or EIA-associated protein p300 (EP300). In some embodiments, the mutation is associated with the decreased (e.g., by at least 5%, at least 10%, at least 20%, at least 30%, at least 40%, at least 50%, at least 60%, at least 70%, at least 80%, or at least 90%) expression of an MHC class II protein.

In some embodiments, the subject has kidney cancer, melanoma, breast cancer, non-small cell lung cancer, non-Hodgkin lymphoma, head and neck cancer, Hodgkin's lymphoma, or bladder cancer. In some embodiments, the subject has kidney cancer. Diagnosis of a particular cancer is within the skill of an ordinary medical practitioner, e.g. using any one or more of a biopsy (e.g., by needle, by endoscope or by surgery), CT scan, nuclear scan, ultrasound, MRI, PET scan, and X-ray.

Kits

Other aspects of the disclosure relate to kits, such as kits suitable for performing a method described herein, e.g., treating cancer. In some embodiments, the kit comprises a selective histone deacetylase 3 (HDAC3) inhibitor as described herein and an immunotherapy agent (e.g., an immune checkpoint inhibitor) as described herein, e.g., housed in separate containers. In some embodiments, the kit further comprises a delivery device, e.g., a syringe. In some embodiments, the kit comprises instructions, e.g., for using the selective HDAC3 inhibitor and the immunotherapy agent. In some embodiments, the instructions include one or more steps of a method as described herein. In some embodiments, the ratio of the amount of the selective HDAC3 inhibitor to the amount of the immunotherapy agent in the kit, by weight, is between 0.1 and 10, inclusive.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1. Synthesis of Selective HDAC3 Inhibitors

In some experiments, the compounds (e.g., selective HDAC3 inhibitors (e.g., I-1, II-234, and RGFP966)) described herein were synthesized according to the methods described in U.S. patent application publications and/or U.S. patents, US 20150191427, US 20140080802, U.S. Pat. Nos. 9,512,143, 9,796,664, 9,540,395, and/or US 20160272579, incorporated herein by reference.

Example 2. Inhibition of Histone Deacetylase Enzymatic Activity

In some experiments, the following non-trypsin coupled in-vitro HDAC enzymatic endpoint assay was used to assay the compounds described herein. Below is a standardized protocol for running HDAC selectivity panel on Caliper LabChip EZ-Reader Instrument.

The Caliper HDAC Assay Buffer (acronym HAB, 1 liter) was prepared as follows:

| Components: | Final Concentration: | Catalog #s: |
|---|---|---|
| 100 mL 1M KCL | 100 mM | Sigma #9541-500G |
| 50 mL 1M HEPES, pH 7.4 | 50 mM | Sigma #H3375-1KG |
| 1 mL 10% BSA | 0.01% | SeraCare #AP-4510-80-100G |
| 20 µL 50% Tween-20 | 0.001% | Zymed #00-3005-20mL |

The components were added to 1 liter Milli-Q water and store at 4° C.

The substrate (stock conc.) was prepared as follows:
Substrate A was prepared as 2 mM in DMSO. Its final concentration in the assay for HDACs 1,2,3,6 is 2 µM.
Substrate B was prepared as 2 mM in 100% DMSO. Its final concentration in the assay for HDACs 4,5,7,8,9 is 2 µM.

LBH was used as quench inhibitor to stop the reaction at the end point. The instrument buffer was ProfilerPro Separation Buffer (e.g., Caliper #760367). The instrument chip was LabChip EZ Reader II 12-Sipper Off-Chip Mobility Shift Chip (e.g., Caliper #760404).

Substrate A and B structures are shown below and prepared according to the synthetic procedure described in WO 2013/06739.

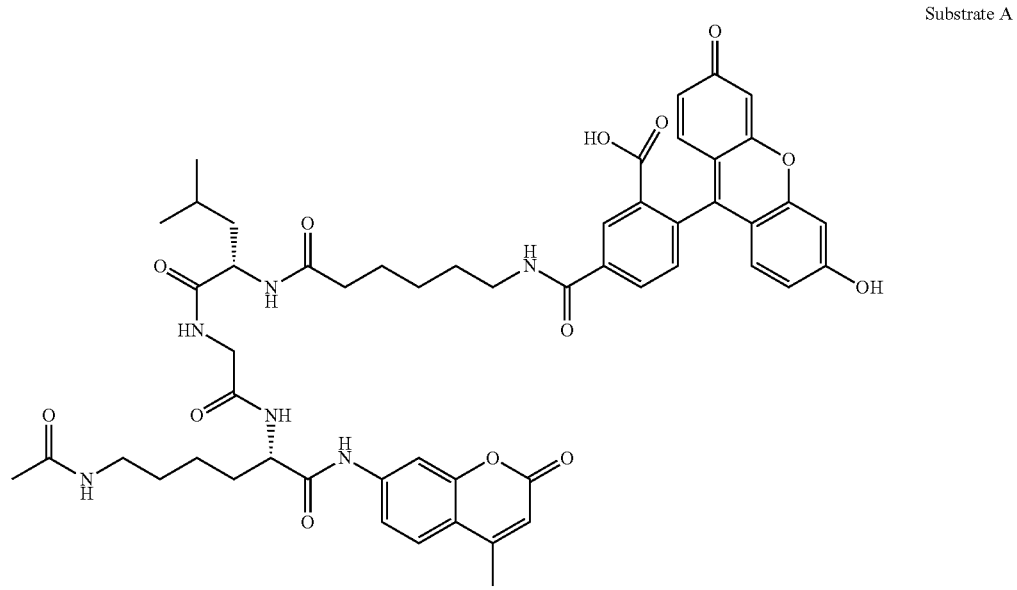

Substrate A

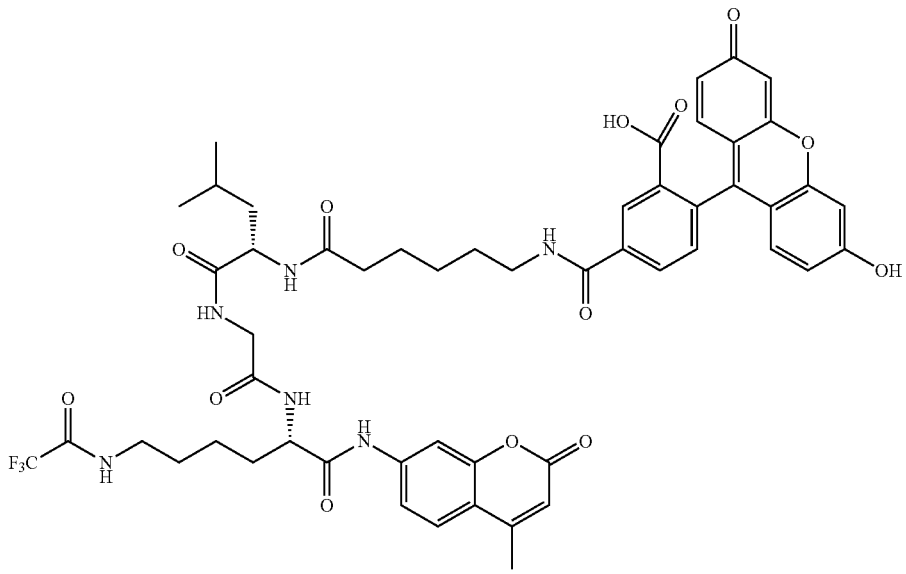

Substrate B

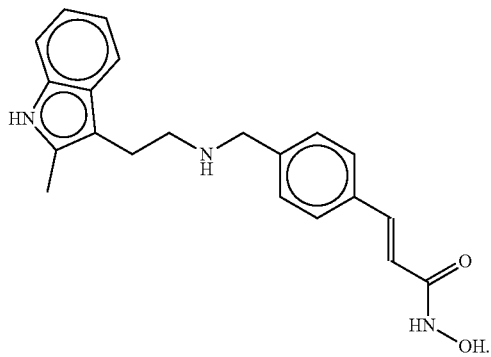

(LBH)

The protocol was carried out as follows:
1. Caliper LabChip and 1 µM Marker (peptide substrate in separation buffer) were prepared for instrument run.
2. Warm up Caliper HAB buffer to room temperature
3. Pin 100 nl compd. into 20 µl 1.5× solution HDACs and preincubate 3 hrs at room temperature
4. Add 10 µl 3× solution acetylated substrate to initiate the reaction for 50 minutes.
5. Stop reaction with 5 µL of 10 µM LBH solution (~1.4 µM final)
6. Mix plate
7. Read plate on EZ Reader instrument. Separate substrate and product peaks by capillary electrophoresis and read fluorescence from both substrate and product.

8. Run parameters were as follows:

| | Pressure | Upstream votage | Downstream votage | Post sample buffer sip time | Final delay | Peak order |
|---|---|---|---|---|---|---|
| Substrate A | −1.3 | −500 | −1500 | 35 | 90 | Product first |
| Substrate B | −1.3 | −500 | −1700 | 35 | 90 | Product first |

Below is the HDAC and Substrate concentration used in this assay.
| HDAC | BPS Cat. # | Substrate | Substrate Conc. (µM) | Stock enz. (µM) | Final enz. (nM) | Conversion % @1 hr |
|---|---|---|---|---|---|---|
| 1 | 50051 | Substrate A | 2 | 4.82 | 5 | 27% |
| 2 | 50002 | Substrate A | 2 | 44 | 3 | 20% |
| 3 | 50003 | Substrate A | 2 | 7.67 | 5 | 30% |
| 4 | 50004 | Substrate B | 2 | 26.6 | 0.5 | 38% |
| 5 | 50045 | Substrate B | 2 | 0.567 | 1 | 17% |
| 6 | 50006 | Substrate A | 2 | 5.66 | 2 | 29% |
| 7 | 50007 | Substrate B | 2 | 8.97 | 0.5 | 45% |
| 8 | 50008 | Substrate B | 2 | 12.93 | 0.5 | 22% |
| 9 | 50009 | Substrate B | 2 | 57.99 | 3 | 25% |
Preparation of Substrates A and B:
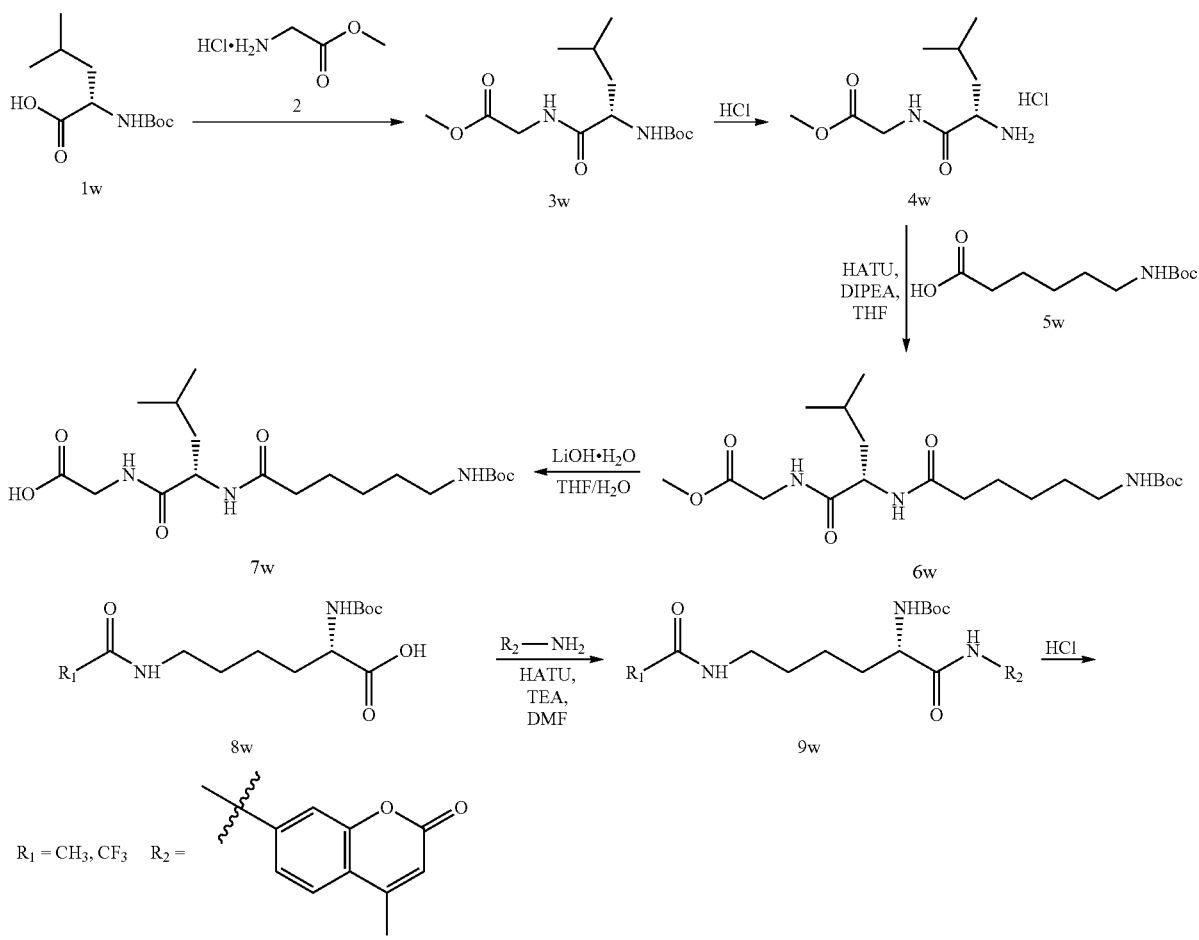
Scheme 1
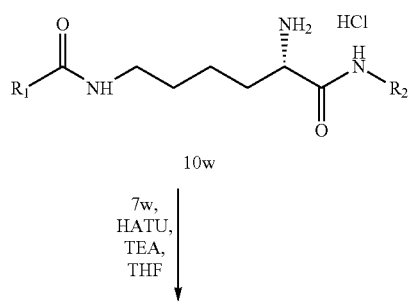

-continued

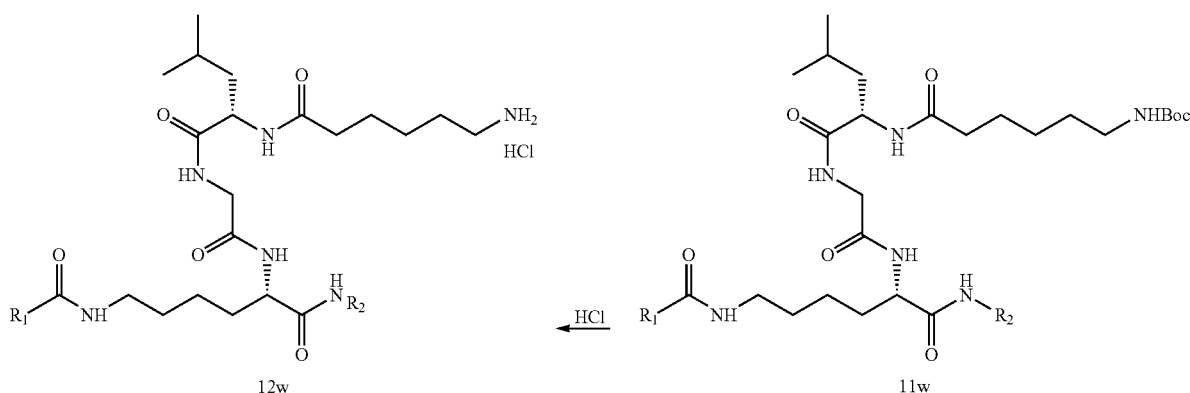

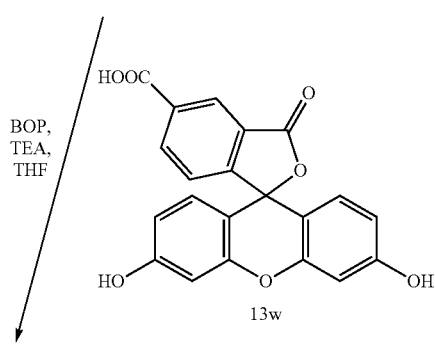

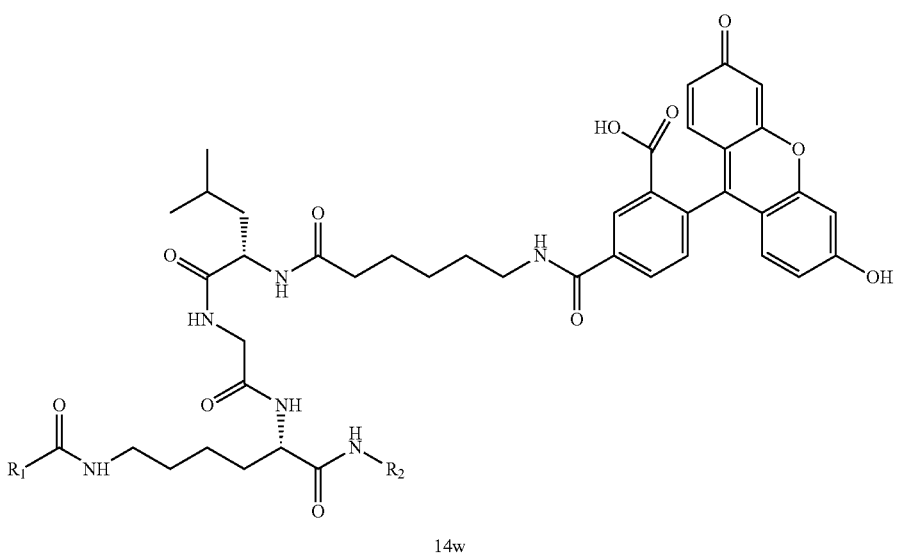

In one aspect, substrates A and B were prepared as follows. To a solution of (S)-2-((tert-butoxycarbonyl)amino)-4-methylpentanoic acid (1w) in THF was added methyl 2-aminoacetate hydrochloride (2w), Et₃N and HATU. The mixture was stirred at room temperature for 16 h. The reaction was filtered through Celite. The reaction filtrate was diluted with 100 mL of water and stirred for 15 min. The suspension was filtered off, rinsed with water and dried to afford (S)-methyl 2-(2-((tert-butoxycarbonyl)amino)-4-methylpentanamido)acetate (3w).

To a solution of (S)-methyl 2-(2-((tert-butoxycarbonyl)amino)-4-methylpentanamido) acetate (3w) in 1,4-dioxane was added a 5M solution of HCl in 1,4-dioxane at room temperature. The reaction was stirred at room temperature for 16 h. The reaction mixture was filtered to afford (S)-methyl 2-(2-amino-4-methylpentanamido)acetate hydrochloride (4w) as the filtered solid.

To a solution of (S)-methyl 2-(2-amino-4-methylpentanamido)acetate hydrochloride (4w) in THF was added 6-((tert-butoxycarbonyl)amino) hexanoic acid, HATU and DIPEA. The reaction was stirred at room temperature for 18 h. The mixture was then filtered through Celite. The filtrate was concentrated under reduced pressure and the crude residue was purified by column chromatography (silica gel, $CH_2Cl_2$/MeOH=50/1) to give (S)-methyl 13-isobutyl-2,2-dimethyl-4,11,14-trioxo-3-oxa-5,12,15-triazaheptadecan-17-oate (6w) as a white solid.

To a solution of (S)-methyl 13-isobutyl-2,2-dimethyl-4,11,14-trioxo-3-oxa-5,12,15-triazaheptadecan-17-oate (6w) in THF was added a solution of $LiOH \cdot H_2O$ in water at room temperature. After 3 h, the reaction mixture was concentrated, diluted with water and acidified with a 1N aqueous solution of HCl to about pH 4-5. The mixture was stirred for 15 min and the white precipitate formed was filtered off, rinsed with water, and dried to afford (S)-13-isobutyl-2,2-dimethyl-4,11,14-trioxo-3-oxa-5,12,15-triazaheptadecan-17-oic acid (7w).

To a solution of 8w in DMF at room temperature was added 7-amino-4-methyl-2H-chromen-2-one, HATU and triethylamine. The reaction was stirred at room temperature for 2 h. A saturated solution of sodium bicarbonate was added. The product was extracted with ethyl acetate. The combined organic layers were washed with water, dried over sodium sulfate, filtered and concentrated under reduced pressure. The crude residue was purified by prep-HPLC to afford 9w.

To a solution of 9w in 1,4-dioxane was added a 5M solution of HCl in 1,4-dioxane. The reaction was stirred at room temperature for 3 h. The mixture was concentrated under reduced pressure to afford 10w.

To a solution of 10w in THF was added 7, HATU and triethylamine. The reaction was stirred at room temperature for 3 h. A saturated solution of sodium bicarbonate was added. The product was extracted with ethyl acetate. The combined organic layers were washed with water, dried over sodium sulfate, filtered and concentrated under reduced pressure. The crude material was purified by silica gel column (prep-HPLC) to afford 11w.

To a solution of 11w in 1,4-dioxane and was added a 5M solution of HCl in 1,4-dioxane. The reaction was stirred at room temperature for 3 h. The reaction was then concentrated and dried under reduced pressure to afford 12w.

To a solution of 12w in THF at room temperature was added 13w, BOP and triethylamine. The reaction was stirred at room temperature for 22 h. The mixture was then filtered through Celite. The filtrate was concentrated under reduced pressure. The crude residue was purified by prep-HPLC to give 14w.

In some experiments, the compounds described herein were assayed for histone deacetylase inhibitory activity as described above. Exemplary results are shown in the table below.

| Compound # | $IC_{50}$ (μM) | | | | | | | | |
|---|---|---|---|---|---|---|---|---|---|
| | HDAC1 | HDAC2 | HDAC3 | HDAC4 | HDAC5 | HDAC6 | HDAC7 | HDAC8 | HDAC9 |
| I-1 | 2.190 | 1.510 | 0.061 | >30 | >30 | >30 | >30 | >30 | >30 |
| II-234 | 5.140 | 4.450 | 0.147 | ND | ND | ND | ND | ND | ND |
| RGFP966 | 3.350 | 3.000 | 0.043 | ND | ND | ND | ND | ND | ND |

"ND" denotes "not determined."

Example 3. Combination Therapy Including Selective HDAC3 Inhibitor and Checkpoint Inhibitor The functional activity and efficacy of a combination of an HDAC3 inhibitor, I-1, and checkpoint inhibitors in various cancers was investigated. As described below, it was surprisingly discovered that the combination was effective in cancers that (a) had major histocompatibility complex (MHC) class II protein expression that is inducible with the HDAC3 inhibitor as a single agent and (b) were capable of being infiltrated by macrophages and T cells.

Methods

Cell Culture and Compound Treatment for MHC II Induction

Human and murine tumor cell lines were obtained from the Shanghai Institutes for Biological Sciences (SIBS) or American Type Culture Collection (ATCC) and maintained in a humidified 5% $CO_2$ incubator at 37° C. All of the human cell lines were derived from human B cell lymphomas: OCI-Ly19, OCI-Ly7, OCI-Ly18, RL, SU-DHL6, and MD901. The murine tumor cell lines were of varied origin: CT-26 (colon carcinoma), RENCA (renal cell carcinoma), P388D1 (lymphoblast of monocytes and macrophages), MPC-11 (plasmacytoma, myeloma), L5178 (thymic lymphoma), and J588 (plasmacytoma, myeloma).

On Day 0, T25 flasks were seeded at the following cell densities:

| Cell line | Seeding density | Cell Culture Medium |
|---|---|---|
| P388D1 | 0.4 * 10^6 cells/5 mL/flask | RPMI1640 + 10% HS + Sodium pyruvate |
| MPC-11 | 0.1 * 10^6 cells/5 mL/flask | DMEM + 10% HS |
| CT-26 | 0.1 * 10^6 cells/5 mL/flask | RPMI-1640 + 10% FBS |
| J588 | 0.4 * 10^6 cells/5 mL/flask | DMEM + 10% HS |
| L5178 | 0.4 * 10^6 cells/5 mL/flask | Fischer's + 10% HS + 0.1 g/L sodium pyruvate + 1.125 g/L NaHCO3 |
| Renca | 0.1 * 10^6 cells/5 mL/flask | DMEM + 10% FBS |
| OCI-Ly7 | 1 * 10^6 cells/5 mL/flask | IMDM + 10% FBS |
| OCI-Ly19 | 1 * 10^6 cells/5 mL/flask | RPMI1640 + 10% FBS |
| RL | 1 * 10^6 cells/5 mL/flask | RPMI1640 + 10% FBS |
| SU-DHL-6 | 1 * 10^6 cells/5 mL/flask | RPMI1640 + 20% FBS |
| MD901 | 1 * 10^6 cells/5 mL/flask | RPMI1640 + 10% FBS |
| OCI-Ly18 | 1 * 10^6 cells/5 mL/flask | RPMI1640 + 10% FBS |

[abbreviations: RPMI = Roswell Park Memorial Institute; DMEM = Dulbecco's Modified Eagle's Medium; HS = Horse Serum; FBS = Fetal Bovine Serum; IMDM = Iscove's Modified Dulbecco's Medium]

On Day 1, cells were treated with I-1 compound diluted in DMSO/PBS (final concentration of DMSO in the media was 0.19%). The cells were treated with I-1 compound for 72 hours. The adherent cells were dissociated with 1 mL/T25 flask of Cell Dissociation buffer (GIBCO) at 37° C. Four mL of culture media was added to each flask, samples were aliquoted FACS analysis. For suspension cells, samples were aliquoted into 50 mL conical tubes for FACS analysis.

FACS Detection of MHC II on Human and Murine Cells (IA/IE on Murine Cells)

Cells were counted to determine cell number and viability with Vi-cell (Beckman). After washing once with 10 mL cold FACS staining buffer (PBS+0.2% BSA), liquid was aspirated and the cells were resuspended in enough cold FACS staining buffer to reach a final cell density of ~$1 \times 10^7$ viable cells/mL. 50 µL/well (~500 k/well) of cells were added to a 96-well u-bottomed plate and the cells were stained as follows, according to manufacturer's instructions:

Sample 1: Unstained
Sample 2: stained with anti MHC II antibody (PE anti-human HLA-DR, Clone: G46-6, Becton Dickinson; PE anti-mouse I-A/I-E, Clone: M5/114.15.2, Becton Dickinson)
Sample 3: stained with isotype control Cells were incubated for 1 hour at 4° C., protected from light. 100 µL cold FACS staining buffer was added to each well and the plate was centrifuged at 1500 rpm×3 minutes at 4° C. Supernatant was removed and the cells were resuspended in cold FACS staining Buffer at 200 µL/well and then pelleted at 1500 rpm×3 minutes at 4° C. The step was repeated 2 times. 150 µL cold FACS staining buffer was added to each well. Samples were analyzed immediately using FACS machine. The data were analyzed with BD Accuri C6 software and FlowJo_V10.

Tumor Growth Inhibition In Vivo—P388D1 Murine Lymphoma

On Day 0, each mouse (6-8 weeks old, DBA/2) was inoculated subcutaneously at the right lower region with P388D1 tumor cells ($1 \times 10^5$) in 0.1 ml of PBS for tumor development. The treatments were started 24 h after tumor cells inoculation. Mice were treated as follows:

| Group | N | Treatment | Dose (mg/kg) | Dosing Route | Dosing Schedule |
|---|---|---|---|---|---|
| 1 | 12 | I-1 | 50 | p.o. | BID × 14 days |
| 2 | 12 | Vehicle (0.5% HPMC, 0.05% Tween80, 7.5% Captisol) | 0 | p.o. | BID × 14 days |
| 3 | 12 | I-1 | 50 | p.o. | BID × 14 days |
|   |   | Anti-PD-1 (RMP1-14) | 10 | i.p. | BIW × 2 weeks |
| 4 | 12 | Anti-PD-1 (RMP1-14) | 10 | i.p. | BIW × 2 weeks |

[abbreviations: BIW = twice weekly; BID = twice daily at 12 hours intervals; i.p. = Intraperitoneally; p.o. = orally]

Formulation: I-1 was dissolved in vehicle solution, vortexed and sonicated for 30 minutes or as needed to get a homogenous suspension, and aliquoted to 2 vials for daily use. The dosing formulations were protected from light and dispensed daily. The dosing formulations were removed from the refrigerator, vortexed/stirred/sonicated for at least 30 minutes or as needed to assure it is a room temperature homogenous suspension before dosing. Anti-PD-1 (RMP1-14; BioXcell) was diluted with sterile PBS for each use.

Observations and Data Collection: After tumor cell inoculation, the animals were checked daily for morbidity and mortality. Tumor volumes were measured thrice weekly in two dimensions using a caliper, and the volume was expressed in mm$^3$ using the formula: $V = 0.5 \, a \times b^2$ where a and b are the long and short diameters of the tumor, respectively. The entire procedures of dosing as well as tumor and body weight measurement were conducted in a Laminar Flow cabinet. On Day 11, 5 mice/group were terminated for FACS analysis (satellite time point).

Sampling:
1) For pharmacokinetics (PK): 2 hrs after the first treatment, satellite time point (Day 11) and after the final time point (Day 14) 100 µl blood was collected from the I-1 treatment groups (3 mice/group), then centrifuged to get about 50 µl plasma for PK analysis.
2) For Satellite Groups: Tumors were collected for FACS analysis at 2 hrs post the morning dose at day 11.
3) Terminal tumor sampling from all remaining mice for FACS analysis: 2 hrs after the final treatment, tumors were collected from all remaining animals. If tumor size was sufficient, part of tumor was used for PK analysis and another for terminal FACS.

Tumor Growth Inhibition In Vivo—Renca Murine Renal Cell Carcinoma

On Day 0, each mouse (6-8 weeks old, Balb/c) was inoculated subcutaneously at the right lower region with Renca tumor cells ($1 \times 10^6$) in 0.1 ml of PBS for tumor development. The treatments were started 24 h after tumor cells inoculation. Mice were treated as follows:

| Group | N | Treatment | Dose (mg/kg) | Dosing Route | Dosing Schedule |
|---|---|---|---|---|---|
| 1 | 14 | Vehicle (0.5% HPMC, 0.05% Tween80, 7.5% Captisol) | 0 | p.o. | BID × 28 days |
| 2 | 14 | I-1 | 50 | p.o. | BID × 28 days |
| 3 | 14 | Anti-PD-1 (RMP1-14) | 10 | i.p. | BIW × 4 weeks |
| 4 | 14 | I-1 | 50 | p.o. | BID × 28 days |
|   |   | Anti PD-(RMP1-14) | 10 | i.p. | BIW × 4 weeks |
| 5 | 10 | I-1 | 10 | p.o. | BID × 28 days |
|   |   | Anti-PD-1 (RMP1-14) | 10 | i.p. | BIW × 4 weeks |
| 6 | 10 | I-1 | 3 | p.o. | BID × 28 days |
|   |   | Anti PD-(RMP1-14) | 10 | i.p. | BIW × 4 weeks |
| 7 | 10 | Anti-CTLA4 (9D9) | 10 | i.p. | Q3D × 28 days |
| 8 | 10 | I-1 | 50 | p.o. | BID × 28 days |
|   |   | Anti-CTLA4 (9D9) | 10 | i.p. | Q3D × 28 days |

Formulation, observations and sampling were as described above, with a satellite time point (5 mice/group) of Day 23 for some groups. Anti-CTLA4 antibody (BioXcell) was diluted in sterile PBS for each use.

Tumor Growth Inhibition In Vivo—CT26 Murine Colon Carcinoma

On Day 0, each mouse (6-8 weeks old, Balb/c) was inoculated subcutaneously at the right lower region with CT26 tumor cells ($5 \times 10^5$) in 0.1 ml of PBS for tumor development. The treatments were started 24 h after tumor cells inoculation. Mice were treated as follows:

| Group | N | Treatment | Dose (mg/kg) | Dosing Route | Dosing Schedule |
|---|---|---|---|---|---|
| 1 | 14 | Vehicle (0.5% HPMC, 0.05% Tween80, 7.5% Captisol) | 0 | p.o. | BID × 21 days |

-continued

| Group | N | Treatment | Dose (mg/kg) | Dosing Route | Dosing Schedule |
|---|---|---|---|---|---|
| 2 | 14 | I-1 | 50 | p.o. | BID × 21 days |
| 3 | 14 | Anti-PD-1 (RMP1-14) | 10 | i.p. | BIW × 3 weeks |
| 4 | 14 | I-1 Anti-PD-1 (RMP1-14) | 50 10 | p.o. i.p. | BID × 21 days BIW × 3 weeks |

Formulation, observations and sampling were as described above, with a satellite time point (5 mice/group) of Day 14 for some groups.

Tumor Dissociation and FACS Staining

Reagent Preparation

The Tumor Dissociation Kit (Miltenyi; #130-096-730) contain 2 vials of Enzyme D (lyophilized powder), 1 vial of Enzyme R (lyophilized powder), 1 vial of Enzyme A (lyophilized powder) and 1 ml of Buffer A. Enzyme D was prepared by reconstitution of the lyophilized powder in each vial 3 ml of RPML 1640 or DMEM. Enzyme R was prepared by reconstitution of the lyophilized powder in the vial with 2.7 ml RPMI 1640 or DMEM. Enzyme A was prepared by reconstitution of the lyophilized powder in the vial with 1 ml of Buffer A supplied with the kit, which was not vortexed. The enzyme mix was prepared by adding 2.35 ml of RPMI 1640 or DMEM, 100 µl of Enzyme D, 50 µl of Enzyme R, and 12.5 µl of Enzyme A into gentleMACS (Miltenyi; #130-096-334) Tubes.

Tumor Dissociation Using MACS Tumor Dissociator

Tumors were collected from mice, any non-tumor tissue was removed and the remaining tumor tissue was washed in PBS. The tumors were cut into pieces 1 mm$^3$ in PBS and washed twice in PBS with centrifugation at 300 g for 5 minutes. The tumor pieces were transferred into the gentleMACS Tubes containing the enzyme mix. The samples were then processed on a GentleMACS™ Octo Dissociator with Heaters (130-096-427) according to manufacturer's instructions for the dissociation program. The samples were then centrifuged and run through a strainer to obtain single-cell suspensions. The cell suspensions were then re-suspended with 5 ml wash buffer then adjusted to a cell concentration of 5*10^6 cells/mL.

FACS Staining

The cell suspensions were added to FACS tubes and 1 µl Fc-Block was added to each sample and the samples were incubated on ice for 15 minutes in the dark. Relevant FACS antibody mixtures that targeted surface markers were diluted in Fc blocking buffer and added to each sample. The cells were allowed to stain for 30 minutes on ice in the dark and then washed twice in PBS. The cells were resuspended in PBS and analyzed by a FACS machine.

To stain for intracellular markers, cells were resuspended in Fixation/Permeabilization (ThermoFisher) working solution and incubated overnight at 4° C. overnight or 30 min at room temperature in the dark. The cells were then washed twice using Permeabilization Buffer and incubated with primary antibodies in Permeabilization Buffer at room temperature for 30 minutes in the dark. The cells were washed again and resuspended in PBS and analyzed on a cytometer.

Results

Figure 1B:
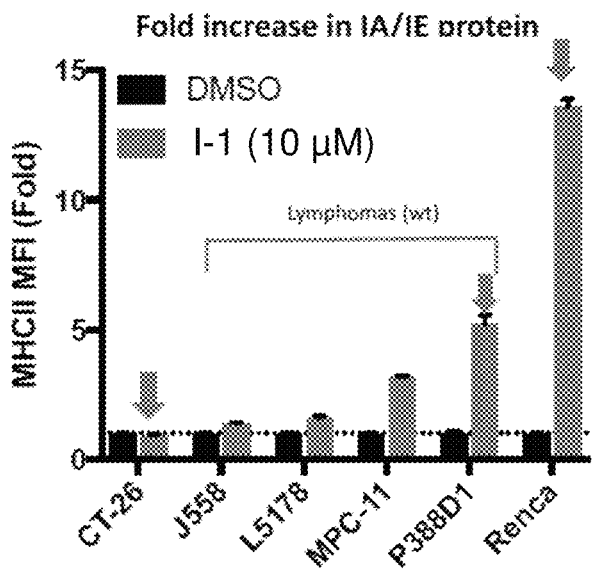
Figure 4A:
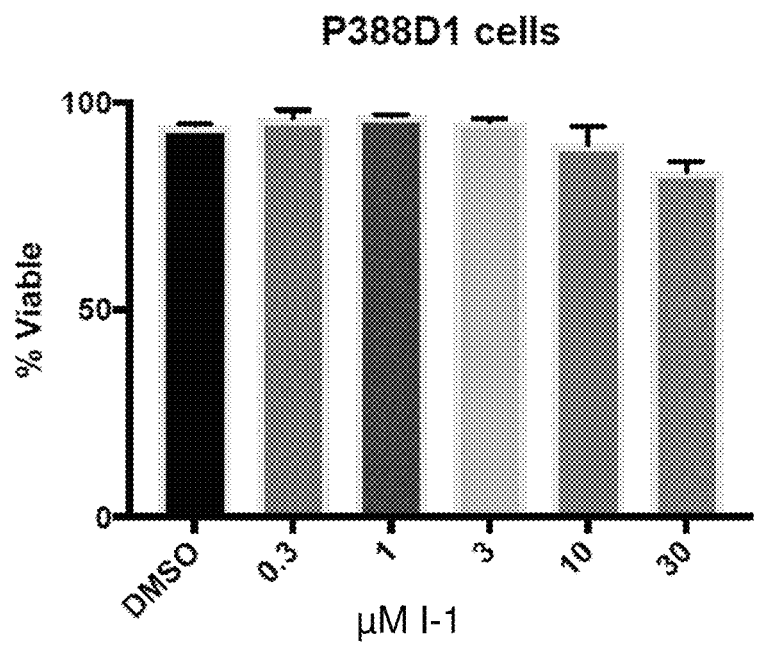
FIGS. 4A and 4B show cytotoxicity data for I-1.
Figure 4B:
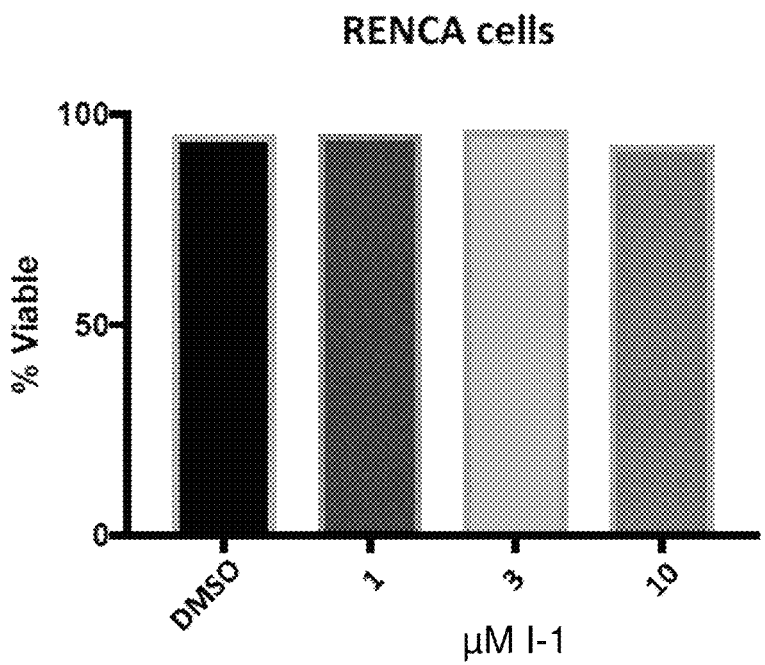
Figure 13:
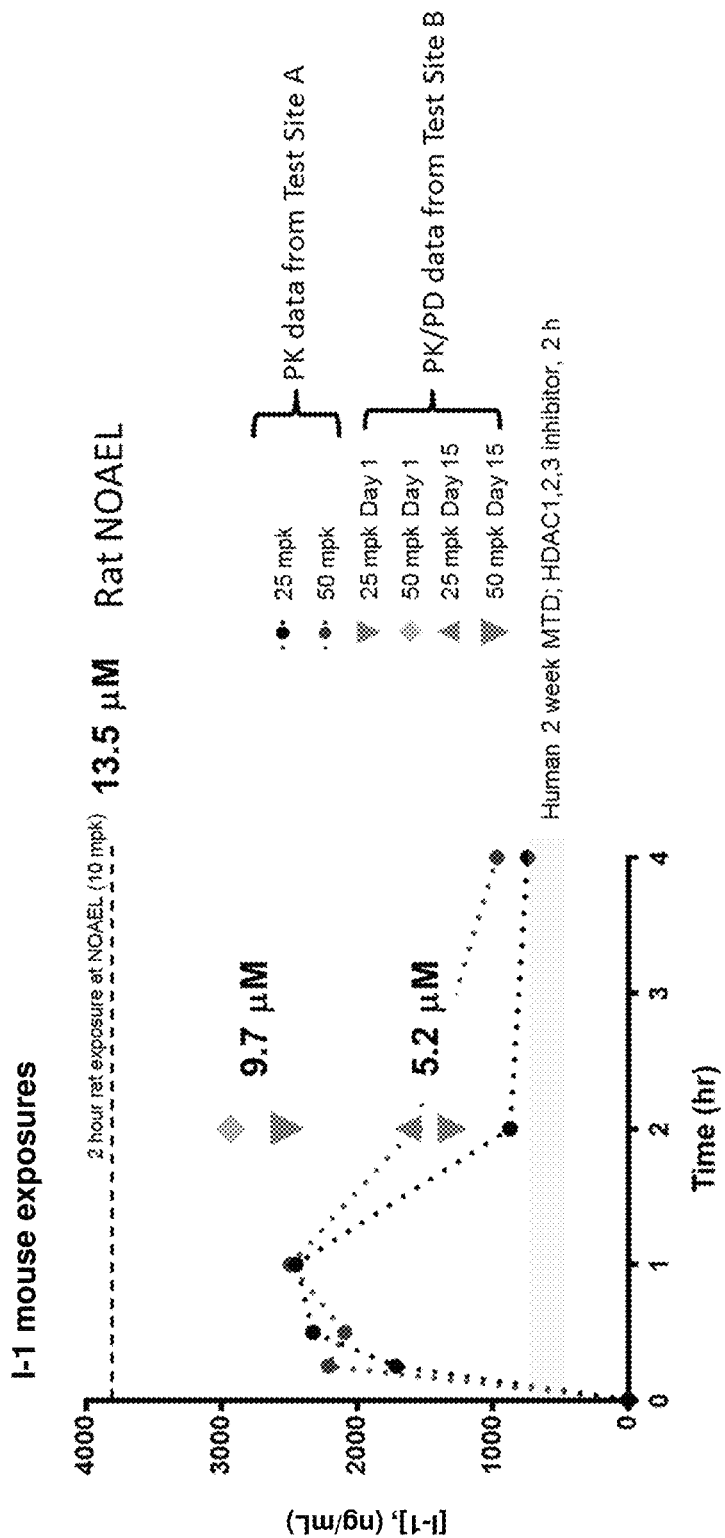
FIG. 13 shows I-1 plasma exposure above K, and below NOAEL (no adverse effect level).

First, the selective HDAC3 inhibitor I-1 was assessed as a single agent. As shown in FIG. 1, I-1 robustly increased MHC Class II expression across multiple cell lines (approximately 20-100% increase). The effects of I-1 were not CREBBP mutation dependent (i.e., an effect was seen in cells with the mutation and without) and were observed across different tumor types (both lymphomas and solid tumors). FIG. 4 shows that I-1 is generally not cytotoxic. Twenty-six syngeneic cells lines also showed minimal impact on viability when treated with 10 µM I-1. I-1 was well tolerated at 25 and 50 mg/kg, administered orally twice daily at 12 hour intervals (BID) and showed efficacy at levels below rat NOAEL (no adverse effect level) (FIG. 13). Further the tolerated exposures of I-1 exceeded the tolerated dose of a clinical HDAC 1,2,3 inhibitor by greater than 4× (FIG. 13). Anti-tumor efficacy of I-1 was seen at doses and exposures below the NOAEL. In summary, these data show that I-1 is capable of upregulating MHC Class II across multiple cell lines representing various tumor types and is non-toxic.

Figure 2A:
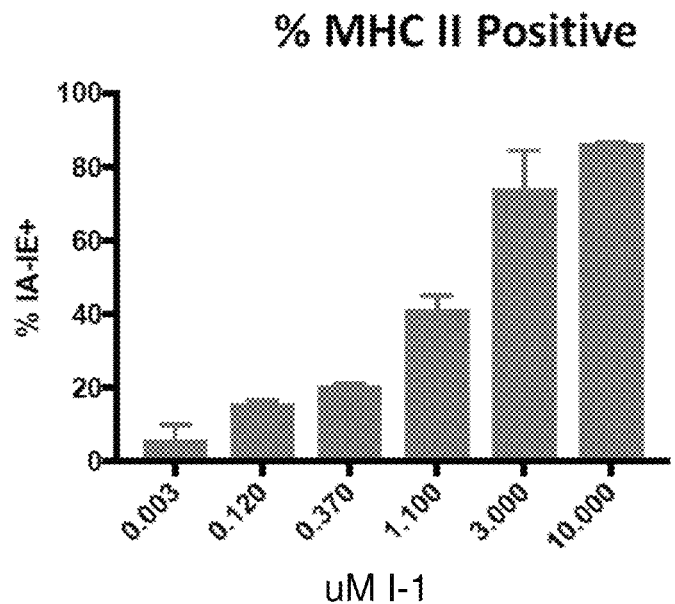
FIGS. 2A and 2B show dose responsive in vitro induction of MHC Class II (IA-IE) in P388D1 cells. "uM" denotes "µM".
Figure 2B:
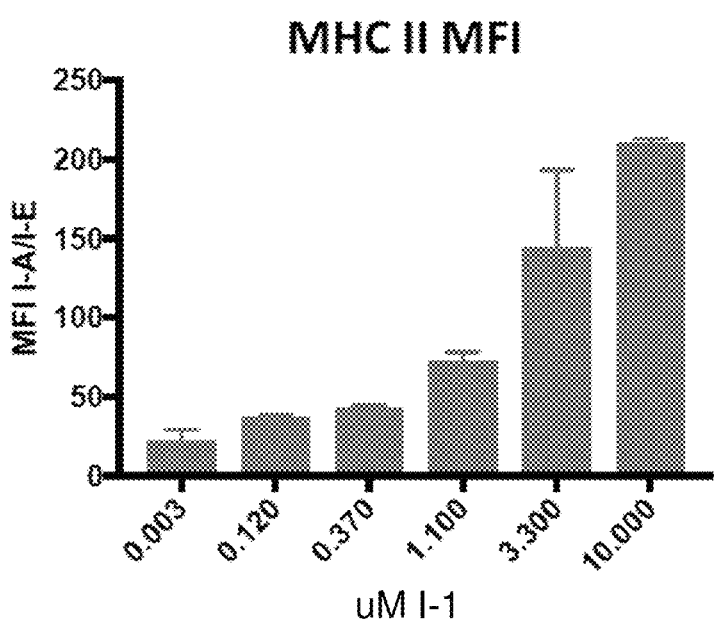
Figure 3A:
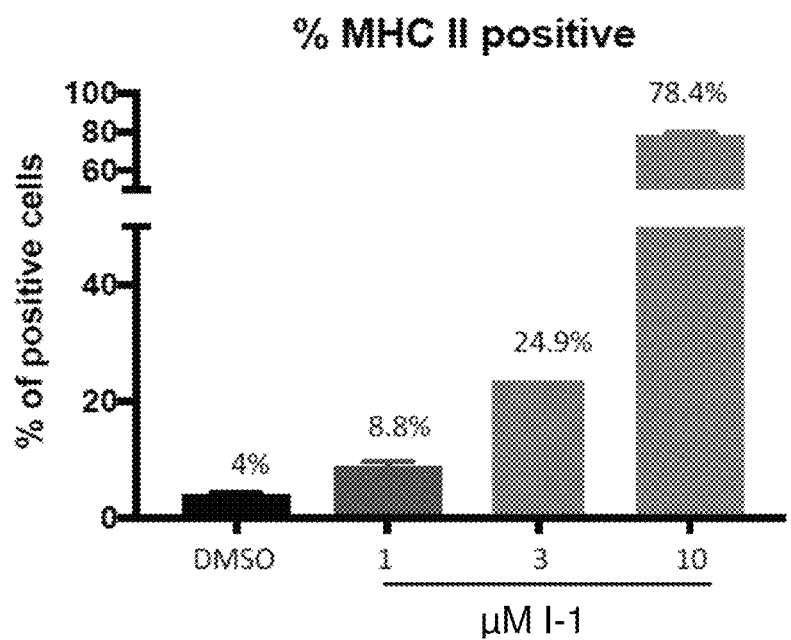
FIGS. 3A and 3B show dose responsive in vitro induction of MHC Class II (I-A/I-E) in RENCA cells.
Figure 3B:
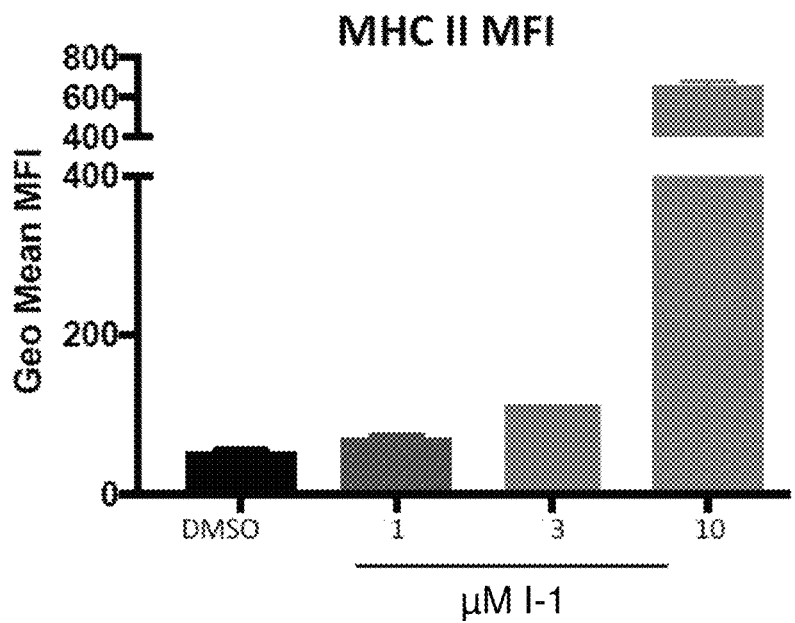
Figure 5A:
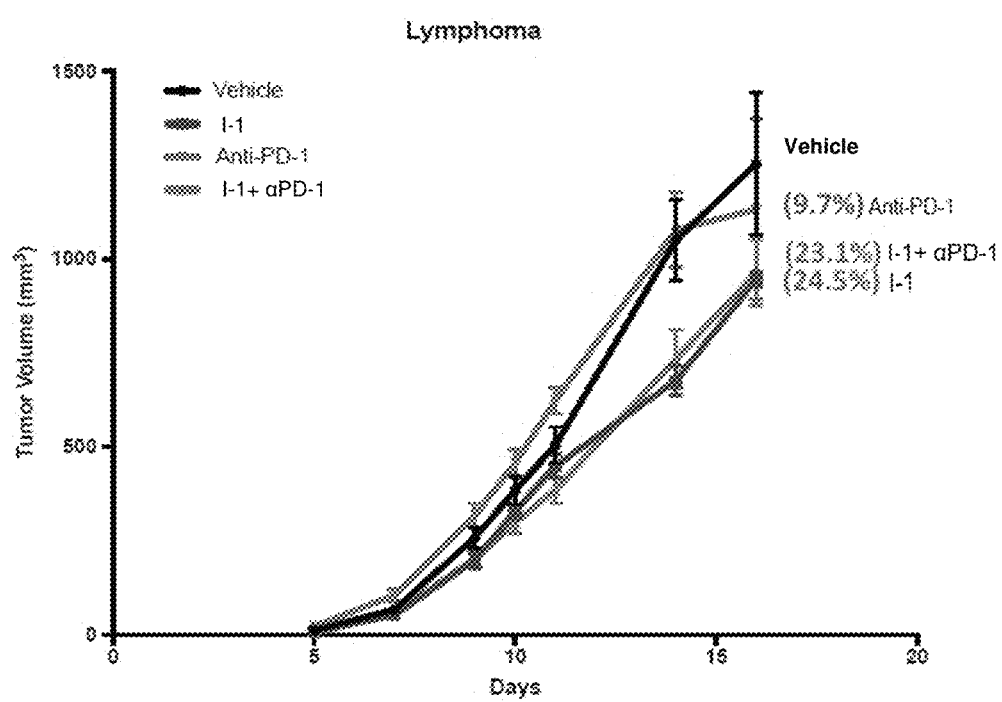
FIGS. 5A and 5B show that I-1, both alone and in combination with a checkpoint inhibitor, demonstrates pharmacodynamic activity (PD) and tumor growth inhibition in vivo in mice with P388D1 tumors.
Figure 5B:
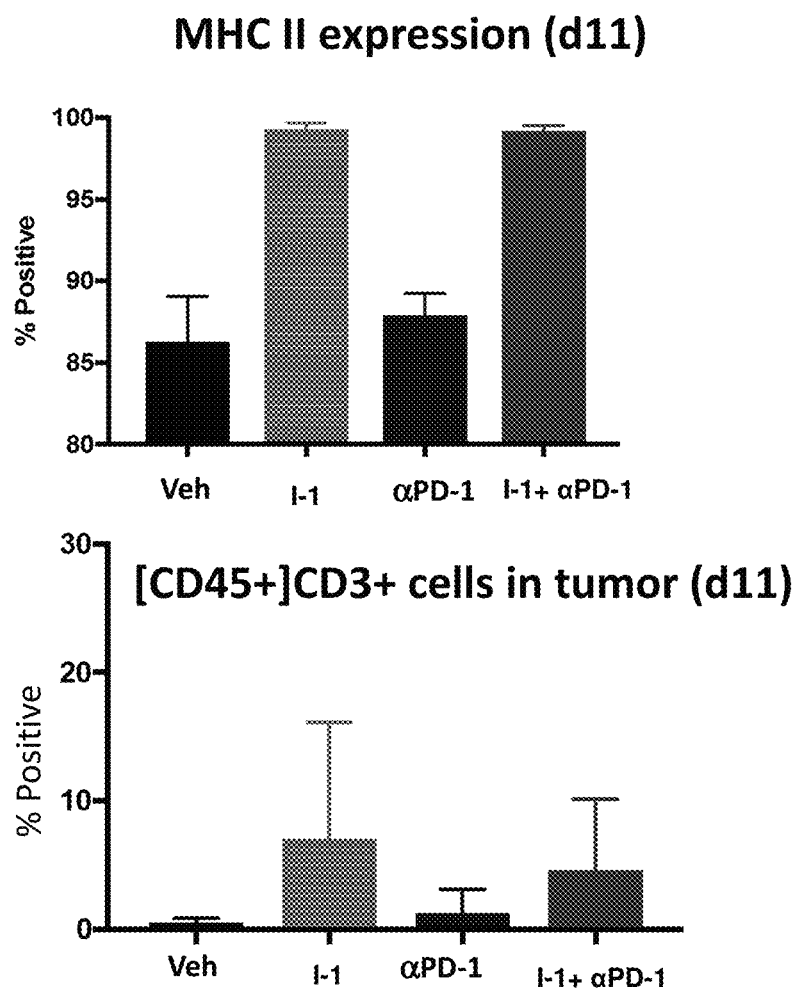
Figures 8A, 8B:
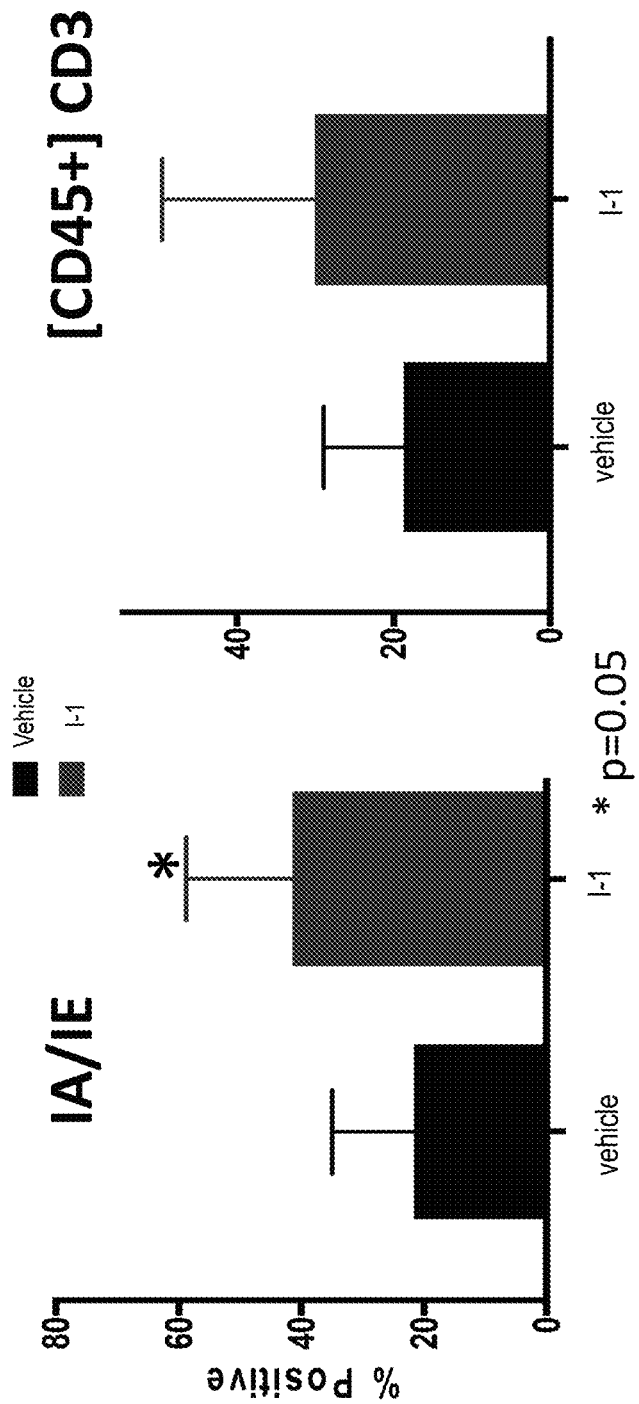
FIGS. 8A and 8B show that I-1 induces MHC Class II in vivo in mice with RENCA tumors, and that the tumors have increased CD3+ infiltrates.
Figure 9:
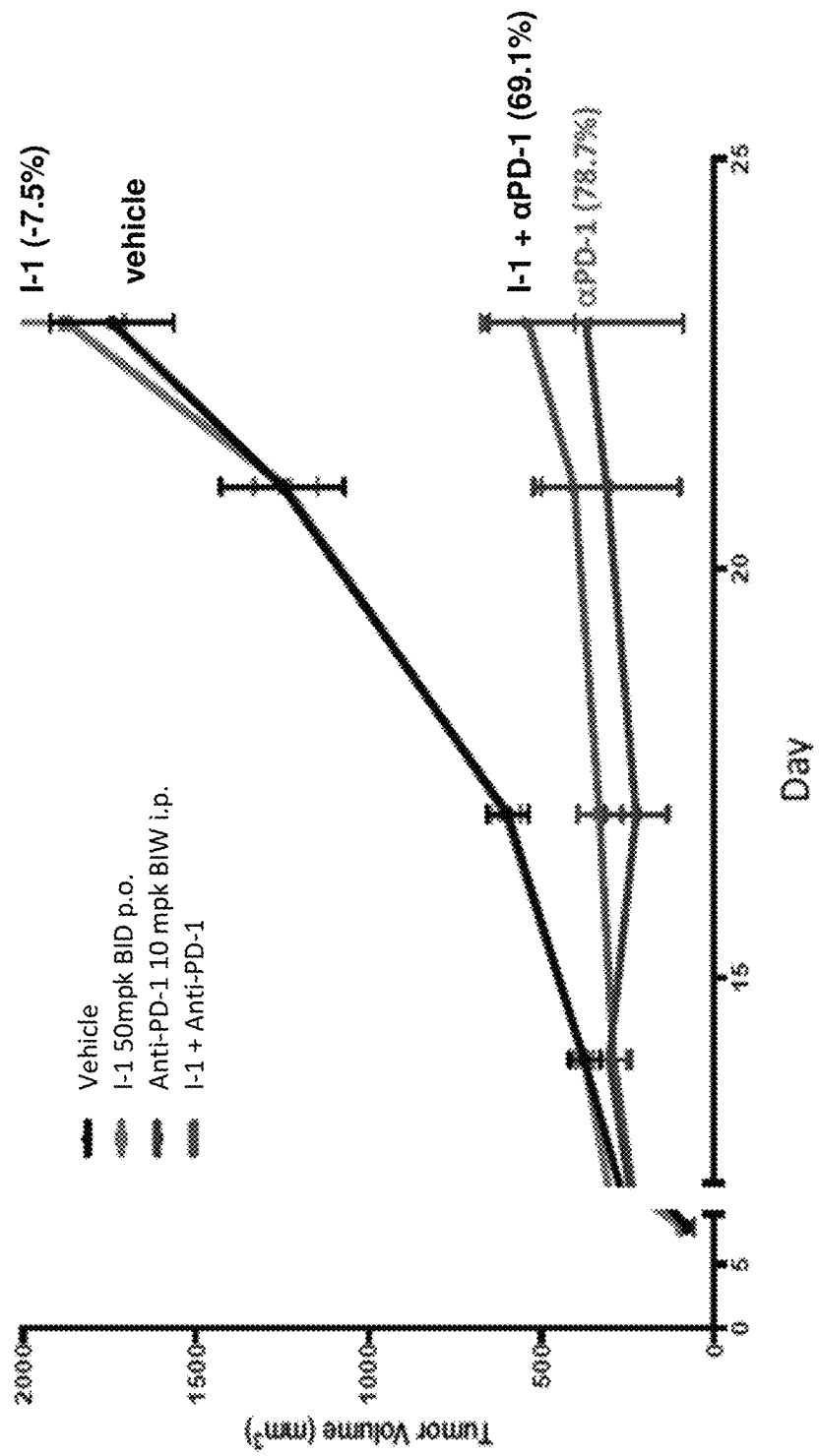
FIG. 9 shows the effect of a vehicle, I-1, anti-PD-1 antibody, or I-1+anti-PD-1 antibody treatment on CT26 tumor volume (mm$^3$) over several days, with treatment initiated at twenty four hours after tumor induction.

Next, the effects of I-1 on individual tumor cell lines in vitro and in vivo were assessed. As shown in FIG. 2, I-1 caused dose responsive in vitro induction of MHC class II (IA-IE) in P388D1 cells, with about 4× more cells being positive at 120 nM I-1, and about 13× more cells being positive at 3 µM I-1. I-1 also induced MHC class II in vivo in mice with P388D1 tumors and tumors from treated mice had increased CD3-positive infiltrates (FIGS. 5A and 5B). In addition, as shown in FIG. 3, I-1 caused dose responsive in vitro induction of MHC class II (IA-IE) in RENCA cells, with about 2× more cells being positive at 1 µM I-1 and about 6× more cells being positive at 3 µM I-1. I-1 also induced MHC Class II in vivo in mice with RENCA tumors and tumors from treated mice had increased CD3-positive infiltrates (FIGS. 8A and 8B). In contrast, I-1 did not appear to induce in vitro MHC Class II (IA-IE) in CT26 mouse colon tumor cells. Additionally, I-1 did not induce TGI (tumor growth inhibition) in vivo in mice with CT26 tumors (FIG. 9).

Next, various cell lines shown to be responsive to the HDAC3 inhibitor were assessed for immune cell infiltration and responsiveness to checkpoint inhibitors. P388D1 tumors were shown to be very poorly infiltrated by immune cells (mean approx. 0% macrophage infiltration and mean approx. 5% T cell infiltration). In contrast, RENCA tumors were shown to have macrophage infiltration (mean approx. 30%) and T cell infiltration (mean approx. 50%). P388D1 tumors were also shown to be minimally responsive to checkpoint inhibitor monotherapy (less than about 10% TGI for anti-PD-1 antibody and less than about 20% TGI for anti-PD-L1 antibody). RENCA tumors were shown to be refractory to a certain checkpoint inhibitor monotherapy (PD-1 antibody, about −60% TGI) and minimally responsive to a different checkpoint inhibitor monotherapy (PD-L1 antibody, less than about 20% TGI). CT26 tumors were shown to be refractory to a certain checkpoint inhibitor monotherapy (PD-L1 antibody, about −40% TGI) and variably responsive to a different checkpoint inhibitor monotherapy (PD-1 antibody, ranging from about 10% to about 79% TGI).

Next, a combination of an HDAC3 inhibitor and checkpoint inhibitor were assessed in different tumor models.

I-1 was shown to be effective, both alone and in combination with a checkpoint inhibitor (anti-PD-1 antibody) in treating P388D1 tumors in mice, although the addition of the checkpoint inhibitor did not appear to increase efficacy (FIGS. 5A and 5B). Without wishing to be bound by theory, this tumor model is believed to be minimally responsive to anti-PD1 therapy because this tumor model does not recruit immune cell infiltrate effectively, explaining the lack of any added benefit when combining I-1 with the anti-PD1 antibody due to the minimal immune cell involvement in this tumor model.

Figure 6:
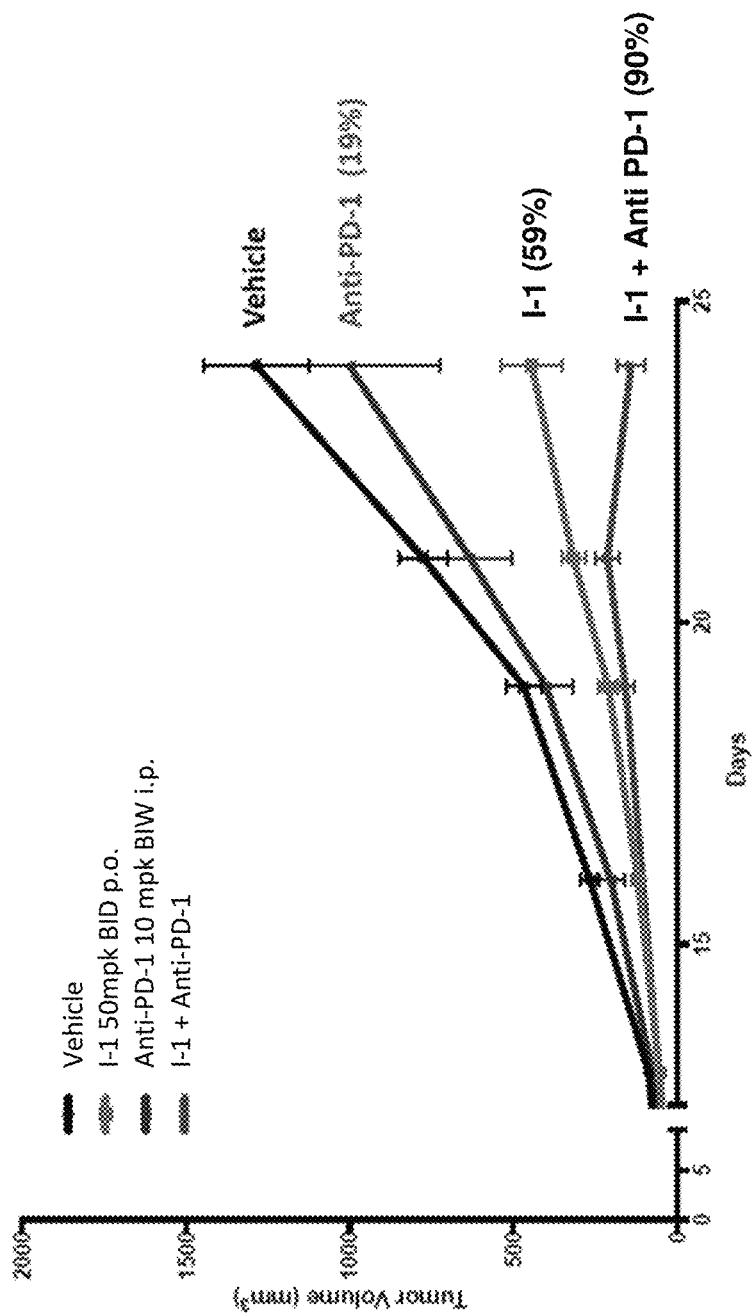
FIG. 6 shows that I-1, both alone and in combination with a checkpoint inhibitor, demonstrates efficacy in vivo in mice with RENCA tumors. Treatment was initiated at 24 hours after tumor induction.

I-1 was also shown to be effective in treating RENCA tumors in mice, and the combination of I-1 and a checkpoint inhibitor (anti-PD-1 antibody) was shown to be even more effective than either agent used alone (FIG. 6). In contrast to the P388D1 tumor model, the RENCA tumor model has a stronger baseline recruitment of immune cells, which was increased even further upon treatment with I-1 (FIG. 8B). Despite stronger immune cell involvement, however, anti-PD1 therapy alone was insufficient to achieve significant anti-tumor activity (FIG. 6). Without wishing to be bound by theory, when the tumor was treated with the combination of anti-PD1 therapy and I-1, it is believed that the tumor became more sensitive to anti-PD1 therapy because I-1 increased MHC class II antigen presentation on the RENCA tumor cells and the corresponding increase in immune cell infiltrate. Individual responses of mice with RENCA tumors were then assessed and significant regression and complete responses (CR) were observed in individual mice treated with the combination of I-1 and a checkpoint inhibitor (anti-PD-1 antibody) (FIG. 7A to 7D), with greater than or equal to 20% CRs in the combination treatment group.

I-1 was not effective in treating CT26 tumors in mice (FIG. 9). CT26 cells did not express MHC class II in response to I-1 treatment. A checkpoint inhibitor (anti-PD-1 antibody) was effective in treating CT26 tumors but no added benefit was observed from the combination of I-1 and anti-PD-1 antibody (FIG. 9). Without wishing to be bound by theory, these results are consistent with the hypothesis that MHC class II induction and expression mediates the I-1-driven anti-tumor response in vivo; there was no observed efficacy with I-1 alone, and no added benefit to combining I-1 with anti-PD1 treatment because no MHC class II was induced by I-1 on the CT26 tumor cells.

Figure 10:
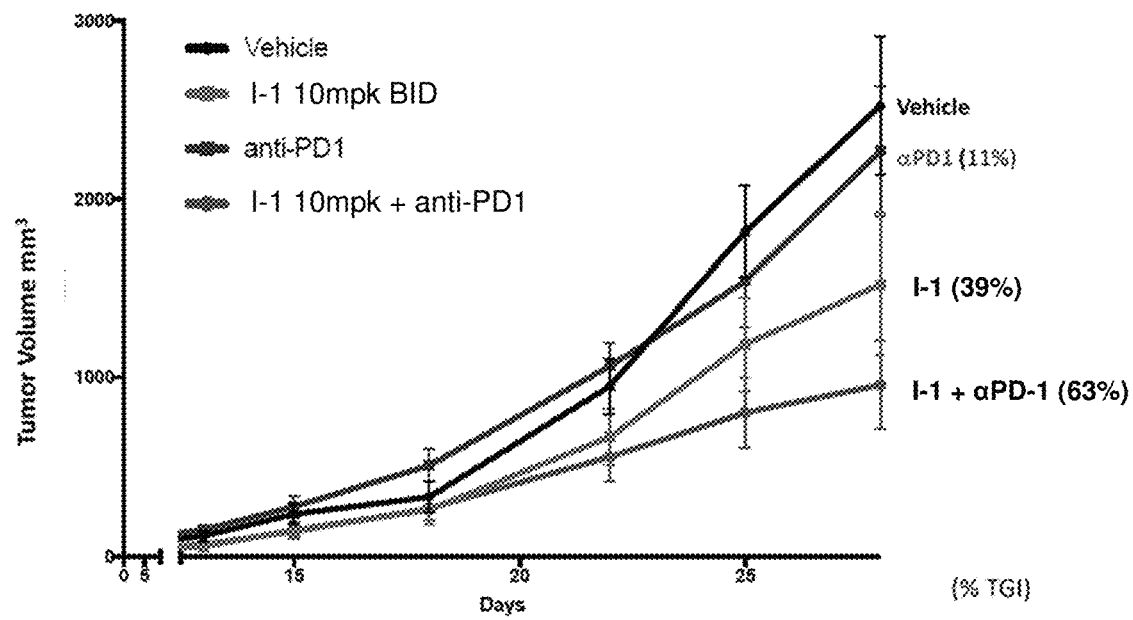
FIG. 10 shows RENCA tumor response for the 10 mg/kg I-1 (twice daily at 12 hour intervals, BID) in combination with Anti-PD-1 antibody.
Figure 11:
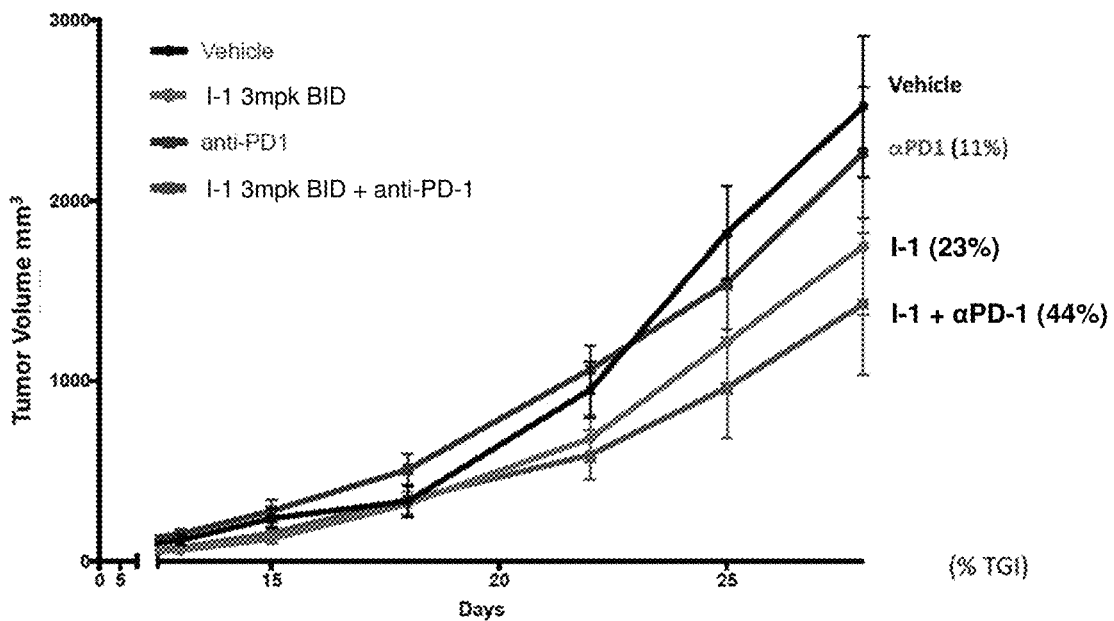
FIG. 11 shows RENCA tumor response for the 3 mg/kg I-1 (twice daily at 12 hour intervals, BID) in combination with Anti-PD-1 antibody.

Next, the combination of HDAC3 inhibitor and checkpoint inhibitor was further assessed in the RENCA model. I-1 was shown to be effective at both 10 mg/kg and 3 mg/kg administered twice daily at 12 hour intervals (BID) and the effectiveness was enhanced with the combination of I-1 and a checkpoint inhibitor (anti-PD-1 antibody) (FIGS. 10 and 11).

Figure 12:
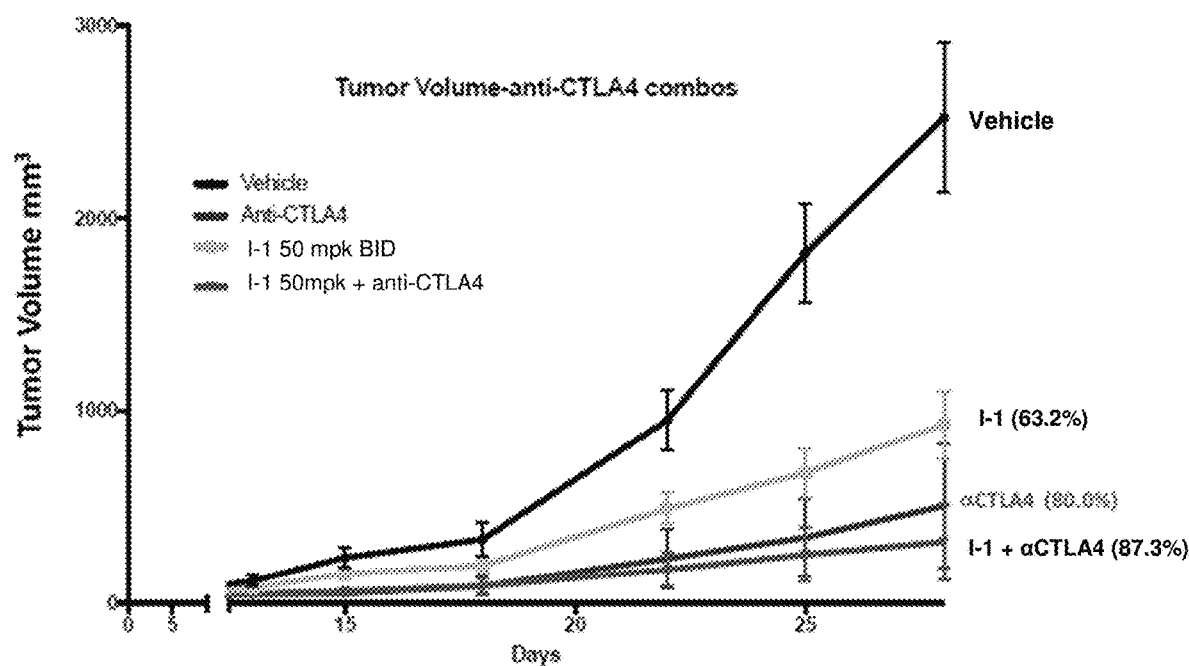
FIG. 12 shows RENCA tumor response for the 50 mg/kg I-1 (twice daily at 12 hour intervals, BID) in combination with anti-CTLA4 antibody (Anti-CTLA4 or αCTLA4).

Lastly, a second checkpoint inhibitor (anti-CTLA4 antibody) was assessed in combination with the HDAC3 inhibitor (I-1) in the RENCA model. The anti-CTLA4 antibody was shown to improve efficacy of I-1 when the two therapies were used in combination (FIG. 12). In this experiment, the dose of anti-CTLA4 antibody used was sufficient to induce a strong anti-tumor response alone (FIG. 12). As a result, the modest combination benefit seen with I-1 and anti-CTLA4 antibody may be due to the fact that the anti-tumor response was already so strong with the anti-CTLA4 antibody alone that the benefit of addition of I-1 may be partially masked. Using lower doses of anti-CTLA4 antibody (to reduce the anti-tumor response), it is possible that a stronger benefit to the I-1 and anti-CTLA4 antibody combination may be observed.

Taken together, these data show that the combination of an HDAC3 inhibitor, such as I-1, and a checkpoint inhibitor, such as an anti-PD-1 or anti-CTL4 antibody, can be more effective in certain cancers than either inhibitor alone. As to the different effects observed in different cancer cell lines, without wishing to be bound by theory, it is believed that in order for the combination to be effective, the tumor may need to respond to the HDAC3 inhibitor by upregulating MHC Class II and also may also need to have infiltration of macrophages and/or T cells in the tumor, as was the case in RENCA tumors. P388D1 tumors did have some infiltration of macrophages and T cells as well but this particular tumor model grew so rapidly that it was difficult to assess within the available window of time before morbidity whether there was any added benefit to the combination therapy over I-1 administered alone.

Example 3. Selective HDAC3 Inhibitors Increase MHC II Levels

Figure 14:
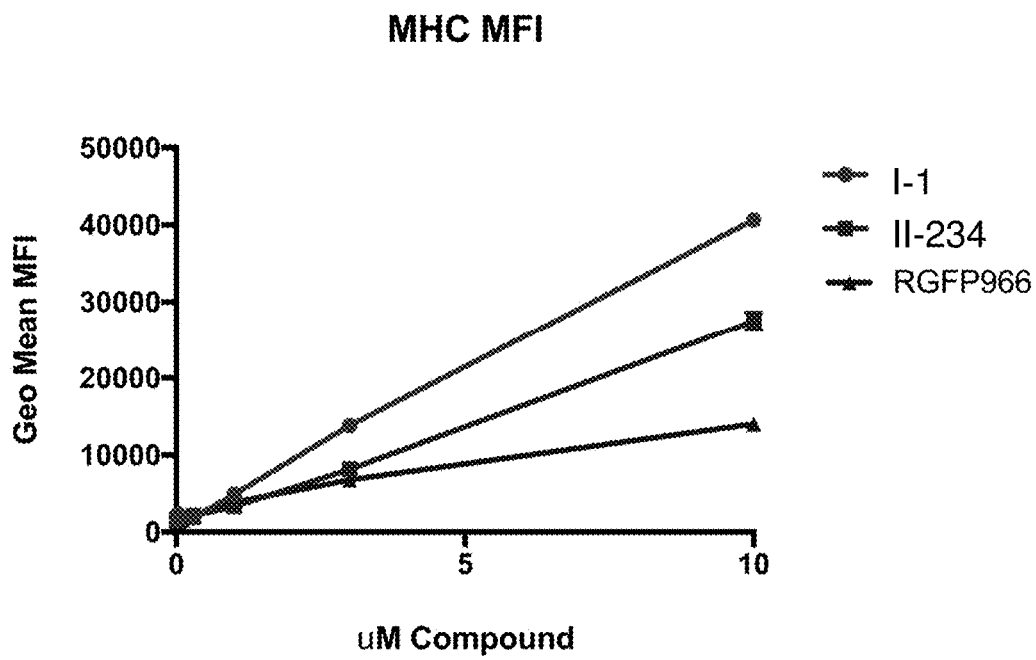
FIG. 14 shows geometric mean MFI (mean fluorescence intensity) for MHC Class II in P388D1 cells in the presence of various concentrations of I-1, II-234, and RGFP966. "uM" denotes "µM".
Figure 15:
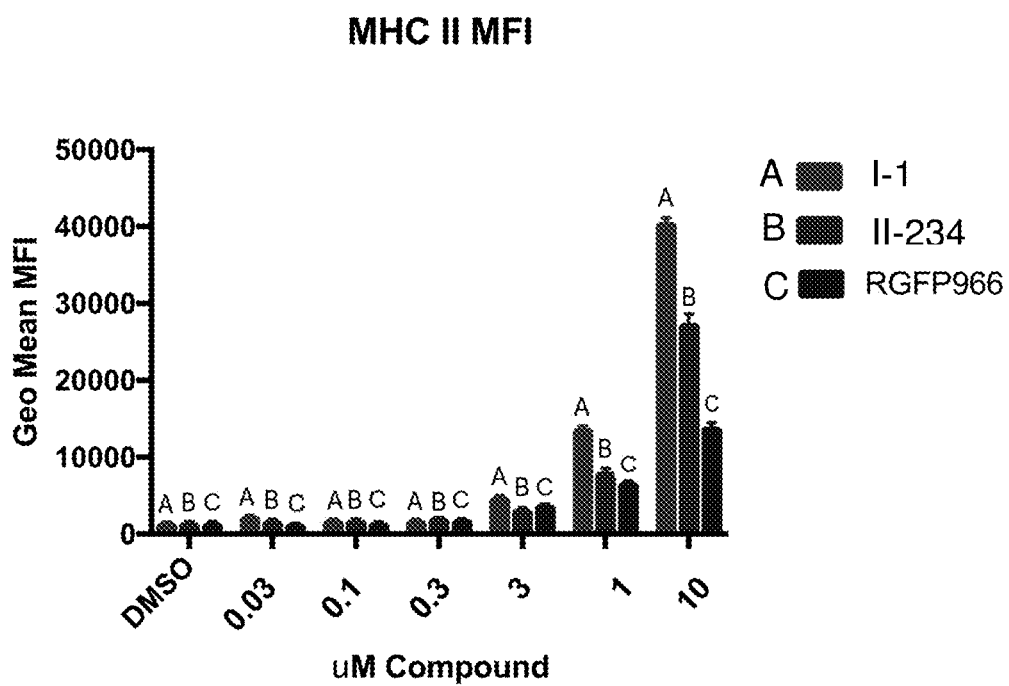
FIG. 15 shows geometric mean MFI (mean fluorescence intensity) for MHC Class II in P388D1 cells in the presence of DMSO or various concentrations of I-1, II-234, and RGFP966. "uM" denotes "μM".

The selective HDAC3 inhibitor I-1 was compared to additional selective HDAC3 inhibitors II-234 and RGFP966. I-1, II-234 and RGFP966 were all shown to be capable of increasing MHC class II protein levels in P388D1 cells in a dose-dependent manner, with I-1 having the most activity, followed by 11-234 and then RGFP966 (FIGS. 14 and 15). These data confirm that selective HDAC3 inhibitors are capable of increasing MHC II levels in certain cancer cells. As a result, it is expected that additional selective HDAC3 inhibitors, such as 11-234 and RGFP966, will work with checkpoint inhibitors as described in Example 3.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of treating cancer in a subject in need thereof comprising:
   administering a selective histone deacetylase 3 (HDAC3) inhibitor to the subject in need thereof, wherein the selective HDAC3 inhibitor is more active for inhibiting HDAC3 than for inhibiting a histone deacetylase that is not HDAC3; and
   administering an immune checkpoint inhibitor to the subject in need thereof;
   wherein:
   the cancer is lymphoma or kidney cancer;
   the immune checkpoint inhibitor is an antibody to: programmed cell death 1 protein (PD-1) or programmed cell death 1 protein ligand 1 (PD-L1);
   the amount of the selective HDAC3 inhibitor is effective for increasing expression of an MHC class II protein in at least one of the cancer cells;
   the step of administering the selective HDAC3 inhibitor is prior to, concurrently with, or subsequent to the step of administering the immune checkpoint inhibitor;
   the combined amount of the selective HDAC3 inhibitor and the immune checkpoint inhibitor is effective for treating the cancer;
   the selective HDAC3 inhibitor and the immune checkpoint inhibitor act synergistically to treat the cancer compared to either the selective HDAC3 inhibitor or the immune checkpoint inhibitor used alone; and
   the selective HDAC3 inhibitor is a compound of Formula (I):

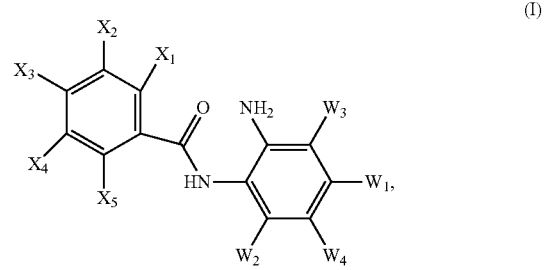

or a pharmaceutically acceptable salt, hydrate, or solvate thereof, wherein:
   $W_1$ is fluorine;
   each of $W_2$, $W_3$, and $W_4$ is hydrogen;
   $X_1$ and $X_5$ are each independently selected from hydrogen and halogen;
   $X_3$ is $-NR^1C(O)R^2$;

$X_2$ and $X_4$ are each independently hydrogen or halogen, provided that one or two of $X_2$, and $X_4$ is hydrogen;

$R^1$ is selected from hydrogen and $C_1$-$C_8$ alkyl;

$R^2$ is selected from $C_1$-$C_8$ alkyl, $C_2$-$C_8$ alkenyl, and $C_3$-$C_8$ alkynyl, wherein said alkyl, alkenyl, and alkynyl are independently unsubstituted or substituted with one or more $R^b$;

each instance of $R^b$ is independently selected from halogen, $OR^{25}$, $NH_2$, $NHCH_3$, and $N(CH_3)_2$; and each instance of $R^{25}$ is independently selected from hydrogen, $C_1$-$C_8$ alkyl, $CF_3$, $CHF_2$, $CH_2F$, $C_2$-$C_8$ alkenyl, and $C_3$-$C_8$ alkynyl.

2. The method of claim 1, wherein the cancer is kidney cancer.

3. The method of claim 1, wherein the selective HDAC3 inhibitor is a compound of the formula:

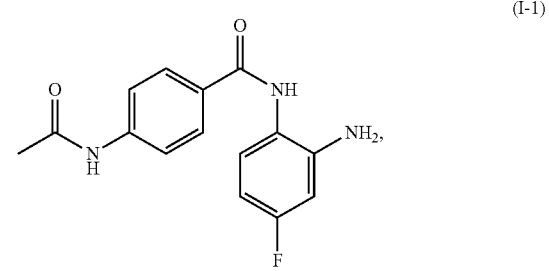 [SMILES: CC(=O)Nc1ccc(C(=O)Nc2ccc(F)cc2N)cc1]

(I-1)

or a pharmaceutically acceptable salt, hydrate, or solvate thereof.

4. The method of claim 1, wherein the selective HDAC3 inhibitor is a compound of the formula:

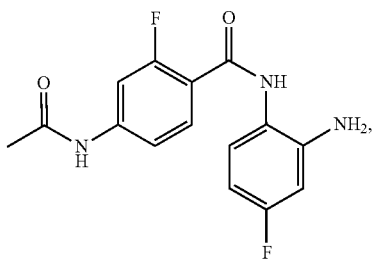

(I-6)

or a pharmaceutically acceptable salt, hydrate, or solvate thereof.

5. The method of claim 1, wherein $X_3$ is $NHC(O)R^2$.

6. The method of claim 1, wherein $X_3$ is $NHC(O)CH_3$.

7. The method of claim 1, wherein each of $X_1$, $X_2$, $X_4$, and $X_5$ is independently hydrogen or fluoro.

8. The method of claim 5, wherein the selective HDAC3 inhibitor is a compound of the formula:

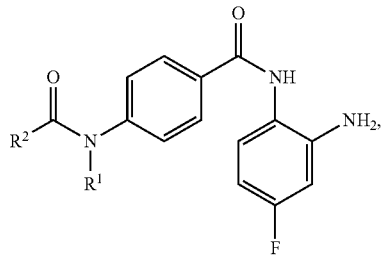

or a pharmaceutically acceptable salt, hydrate, or solvate thereof.

9. The method of claim 1, wherein the selective HDAC3 inhibitor is a compound of the formula:

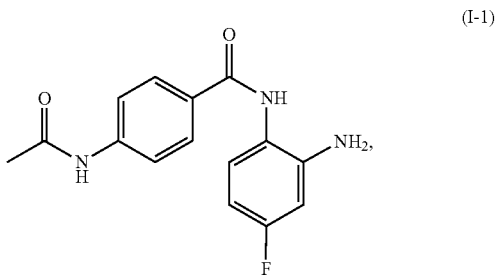 [SMILES: CC(=O)Nc1ccc(C(=O)Nc2ccc(F)cc2N)cc1]

(I-1)

or a pharmaceutically acceptable salt thereof.

10. The method of claim 1, wherein the immune checkpoint inhibitor is an antibody to programmed cell death 1 protein (PD-1).

11. The method of claim 1, wherein the lymphoma is non-Hodgkin's lymphoma.

12. The method of claim 1, wherein the lymphoma is B-cell non-Hodgkin's lymphoma.

13. The method of claim 1, wherein the lymphoma is diffuse large B-cell lymphoma.

14. The method of claim 1, wherein the lymphoma is follicular lymphoma.

15. The method of claim 1, wherein the lymphoma is Hodgkin's lymphoma.

16. The method of claim 1, wherein the selective HDAC3 inhibitor is a compound of Formula (I), or a pharmaceutically acceptable salt thereof.

17. The method of claim 1, wherein the immune checkpoint inhibitor is an antibody to programmed cell death 1 protein (PD-1) or programmed cell death 1 protein ligand 1 (PD-L1); and is a monoclonal antibody.

18. The method of claim 9, wherein the immune checkpoint inhibitor is an antibody to programmed cell death 1 protein (PD-1) or programmed cell death 1 protein ligand 1 (PD-L1); and is a monoclonal antibody.

19. The method of claim 1, wherein the subject is a human.

20. The method of claim 1, wherein the immune checkpoint inhibitor is an antibody to programmed cell death 1 protein (PD-1) or programmed cell death 1 protein ligand 1 PD-L1) selected from is nivolumab, pidilizumab, pembrolizumab, MEDI-0680, REGN2810, or AMP-224.

21. The method of claim 1, wherein the immune checkpoint inhibitor is an antibody to programmed cell death 1 protein (PD-1) or programmed cell death 1 protein ligand 1 (PD-L1) selected from is atezolizumab, durvalumab, BMS-936559, avelumab, or CA-170.

22. The method of claim 9, wherein the immune checkpoint inhibitor is an antibody to programmed cell death 1 protein (PD-1) or programmed cell death 1 protein ligand 1 (PD-L1) selected from is nivolumab, pidilizumab, pembrolizumab, MEDI-0680, REGN2810, or AMP-224.

23. The method of claim 9, wherein the immune checkpoint inhibitor is an antibody to programmed cell death 1 protein (PD-1) or programmed cell death 1 protein ligand 1 (PD-L1) selected from is atezolizumab, durvalumab, BMS-936559, avelumab, or CA-170.

24. The method of claim 9, wherein the cancer is non-Hodgkin's lymphoma.

25. The method of claim 9, wherein the lymphoma is B-cell non-Hodgkin's lymphoma.

26. The method of claim 9, wherein the lymphoma is diffuse large B-cell lymphoma.

27. The method of claim 9, wherein the lymphoma is follicular lymphoma.

28. The method of claim 9, wherein the lymphoma is Hodgkin's lymphoma.

29. The method of claim 9, wherein the cancer is kidney cancer.

30. The method of claim 9, wherein the subject is a human.

31. The method of claim 9, wherein the immune checkpoint inhibitor is an antibody to programmed cell death 1 protein (PD-1).

32. The method of claim 31, wherein the lymphoma is Hodgkin's lymphoma or non-Hodgkin's lymphoma.

33. The method of claim 1, wherein the immune checkpoint inhibitor is an antibody to programmed cell death 1 protein ligand 1 (PD-L1).

34. The method of claim 9, wherein the immune checkpoint inhibitor is an antibody to programmed cell death 1 protein ligand 1 (PD-L1).

\* \* \* \* \*